US009081878B2

(12) United States Patent
Rofougaran

(10) Patent No.: US 9,081,878 B2
(45) Date of Patent: Jul. 14, 2015

(54) BIO-MEDICAL UNIT AND APPLICATIONS FOR CANCER TREATMENT

(75) Inventor: Ahmadreza (Reza) Rofougaran, Newport Coast, CA (US)

(73) Assignee: Broadcom Corporation, Irvine, CA (US)

(*) Notice: Subject to any disclaimer, the term of this patent is extended or adjusted under 35 U.S.C. 154(b) by 982 days.

(21) Appl. No.: 12/649,049

(22) Filed: Dec. 29, 2009

(65) Prior Publication Data
US 2011/0077580 A1  Mar. 31, 2011

Related U.S. Application Data

(60) Provisional application No. 61/247,060, filed on Sep. 30, 2009.

(51) Int. Cl.
G06F 19/00 (2011.01)
(Continued)

(52) U.S. Cl.
CPC ............ G06F 19/34 (2013.01); A61K 9/0009 (2013.01); A61M 31/002 (2013.01); G06F 19/323 (2013.01); G06F 19/3418 (2013.01); G06F 19/3468 (2013.01); G06Q 50/22 (2013.01); H04L 12/10 (2013.01); A61M 2205/3507 (2013.01); A61M 2205/3523 (2013.01); A61M 2205/3592 (2013.01); Y02B 60/33 (2013.01)

(58) Field of Classification Search
CPC . G06F 19/34; G06F 19/3406; G06F 19/3412; G06F 19/3418; G06F 19/3468; A61M 2205/3507; A61M 2205/3515; A61M 2205/3523; A61M 2205/3569; A61M 2205/3576; A61M 2205/3584; A61M 2205/3592; A61M 5/14276; A61M 5/172; A61M 31/002; A61K 9/0009
USPC ................ 604/19–21, 501, 890.1, 891.1; 128/897–899
See application file for complete search history.

(56) References Cited

U.S. PATENT DOCUMENTS 6,240,312 B1 * 5/2001 Alfano et al. ................. 600/476
6,245,057 B1 * 6/2001 Sieben et al. .............. 604/891.1

(Continued)

OTHER PUBLICATIONS

Malcolm Gibson, Ultrasound as a Proposed Drug Release Mechanism in Biomedical Microrobots, Arizona Space Grant Consortium, Univ. of Arizona Advanced Microsystems Laboratory, Dept. of Aerospace and Mechanical Engineering, 17 pp.

(Continued)

Primary Examiner — Kami A Bosworth
(74) Attorney, Agent, or Firm — Garlick & Markison; Bruce E. Garlick

(57) ABSTRACT

An in vivo cancer treatment system includes a plurality of bio-medical units, a communication control device, and a wireless power source device. A bio-medical unit of the plurality of bio-medical units includes a power harvesting module operable to convert a wireless power source into a supply voltage; a communication module operable to communication data, wherein the communication unit is powered by the supply voltage; and a field generation module operable to generate a type of electromagnetic field, wherein the field generation module is powered by the supply voltage. The communication control device communicates with the plurality of bio-medical units to facilitate treatment of cancer cells within the body. The wireless power source device generates the wireless power source.

20 Claims, 37 Drawing Sheets

(51) Int. Cl.

| | |
|---|---|
| *A61M 31/00* | (2006.01) |
| *A61K 9/00* | (2006.01) |
| *G06Q 50/22* | (2012.01) |
| *H04L 12/10* | (2006.01) |

(56) References Cited

U.S. PATENT DOCUMENTS

| | | |
|---|---|---|
| 6,845,267 B2 * | 1/2005 | Harrison et al. .................. 607/3 |
| 7,125,382 B2 | 10/2006 | Zhou et al. |
| 7,241,266 B2 | 7/2007 | Zhou et al. |
| 7,266,269 B2 | 9/2007 | Koste et al. |
| 2001/0051766 A1 * | 12/2001 | Gazdzinski .................. 600/309 |
| 2008/0146986 A1 * | 6/2008 | Riga et al. ...................... 604/20 |
| 2009/0227988 A1 * | 9/2009 | Wood et al. ................. 604/891.1 |
| 2010/0189779 A1 * | 7/2010 | Herbert et al. ................ 424/451 |

OTHER PUBLICATIONS

Robert E. Carlson, Ph.D., et al., "Development of an Implantable Glucose Sensor", 16 pp.

Robert Moffatt, et al., "WiTricity: Non-Radiative Wireless Power Transfer", 56 pp.

Arjang Hassibi, et al., "A Spectral-Scanning Nuclear Magnetic Resonance Imaging (MRI) Transceiver", IEEE Journal of Solid-State Circuits, Jun. 2009, pp. 1805-1813, vol. 44, No. 6.

John E. Speich, et al., "Medical Robotics", Encyclopedia of Biomaterials and Biomedical Engineering, 2004, pp. 983-992, Marcel Dekker, Inc.

Eric Freudenthal, et al., "Evaluation of HF RFID for Implanted Medical Applications", Apr. 16, 2006, 4 pp.

Shekhar Bhansali, Role of MEMS and Nanotechnology in Medical Technologies, University of South Florida, 29 pp.

* cited by examiner

BIO-MEDICAL UNIT AND APPLICATIONS FOR CANCER TREATMENT

CROSS REFERENCE TO RELATED PATENTS

This patent application is claiming priority under 35 USC §119 to a provisionally filed patent application entitled BIO-MEDICAL UNIT AND APPLICATIONS THEREOF, having a provisional filing date of Sep. 30, 2009, and a provisional Ser. No. 61/247,060.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Technical Field of the Invention

This invention relates generally to medical equipment and more particularly to wireless medical equipment.

2. Description of Related Art

As is known, there is a wide variety of medical equipment that aids in the diagnosis, monitoring, and/or treatment of patients' medical conditions. For instances, there are diagnostic medical devices, therapeutic medical devices, life support medical devices, medical monitoring devices, medical laboratory equipment, etc. As specific exampled magnetic resonance imaging (MRI) devices produce images that illustrate the internal structure and function of a body.

The advancement of medical equipment is in step with the advancements of other technologies (e.g., radio frequency identification (RFID), robotics, etc.). Recently, RFID technology has been used for in vitro use to store patient information for easy access. While such in vitro applications have begun, the technical advancement in this area is in its infancy.

Therefore, a need exists for a bio-medical unit that has applications for cancer treatment.

BRIEF SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE SEVERAL VIEWS OF THE DRAWING(S)

DETAILED DESCRIPTION OF THE INVENTION

Figure 1:
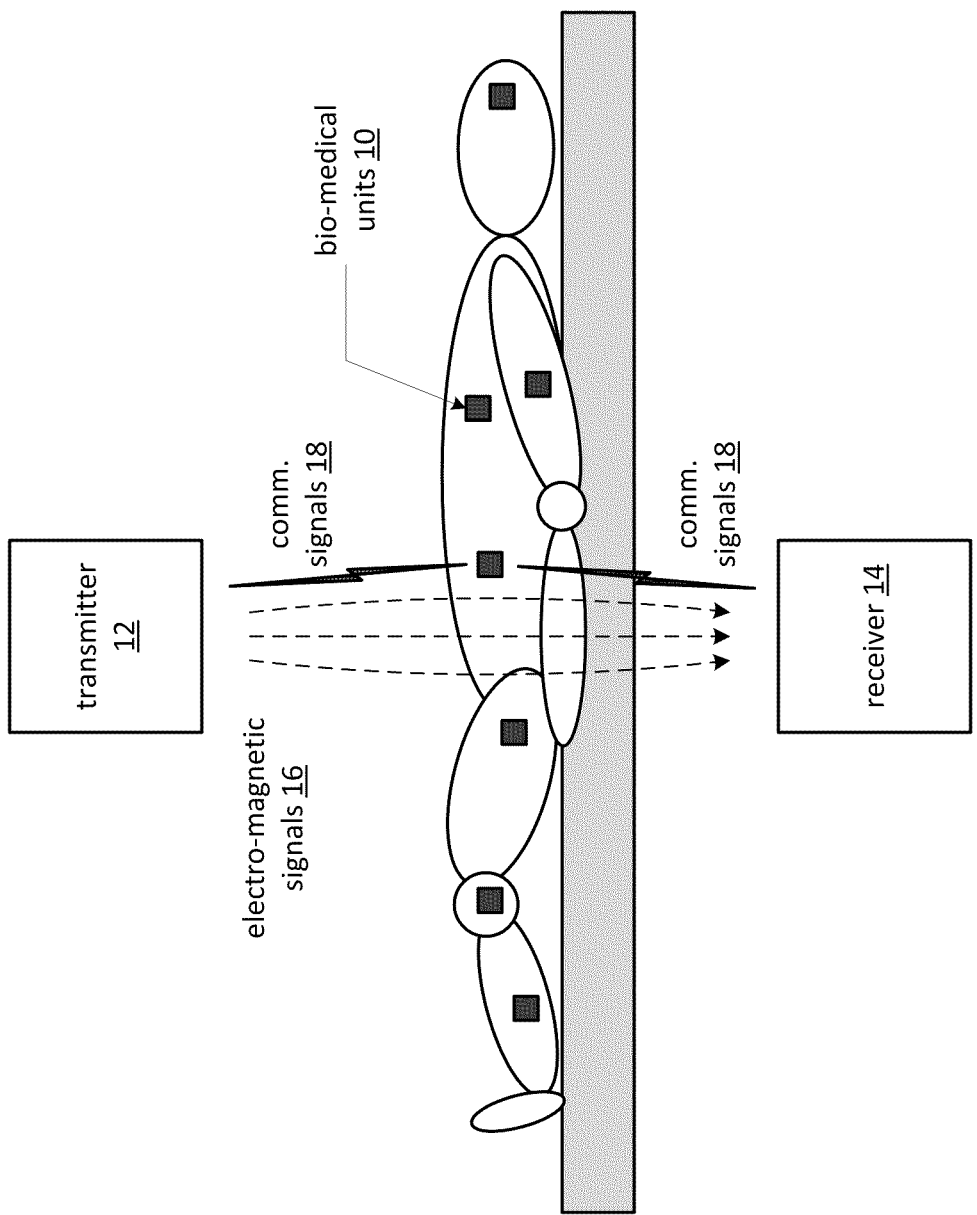
FIG. 1 is a diagram of an embodiment of a system in accordance with the present invention.

FIG. 1 is a diagram of an embodiment of a system that includes a plurality of bio-medical units 10 embedded within a body and/or placed on the surface of the body to facilitate diagnosis, treatment, and/or data collections. Each of the bio-medical units 10 is a passive device (e.g., it does not include a power source (e.g., a battery)) and, as such, includes a power harvesting module. The bio-medical units 10 may also include one or more of memory, a processing module, and functional modules. Alternatively, or in addition to, each of the bio-medical units 10 may include a power source.

In operation, a transmitter emits 12 electromagnetic signals 16 that pass through the body and are received by a receiver 14. The transmitter 12 and receiver 14 may be part of a piece of medical diagnostic equipment (e.g., magnetic resonance imaging (MRI), X-ray, etc.) or independent components for stimulating and communicating with the network of bio-medical units in and/or on a body. One or more of the bio-medical units 10 receives the transmitted electromagnetic signals 16 and generates a supply voltage therefrom. Examples of this will be described in greater detail with reference to FIGS. 8-12.

Embedded within the electromagnetic signals 16 (e.g., radio frequency (RF) signals, millimeter wave (MMW) signals, MRI signals, etc.) or via separate signals, the transmitter 12 communicates with one or more of the bio-medical units 10. For example, the electromagnetic signals 16 may have a frequency in the range of a few MHz to 900 MHz and the communication with the bio-medical units 10 is modulated on the electromagnetic signals 16 at a much higher frequency (e.g., 5 GHz to 300 GHz). As another example, the communication with the bio-medical units 10 may occur during gaps (e.g., per protocol of medical equipment or injected for communication) of transmitting the electromagnetic signals 16. As another example, the communication with the bio-medical units 10 occurs in a different frequency band and/or using a different transmission medium (e.g., use RF or MMW signals when the magnetic field of the electromagnetic signals are dominate, use ultrasound signals when the electromagnetic signals 16 are RF and/or MMW signals, etc.).

One or more of the bio-medical units 10 receives the communication signals 18 and processes them accordingly. The communication signals 18 may be instructions to collect data, to transmit collected data, to move the unit's position in the body, to perform a function, to administer a treatment, etc. If the received communication signals 18 require a response, the bio-medical unit 10 prepares an appropriate response and transmits it to the receiver 14 using a similar communication convention used by the transmitter 12.

Figure 2:
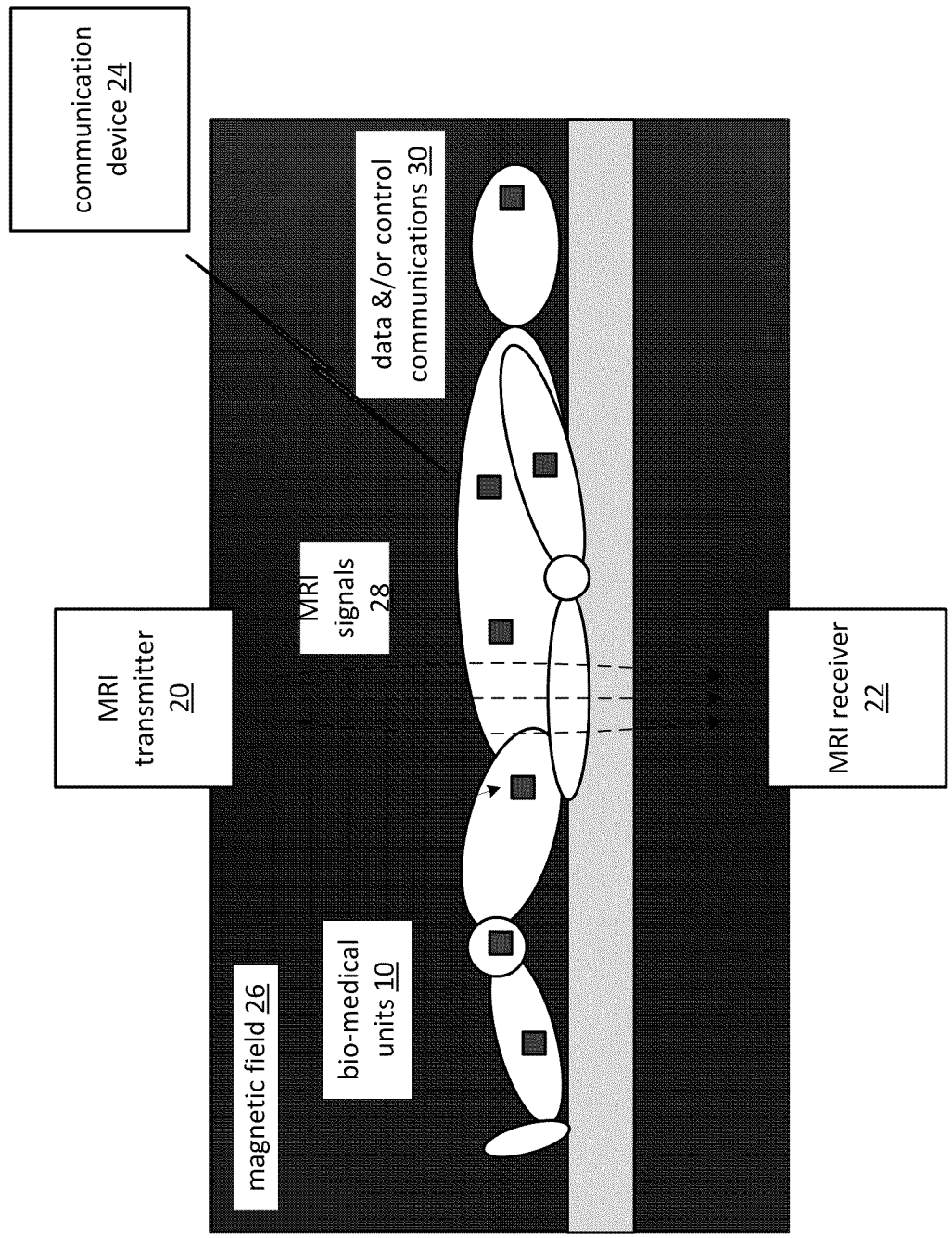
FIG. 2 is a diagram of another embodiment of a system in accordance with the present invention.

FIG. 2 is a diagram of another embodiment of a system that includes a plurality of bio-medical units 10 embedded within a body and/or placed on the surface of the body to facilitate diagnosis, treatment, and/or data collections. Each of the bio-medical units 10 is a passive device and, as such, includes a power harvesting module. The bio-medical units 10 may also include one or more of memory, a processing module, and functional modules. In this embodiment, the person is placed in an MRI machine (fixed or portable) that generates a magnetic field 26 through which the MRI transmitter 20 transmits MRI signals 28 to the MRI receiver 22.

One or more of the bio-medical units 10 powers itself by harvesting energy from the magnetic field 26 or changes thereof as produced by gradient coils, from the magnetic fields of the MRI signals 28, from the electrical fields of the MRI signals 28, and/or from the electromagnetic aspects of the MRI signals 28. A unit 10 converts the harvested energy into a supply voltage that supplies other components of the unit (e.g., a communication module, a processing module, memory, a functional module, etc.).

A communication device 24 communicates data and/or control communications 30 with one or more of the bio-medical units 10 over one or more wireless links. The communication device 24 may be a separate device from the MRI machine or integrated into the MRI machine. For example, the communication device 24, whether integrated or separate, may be a cellular telephone, a computer with a wireless interface (e.g., a WLAN station and/or access point, Bluetooth, a proprietary protocol, etc.), etc. A wireless link may be one or more frequencies in the ISM band, in the 60 GHz frequency band, the ultrasound frequency band, and/or other frequency bands that supports one or more communication protocols (e.g., data modulation schemes, beamforming, RF or MMW modulation, encoding, error correction, etc.).

The composition of the bio-medical units 10 includes non-ferromagnetic materials (e.g., paramagnetic or diamagnetic) and/or metal alloys that are minimally affected by an external magnetic field 26. In this regard, the units harvest power from the MRI signals 28 and communicate using RF and/or MMW electromagnetic signals with negligible chance of encountering the projectile or missile effect of implants that include ferromagnetic materials.

Figure 3:
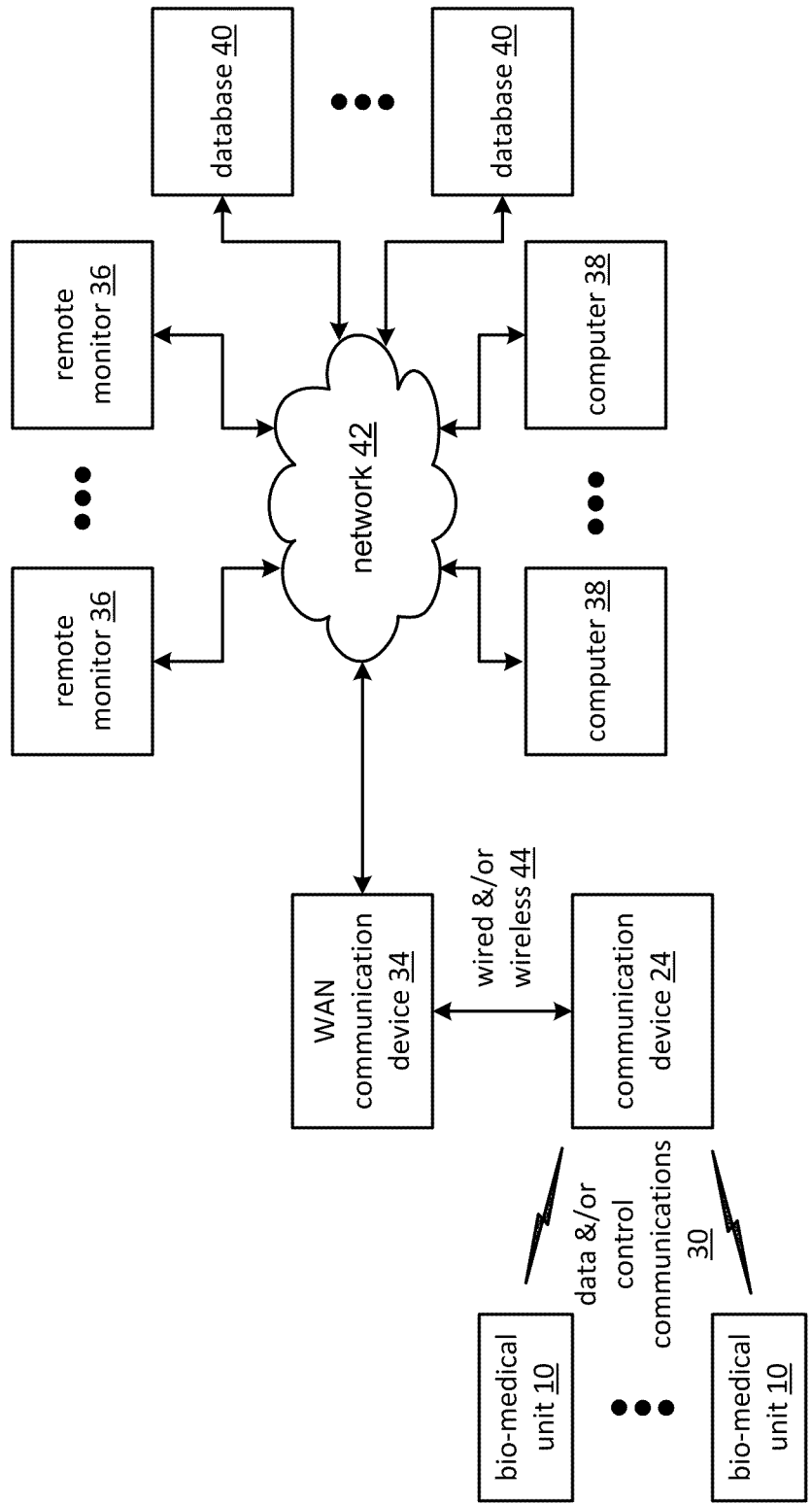
FIG. 3 is a diagram of another embodiment of a system in accordance with the present invention.

FIG. 3 is a diagram of another embodiment of a system that includes a plurality of bio-medical units 10 and one or more communication devices 24 coupled to a wide area network (WAN) communication device 34 (e.g., a cable modem, DSL modem, base station, access point, hot spot, etc.). The WAN communication device 34 is coupled to a network 42 (e.g., cellular telephone network, internet, etc.), which has coupled to it a plurality of remote monitors 36, a plurality of databases 40, and a plurality of computers 38.

In an example of operation, one or more of the remote monitors 36 may receive images and/or other data 30 from one or more of the bio-medical units 10 via the communication device 24, the WAN communication device 34, and the network 42. In this manner, a person(s) operating the remote monitors 36 may view images and/or the data 30 gathered by the bio-medical units 10. This enables a specialist to be consulted without requiring the patient to travel to the specialist's office.

In another example of operation, one or more of the computers 38 may communicate with the bio-medical units 10 via the communication device 24, the WAN communication device 34, and the network 42. In this example, the computer 36 may provide commands 30 to one or more of the bio-medical units 10 to gather data, to dispense a medication, to move to a new position in the body, to perform a mechanical function (e.g., cut, grasp, drill, puncture, stitch, patch, etc.), etc. As such, the bio-medical units 10 may be remotely controlled via one or more of the computers 36.

In another example of operation, one or more of the bio-medical units 10 may read and/or write data from or to one or more of the databases 40. For example, data (e.g., a blood sample analysis) generated by one or more of the bio-medical units 10 may be written to one of the databases 40. The communication device 24 and/or one of the computers 36 may control the writing of data to or the reading of data from the database(s) 40. The data may further include medical records, medical images, prescriptions, etc.

Figure 4:
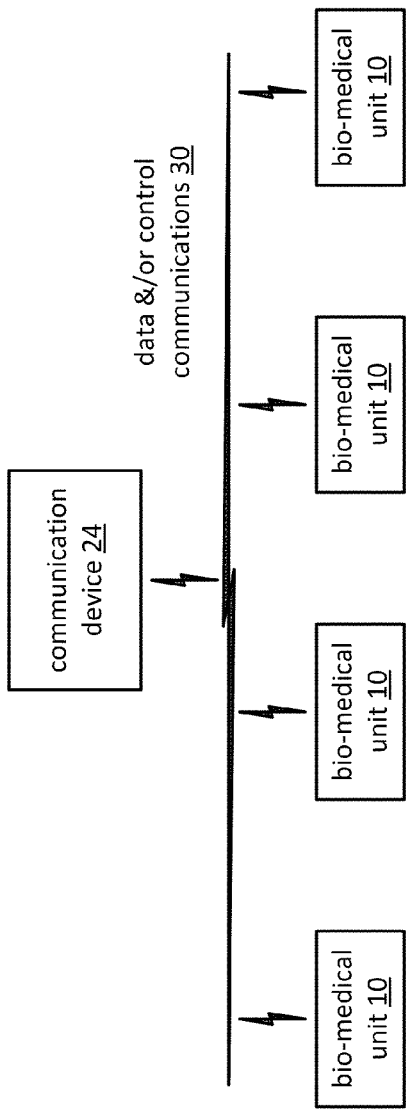
FIG. 4 is a diagram of another embodiment of a system in accordance with the present invention.

FIG. 4 is a diagram of another embodiment of a system that includes a plurality of bio-medical units 10. In this embodiment, the bio-medical units 10 can communicate with each other directly and/or communicate with the communication device 24 directly. The communication medium may be an infrared channel(s), an RF channel(s), a MMW channel(s), and/or ultrasound. The units may use a communication protocol such as token passing, carrier sense, time division multiplexing, code division multiplexing, frequency division multiplexing, etc.

Figure 5:
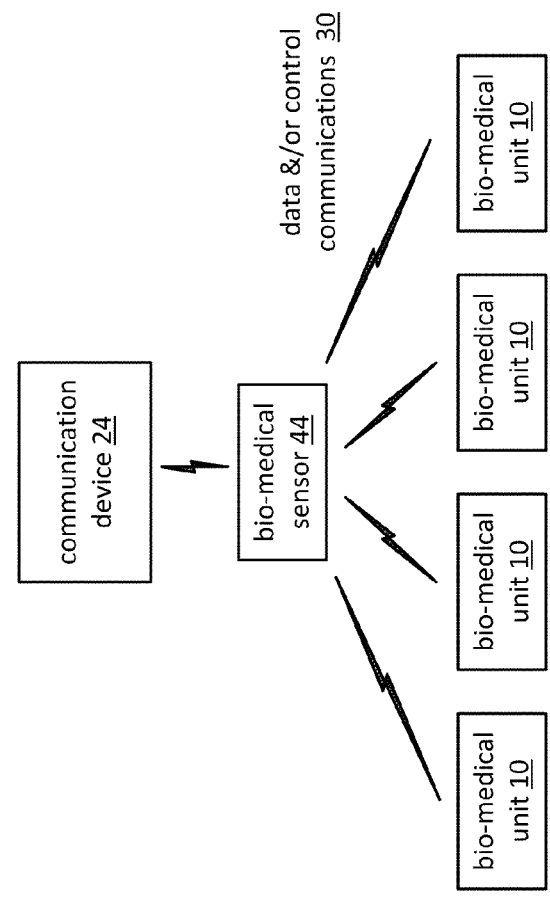
FIG. 5 is a diagram of another embodiment of a system in accordance with the present invention.

FIG. 5 is a diagram of another embodiment of a system that includes a plurality of bio-medical units 10. In this embodiment, one of the bio-medical units 44 functions as an access point for the other units. As such, the designated unit 44 routes communications between the units 10 and between one or more units 10 and the communication device 24. The communication medium may be an infrared channel(s), an RF channel(s), a MMW channel(s), and/or ultrasound. The units 10 may use a communication protocol such as token passing, carrier sense, time division multiplexing, code division multiplexing, frequency division multiplexing, etc.

Figure 6:
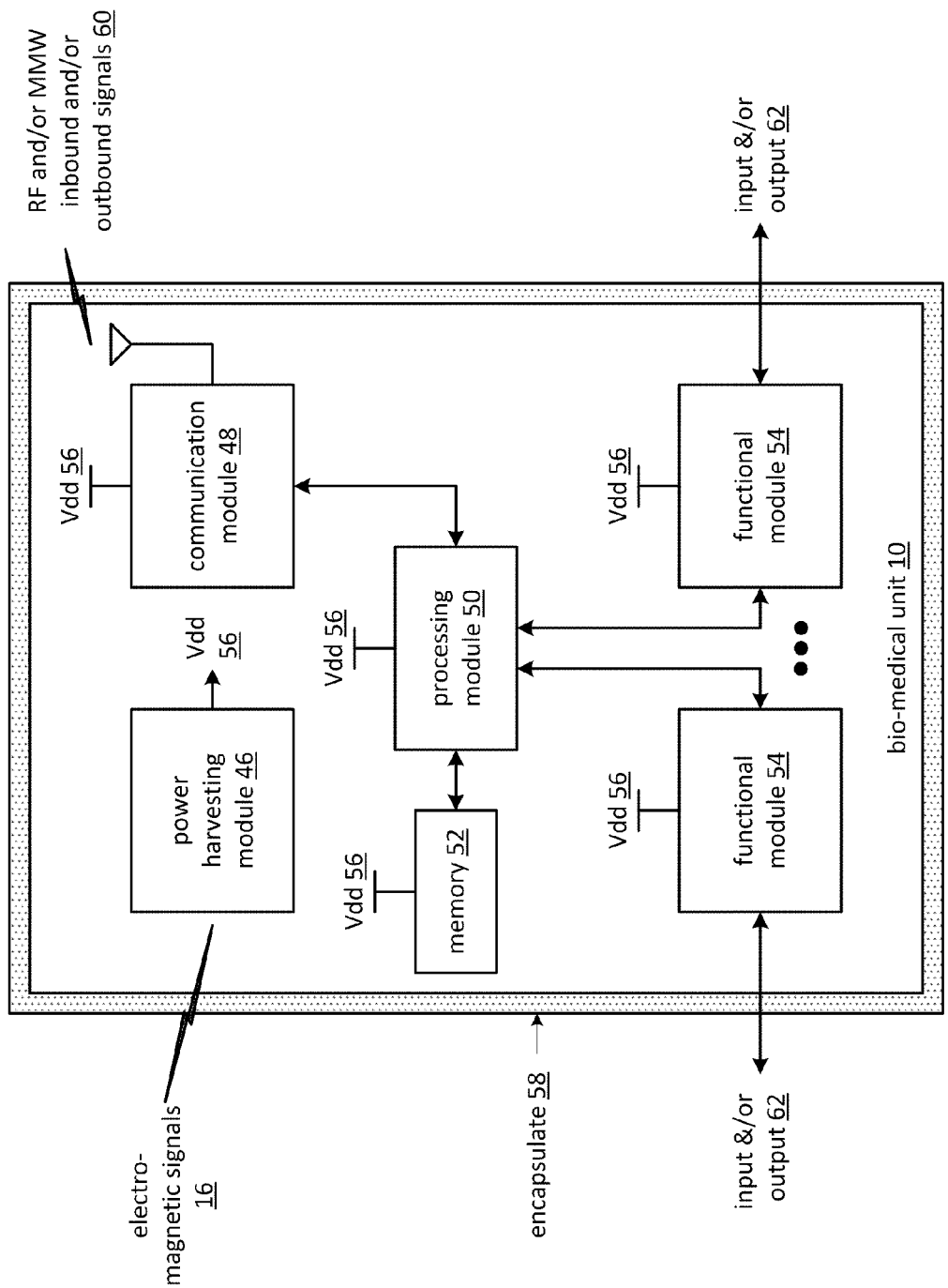
FIG. 6 is a schematic block diagram of an embodiment of a bio-medical unit in accordance with the present invention.

FIG. 6 is a schematic block diagram of an embodiment of a bio-medical unit 10 that includes a power harvesting module 46, a communication module 48, a processing module 50, memory 52, and one or more functional modules 54. The processing module 50 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module 50 may have an associated memory 52 and/or memory element, which may be a single memory device, a plurality of memory devices, and/or embedded circuitry of the processing module. Such a memory device 52 may be a read-only memory, random access memory, volatile memory, non-volatile memory, static memory, dynamic memory, flash memory, cache memory, and/or any device that stores digital information. Note that if the processing module 50 includes more than one processing device, the processing devices may be centrally located (e.g., directly coupled together via a wired and/or wireless bus structure) or may be distributedly located (e.g., cloud computing via indirect coupling via a local area network and/or a wide area network). Further note that when the processing module 50 implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element stores, and the processing module executes, hard coded and/or operational instructions corresponding to at least some of the steps and/or functions illustrated in FIGS. 1-41.

The power harvesting module 46 may generate one or more supply voltages 56 (Vdd) from one or more of MRI electromagnetic signals 16, magnetic fields 26, RF signals, MMW signals, and body motion. The power harvesting module 46 may be implemented as disclosed in U.S. Pat. No. 7,595,732 to generate one or more supply voltages from an RF signal. The power harvesting module 46 may be implemented as shown in one or more FIGS. 9-11 to generate one or more supply voltages 56 from an MRI signal 28 and/or magnetic field 26. The power harvesting module 46 may be implemented as shown in FIG. 12 to generate one or more supply voltage 56 from body motion.

The communication module 48 may include a receiver section and a transmitter section. The transmitter section converts an outbound symbol stream into an outbound RF or MMW signal 60 that has a carrier frequency within a given frequency band (e.g., 900 MHz, 2.5 GHz, 5 GHz, 57-66 GHz, etc.). In an embodiment, this may be done by mixing the outbound symbol stream with a local oscillation to produce an up-converted signal. One or more power amplifiers and/or power amplifier drivers amplifies the up-converted signal, which may be RF or MMW bandpass filtered, to produce the outbound RF or MMW signal 60. In another embodiment, the transmitter section includes an oscillator that produces an oscillation. The outbound symbol stream provides phase information (e.g., +/− Δθ [phase shift] and/or θ(t) [phase modulation]) that adjusts the phase of the oscillation to produce a phase adjusted RF or MMW signal, which is transmitted as the outbound RF signal 60. In another embodiment, the outbound symbol stream includes amplitude information (e.g., A(t) [amplitude modulation]), which is used to adjust the amplitude of the phase adjusted RF or MMW signal to produce the outbound RF or MMW signal 60.

In yet another embodiment, the transmitter section includes an oscillator that produces an oscillation. The outbound symbol provides frequency information (e.g., +/− Δf [frequency shift] and/or f(t) [frequency modulation]) that adjusts the frequency of the oscillation to produce a frequency adjusted RF or MMW signal, which is transmitted as the outbound RF or MMW signal 60. In another embodiment, the outbound symbol stream includes amplitude information, which is used to adjust the amplitude of the frequency adjusted RF or MMW signal to produce the outbound RF or MMW signal 60. In a further embodiment, the transmitter section includes an oscillator that produces an oscillation. The outbound symbol provides amplitude information (e.g., +/− ΔA [amplitude shift] and/or A(t) [amplitude modulation] that adjusts the amplitude of the oscillation to produce the outbound RF or MMW signal 60.

The receiver section amplifies an inbound RF or MMW signal 60 to produce an amplified inbound RF or MMW signal. The receiver section may then mix in-phase (I) and quadrature (Q) components of the amplified inbound RF or MMW signal with in-phase and quadrature components of a local oscillation to produce a mixed I signal and a mixed Q signal. The mixed I and Q signals are combined to produce an inbound symbol stream. In this embodiment, the inbound symbol may include phase information (e.g., +/− Δθ [phase shift] and/or θ(t) [phase modulation]) and/or frequency information (e.g., +/− Δf [frequency shift] and/or f(t) [frequency modulation]). In another embodiment and/or in furtherance of the preceding embodiment, the inbound RF or MMW signal includes amplitude information (e.g., +/− ΔA [amplitude shift] and/or A(t) [amplitude modulation]). To recover the amplitude information, the receiver section includes an amplitude detector such as an envelope detector, a low pass filter, etc.

The processing module 50 generates the outbound symbol stream from outbound data and converts the inbound symbol stream into inbound data. For example, the processing module 50 converts the inbound symbol stream into inbound data (e.g., voice, text, audio, video, graphics, etc.) in accordance with one or more wireless communication standards (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.). Such a conversion may include one or more of: digital intermediate frequency to baseband conversion, time to frequency domain conversion, space-time-block decoding, space-frequency-block decoding, demodulation, frequency spread decoding, frequency hopping decoding, beamforming decoding, constellation demapping, deinterleaving, decoding, depuncturing, and/or descrambling.

As another example, the processing module 50 converts outbound data (e.g., voice, text, audio, video, graphics, etc.) into outbound symbol stream in accordance with one or more wireless communication standards (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.). Such a conversion includes one or more of: scrambling, puncturing, encoding, interleaving, constellation mapping, modulation, frequency spreading, frequency hopping, beamforming, space-time-block encoding, space-frequency-block encoding, frequency to time domain conversion, and/or digital baseband to intermediate frequency conversion.

Each of the one or more functional modules 54 provides a function to support treatment, data gathering, motion, repairs, and/or diagnostics. The functional modules 54 may be implemented using nanotechnology and/or microelectronic mechanical systems (MEMS) technology. Various examples of functional modules 54 are illustrated in one or more of FIGS. 1-41.

The bio-medical unit 10 may be encapsulated by an encapsulate 58 that is non-toxic to the body. For example, the encapsulate 58 may be a silicon based product, a non-ferromagnetic metal alloy (e.g., stainless steel), etc. As another example, the encapsulate 58 may include a spherical shape and have a ferromagnetic liner that shields the unit from a magnetic field and to offset the forces of the magnetic field.

The bio-medical unit 10 may be implemented on a single die that has an area of a few millimeters or less. The die may be fabricated in accordance with CMOS technology, Gallium-Arsenide technology, and/or any other integrated circuit die fabrication process.

Figure 7:
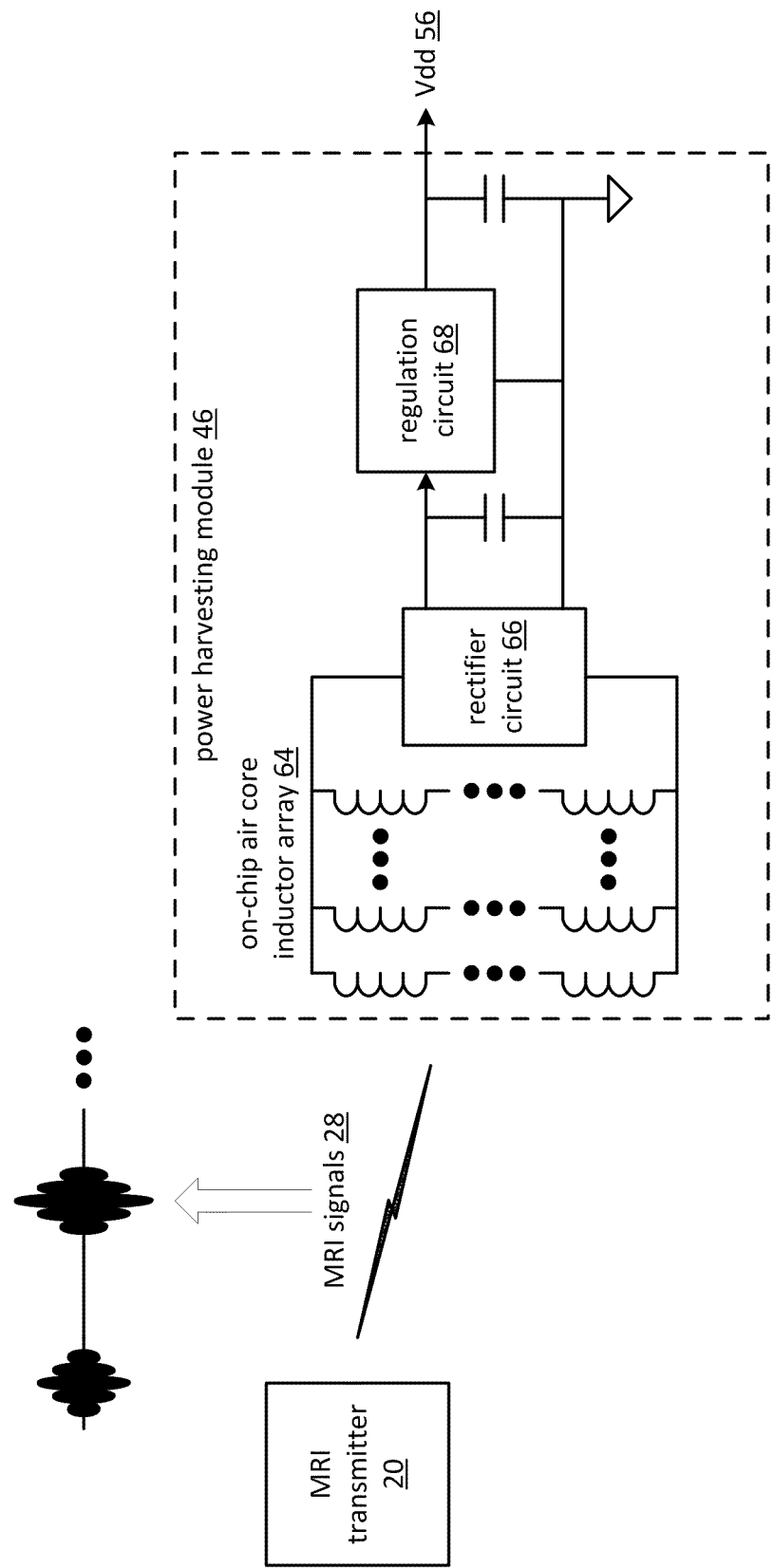
FIG. 7 is a schematic block diagram of an embodiment of a power harvesting module in accordance with the present invention.

FIG. 7 is a schematic block diagram of an embodiment of a power harvesting module 46 that includes an array of on-chip air core inductors 64, a rectifying circuit 66, capacitors, and a regulation circuit 68. The inductors 64 may each having an inductance of a few nano-Henries to a few micro-Henries and may be coupled in series, in parallel, or a series parallel combination.

In an example of operation, the MRI transmitter 20 transmits MRI signals 28 at a frequency of 3-45 MHz at a power level of up to 35 KWatts. The air core inductors 64 are electromagnetically coupled to generate a voltage from the magnetic and/or electric field generated by the MRI signals 28. Alternatively or in addition to, the air core inductors 64 may generate a voltage from the magnetic field 26 and changes thereof produced by the gradient coils. The rectifying circuit 66 rectifies the AC voltage produced by the inductors to produce a first DC voltage. The regulation circuit generates one or more desired supply voltages 56 from the first DC voltage.

The inductors 64 may be implemented on one more metal layers of the die and include one or more turns per layer. Note that trace thickness, trace length, and other physical properties affect the resulting inductance.

Figure 8:
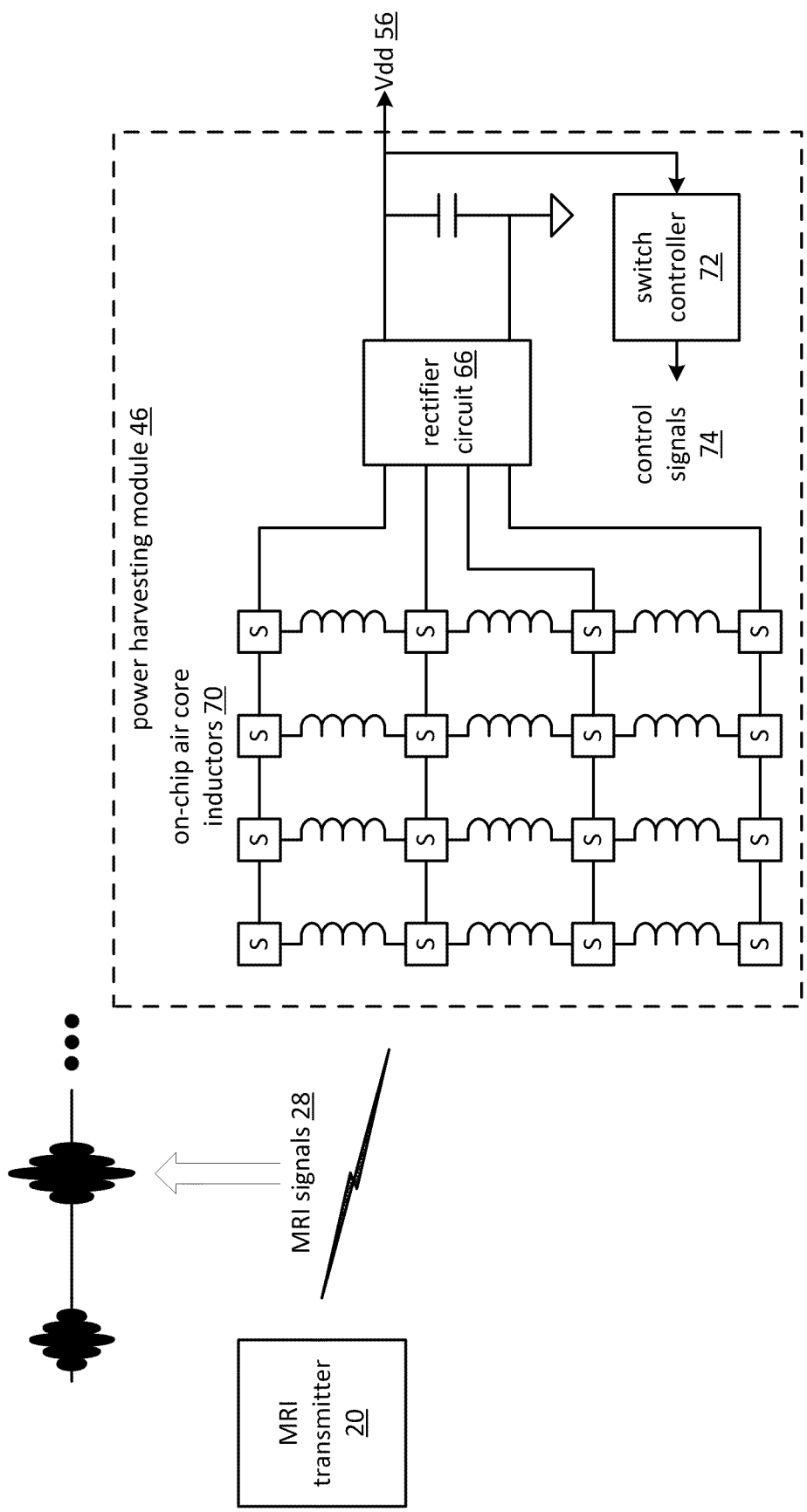
FIG. 8 is a schematic block diagram of another embodiment of a power harvesting module in accordance with the present invention.

FIG. 8 is a schematic block diagram of another embodiment of a power harvesting module 46 that includes a plurality of on-chip air core inductors 70, a plurality of switching units (S), a rectifying circuit 66, a capacitor, and a switch controller 72. The inductors 70 may each having an inductance of a few nano-Henries to a few micro-Henries and may be coupled in series, in parallel, or a series parallel combination.

In an example of operation, the MRI transmitter 20 transmits MRI signals 28 at a frequency of 3-45 MHz at a power level of up to 35 KWatts. The air core inductors 70 are electromagnetically coupled to generate a voltage from the magnetic and/or electric field generated by the MRI signals 28. The switching module 72 engages the switches via control signals 74 to couple the inductors 70 in series and/or parallel to generate a desired AC voltage. The rectifier circuit 66 and the capacitor(s) convert the desired AC voltage into the one or more supply voltages 56.

Figure 9:
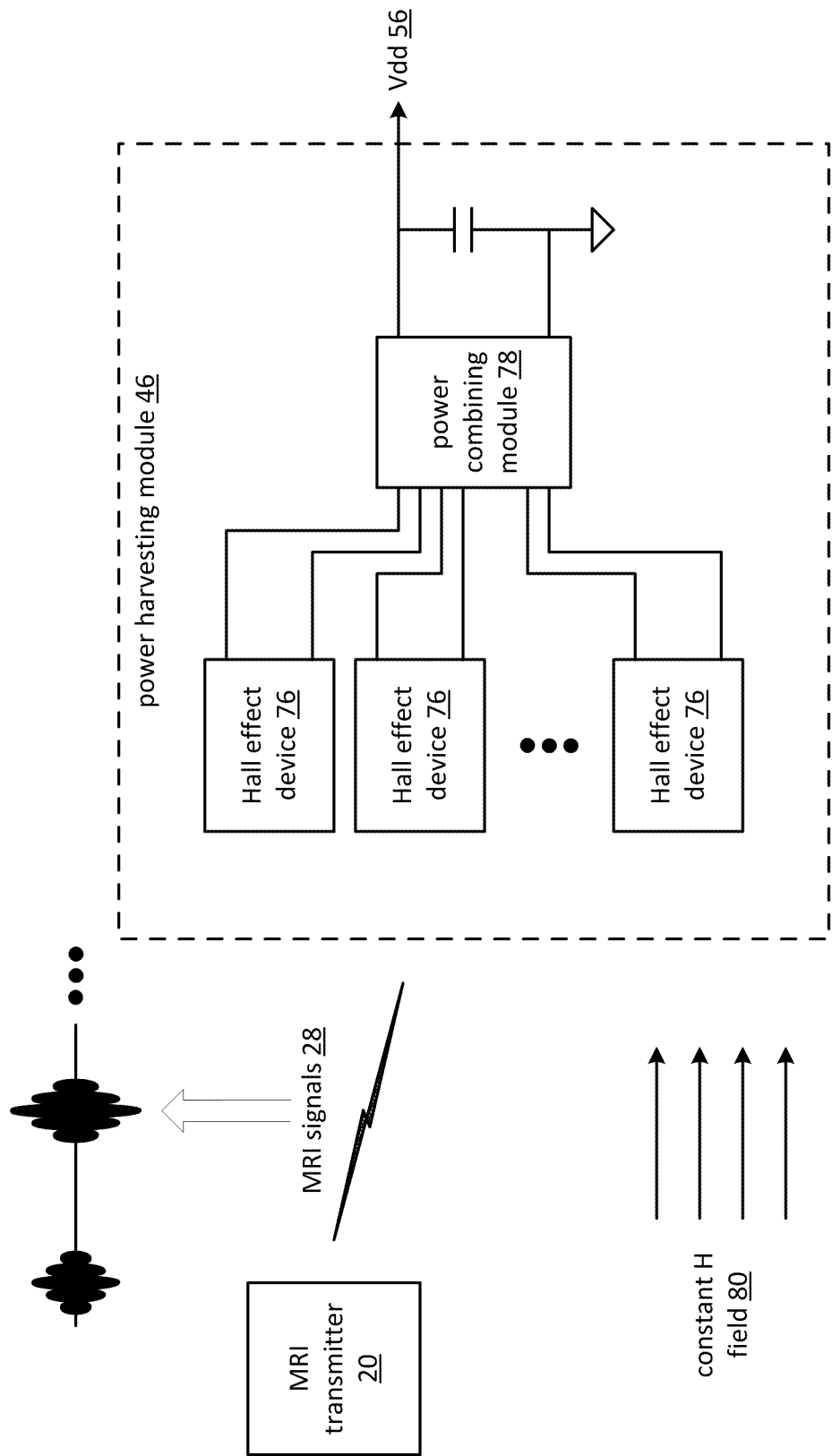
FIG. 9 is a schematic block diagram of another embodiment of a power harvesting module in accordance with the present invention.

FIG. 9 is a schematic block diagram of another embodiment of a power harvesting module 46 that includes a plurality of Hall effect devices 76, a power combining module 78, and a capacitor(s). In an example of operation, the Hall effect devices 76 generate a voltage based on the constant magnetic field (H) and/or a varying magnetic field. The power combining module 78 (e.g., a wire, a switch network, a transistor network, a diode network, etc.) combines the voltages of the Hall effect devices 76 to produce the one or more supply voltages 56.

Figure 10:
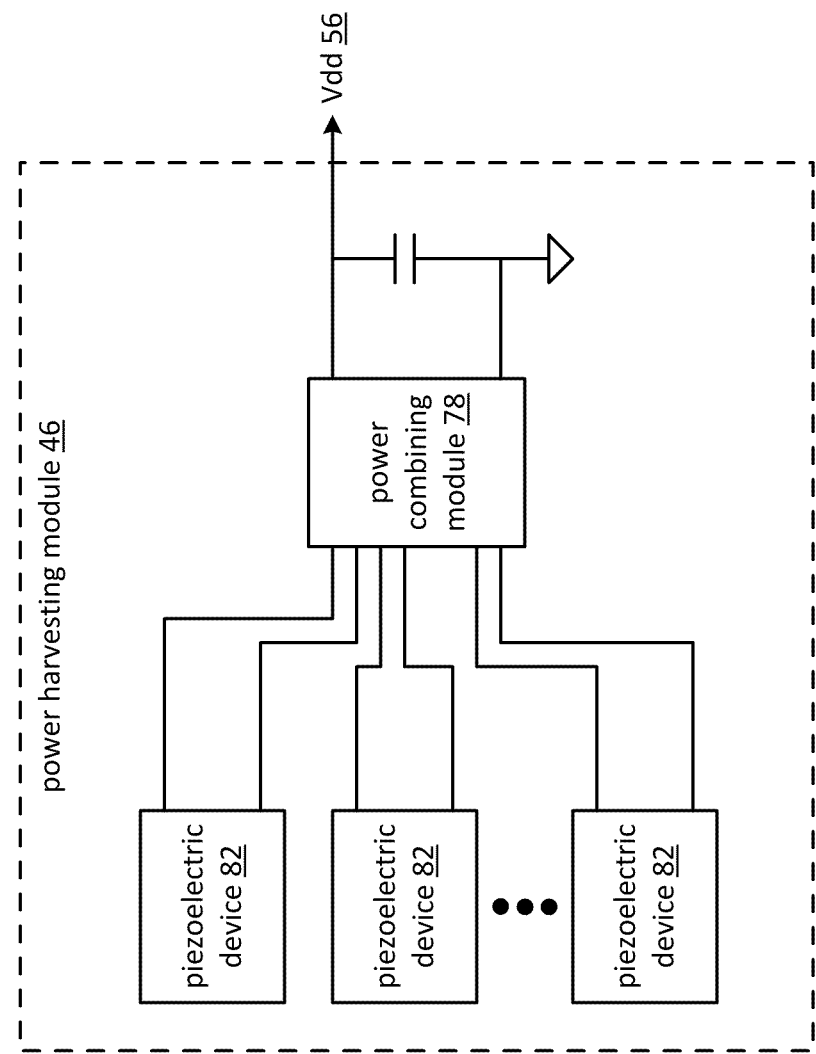
FIG. 10 is a schematic block diagram of another embodiment of a power harvesting module in accordance with the present invention.

FIG. 10 is a schematic block diagram of another embodiment of a power harvesting module 46 that includes a plurality of piezoelectric devices 82, a power combining module 78, and a capacitor(s). In an example of operation, the piezoelectric devices 82 generate a voltage based on body movement, ultrasound signals, movement of body fluids, etc. The power combining module 78 (e.g., a wire, a switch network, a transistor network, a diode network, etc.) combines the voltages of the Hall effect devices 82 to produce the one or more supply voltages 56. Note that the piezoelectric devices 82 may include one or more of a piezoelectric motor, a piezoelectric actuator, a piezoelectric sensor, and/or a piezoelectric high voltage device.

The various embodiments of the power harvesting module 46 may be combined to generate more power, more supply voltages, etc. For example, the embodiment of FIG. 9 may be combined with one or more of the embodiments of FIGS. 8 and 9.

Figure 11:
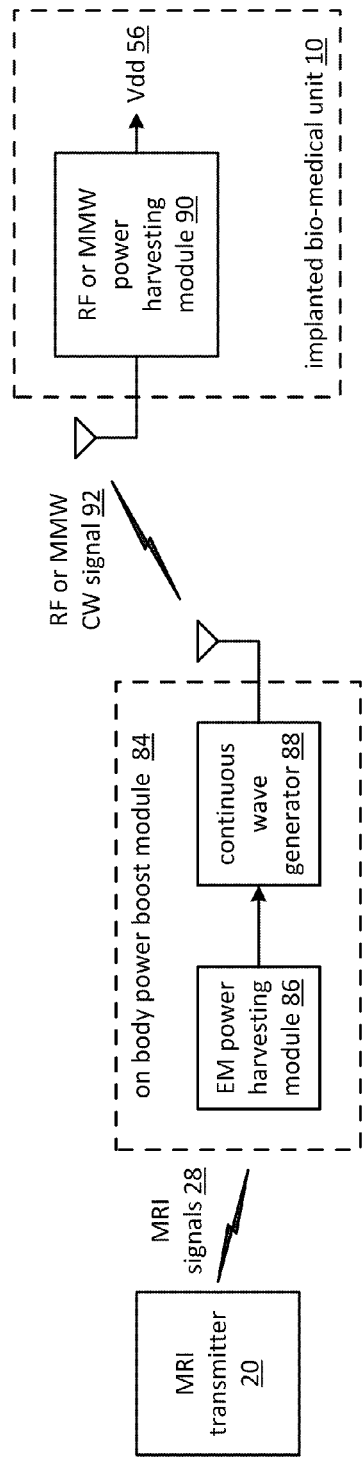
FIG. 11 is a schematic block diagram of an embodiment of a power boost module in accordance with the present invention.
Figure 12:
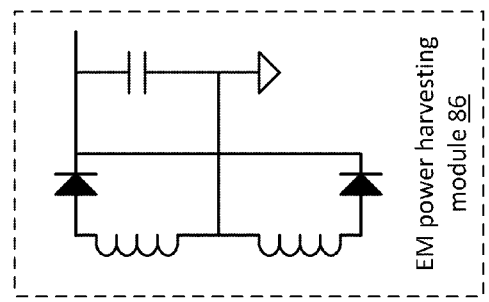
FIG. 12 is a schematic block diagram of an embodiment of an electromagnetic (EM)) power harvesting module in accordance with the present invention.

FIG. 11 is a schematic block diagram of an embodiment of a power boost module 84 that harvests energy from MRI signals 28 and converts the energy into continuous wave (CW) RF (e.g., up to 3 GHz) and/or MMW (e.g., up to 300 GHz) signals 92 to provide power to the implanted bio-medical units 10. The power boost module 84 sits on the body of the person under test or treatment and includes an electromagnetic power harvesting module 86 and a continuous wave generator 88. In such an embodiment, the power boosting module 84 can recover significantly more energy than a bio-medical unit 10 since it can be significantly larger. For example, a bio-medical unit 10 may have an area of a few millimeters squared while the power boosting module 84 may have an area of a few to tens of centimeters squared.

FIG. 12 is a schematic block diagram of an embodiment of an electromagnetic (EM)) power harvesting module 86 that includes inductors, diodes (or transistors) and a capacitor. The inductors may each be a few mili-Henries such that the power boost module can deliver up to 10's of mili-watts of power.

Figure 13:
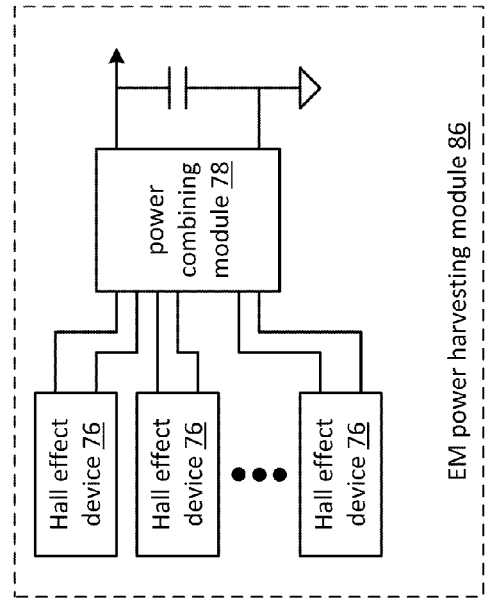
FIG. 13 is a schematic block diagram of another embodiment of an electromagnetic (EM)) power harvesting module in accordance with the present invention.

FIG. 13 is a schematic block diagram of another embodiment of an electromagnetic (EM)) power harvesting module 86 that includes a plurality of Hall effect devices 76, a power combining module 78, and a capacitor. This functions as described with reference to FIG. 11, but the Hall effect devices 76 can be larger such that more power can be produced. Note that the EM power harvesting module 86 may include a combination of the embodiment of FIG. 14 and the embodiment of FIG. 15.

Figure 14:
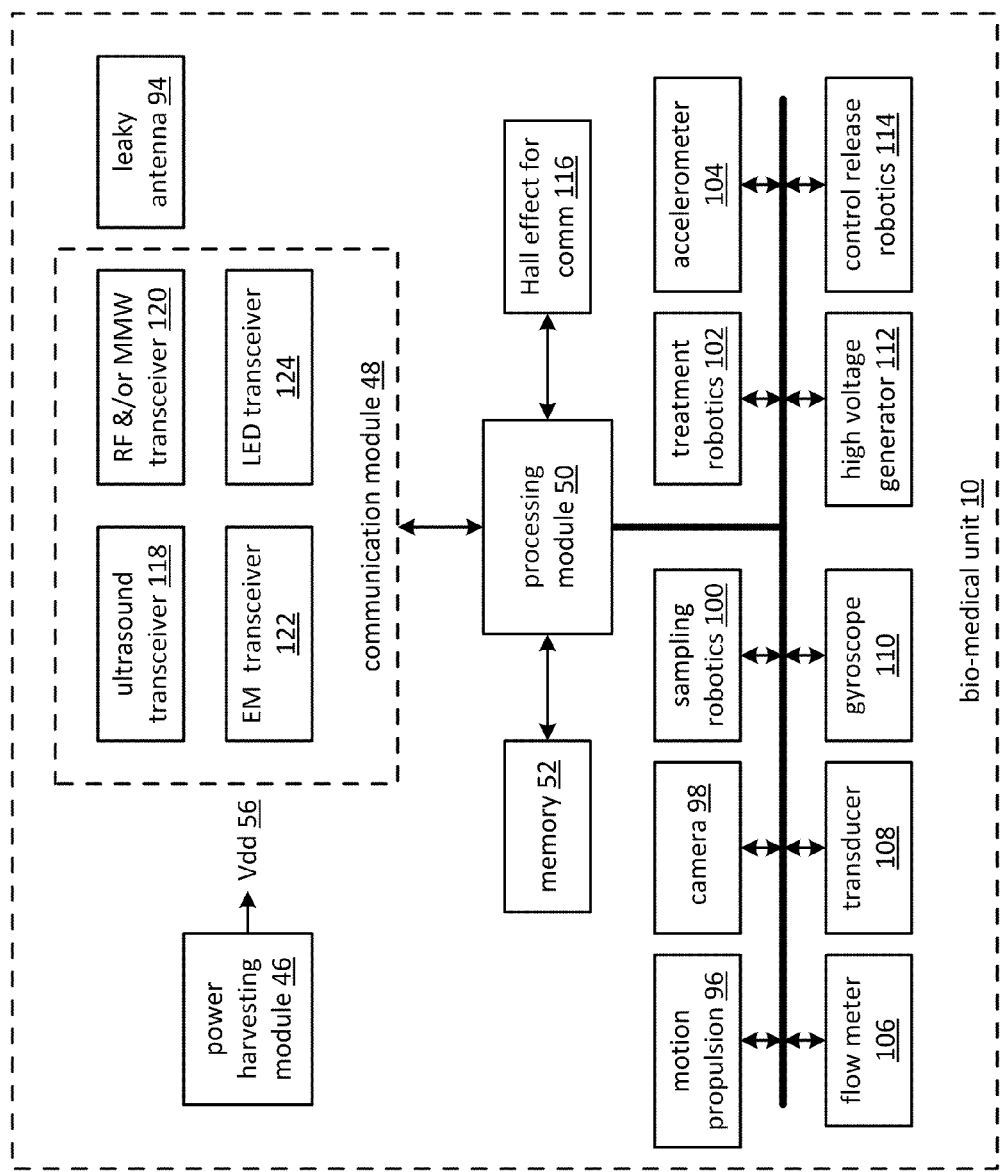
FIG. 14 is a schematic block diagram of another embodiment of a bio-medical unit in accordance with the present invention.

FIG. 14 is a schematic block diagram of another embodiment of a bio-medical unit 10 that includes a power harvesting module 46, a communication module 48, a processing module 50, memory 52, and may include one or more functional modules 54 and/or a Hall effect communication module 116. The communication module 48 may include one or more of an ultrasound transceiver 118, an electromagnetic transceiver 122, an RF and/or MMW transceiver 120, and a light source (LED) transceiver 124. Note that examples of the various types of communication modules 48 will be described in greater detail with reference to one or more of FIGS. 14-49.

The one or more functional modules 54 may perform a repair function, an imaging function, and/or a leakage detection function, which may utilize one or more of a motion propulsion module 96, a camera module 98, a sampling robotics module 100, a treatment robotics module 102, an accelerometer module 104, a flow meter module 106, a transducer module 108, a gyroscope module 110, a high voltage generator module 112, a control release robotics module 114, and/or other functional modules described with reference to one or more other figures. The functional modules 54 may be implemented using MEMS technology and/or nanotechnology. For example, the camera module 98 may be implemented as a digital image sensor in MEMS technology. Example of these various modules will be described in greater detail with reference to one or more of FIGS. 14-49.

The Hall effect communication module 116 utilizes variations in the magnetic field and/or electrical field to produce a plus or minus voltage, which can be encoded to convey information. For example, the charge applied to one or more Hall effect devices 76 may be varied to produce the voltage change. As another example, an MRI transmitter 20 and/or gradient unit may modulate a signal on the magnetic field 26 it generates to produce variations in the magnetic field 26.

Figure 15:
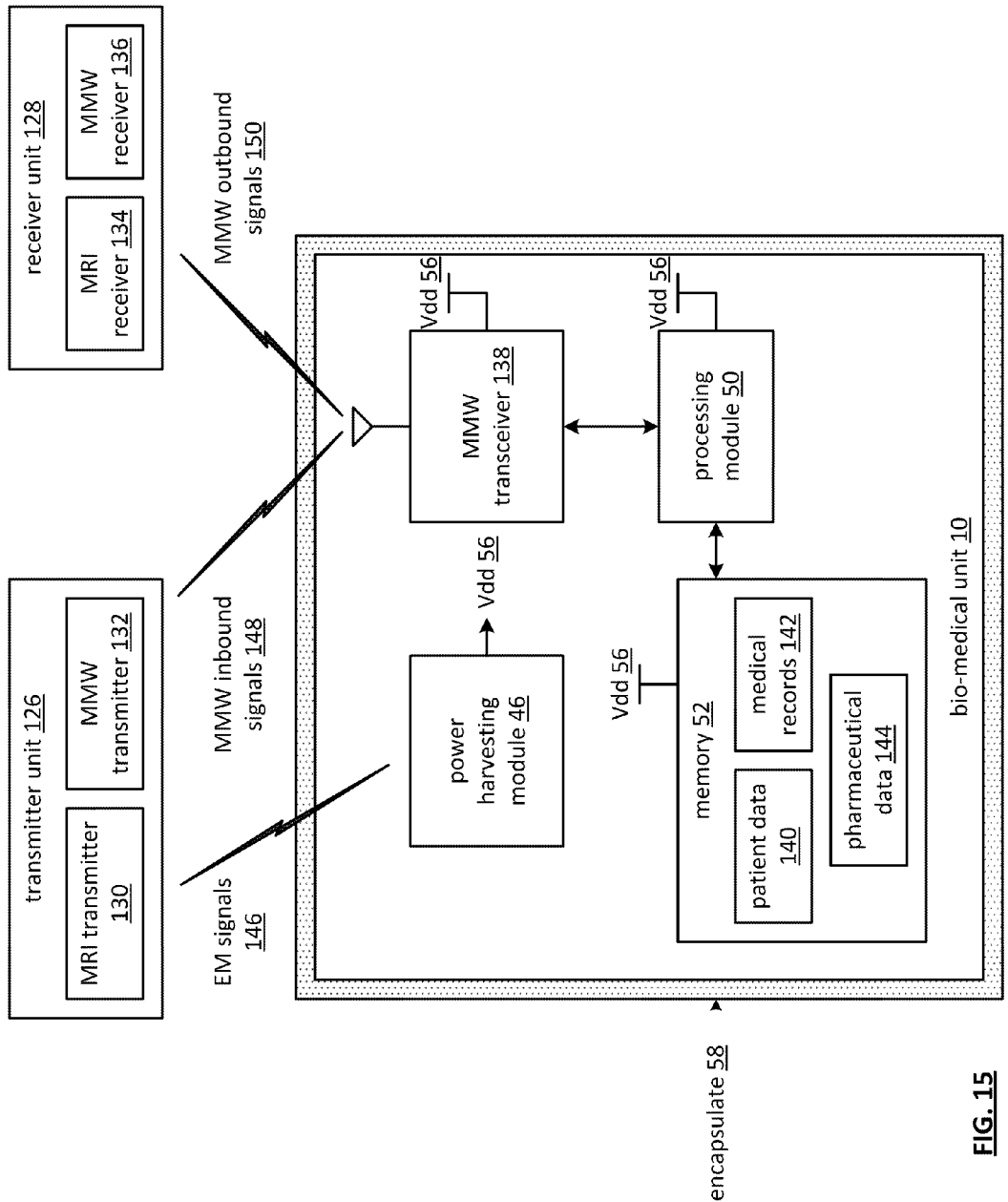
FIG. 15 is a diagram of another embodiment of a system in accordance with the present invention.

FIG. 15 is a diagram of another embodiment of a system that includes one or more bio-medical units 10, a transmitter unit 126, and a receiver unit 128. Each of the bio-medical units 10 includes a power harvesting module 46, a MMW transceiver 138, a processing module 50, and memory 52. The transmitter unit 126 includes a MRI transmitter 130 and a MMW transmitter 132. The receiver unit 128 includes a MRI receiver 134 and a MMW receiver 136. Note that the MMW transmitter 132 and MMW receiver 136 may be in the same unit (e.g., in the transmitter unit, in the receiver unit, or housed in a separate device).

In an example of operation, the bio-medical unit 10 recovers power from the electromagnetic (EM) signals 146 transmitted by the MRI transmitter 130 and communicates via MMW signals 148-150 with the MMW transmitter 132 and MMW receiver 136. The MRI transmitter 130 may be part of a portable MRI device, may be part of a full sized MRI machine, and/or part of a separate device for generating EM signals 146 for powering the bio-medical unit 10.

Figure 16:
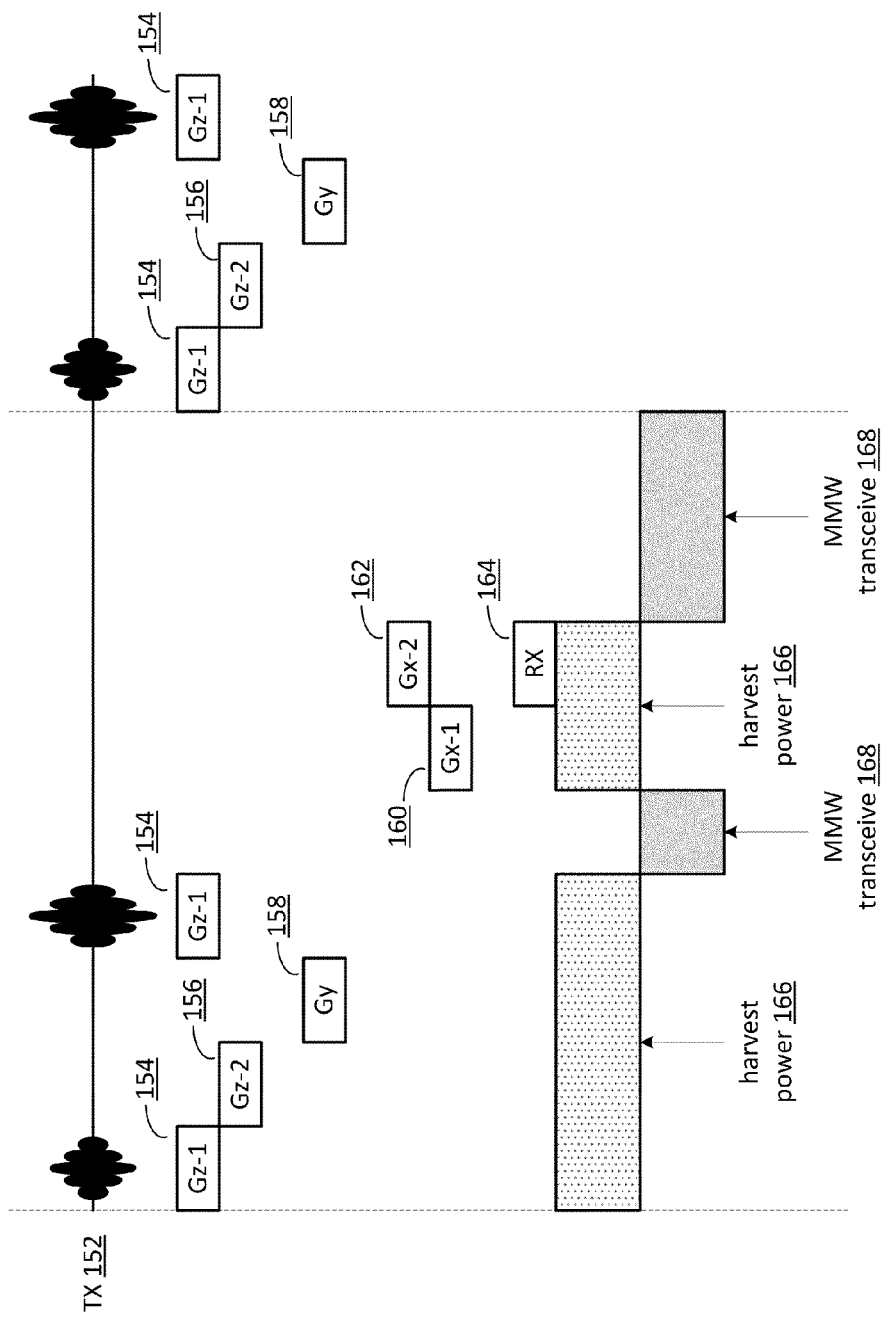
FIG. 16 is a diagram of an example of a communication protocol within a system in accordance with the present invention.

FIG. 16 is a diagram of an example of a communication protocol within the system of FIG. 15. In this diagram, the MRI transmitter 20 transmits RF signals 152, which have a frequency in the range of 3-45 MHz, at various intervals with varying signal strengths. The power harvesting module 46 of the bio-medical units 10 may use these signals to generate power for the bio-medical unit 10.

In addition to the MRI transmitter 20 transmitting its signal, a constant magnetic field and various gradient magnetic fields 154-164 are created (one or more in the x dimension Gx, one or more in the y dimension Gy, and one or more in the z direction Gz). The power harvesting module 46 of the bio-medical unit 10 may further use the constant magnetic field and/or the varying magnetic fields 154-164 to create power for the bio-medical unit 10.

During non-transmission periods of the cycle, the bio-medical unit 10 may communicate 168 with the MMW transmitter 132 and/or MMW receiver 136. In this regard, the bio-medical unit 10 alternates from generating power to MMW communication in accordance with the conventional transmission-magnetic field pattern of an MRI machine.

Figure 17:
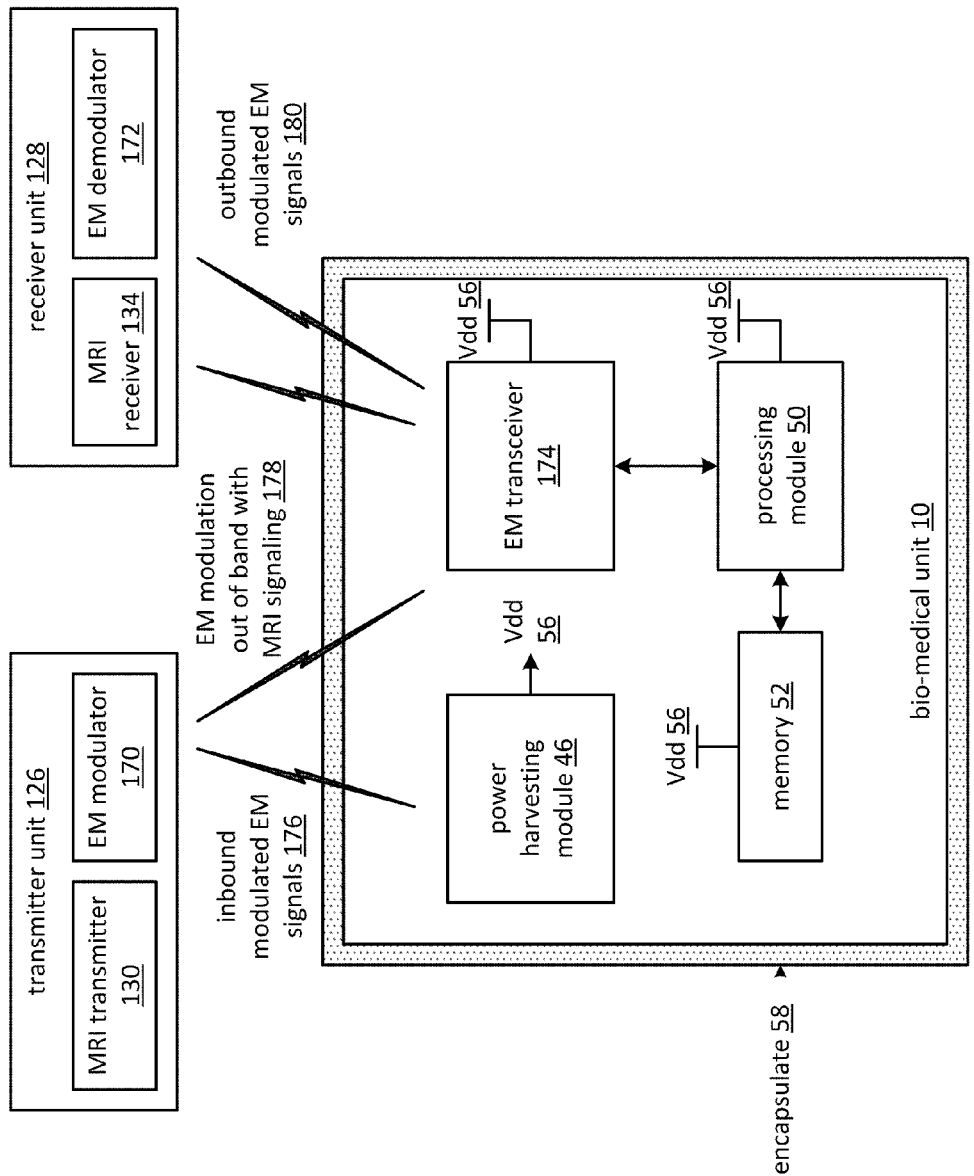
FIG. 17 is a diagram of another embodiment of a system in accordance with the present invention.

FIG. 17 is a diagram of another embodiment of a system includes one or more bio-medical units 10, a transmitter unit 126, and a receiver unit 128. Each of the bio-medical units 10 includes a power harvesting module 46, an EM transceiver 174, a processing module 50, and memory 52. The transmitter unit 126 includes a MRI transmitter 130 and electromagnetic (EM) modulator 170. The receiver unit 128 includes a MRI receiver 134 and a EM demodulator 172. The transmitter unit 126 and receiver unit 128 may be part of a portable MRI device, may be part of a full sized MRI machine, or part of a separate device for generating EM signals for powering the bio-medical unit 10.

In an example of operation, the MRI transmitter 130 generates an electromagnetic signal that is received by the EM modulator 170. The EM modulator 170 modulates a communication signal on the EM signal to produce an inbound modulated EM signal 176. The EM modulator 170 may modulate (e.g., amplitude modulation, frequency modulation, amplitude shift keying, frequency shift keying, etc.) the magnetic field and/or electric field of the EM signal. In another embodiment, the EM modulator 170 may modulate the magnetic fields produced by the gradient coils to produce the inbound modulated EM signals 176.

The bio-medical unit 10 recovers power from the modulated electromagnetic (EM) signals. In addition, the EM transceiver 174 demodulates the modulated EM signals 178 to recover the communication signal. For outbound signals, the EM transceiver 174 modulates an outbound communication signal to produce outbound modulated EM signals 180. In this instance, the EM transceiver 174 is generating an EM signal that, in air, is modulated on the EM signal transmitted by the transmitter unit 126. In one embodiment, the communication in this system is half duplex such that the modulation of the inbound and outbound communication signals is at the same frequency. In another embodiment, the modulation of the inbound and outbound communication signals are at different frequencies to enable full duplex communication.

Figure 18:
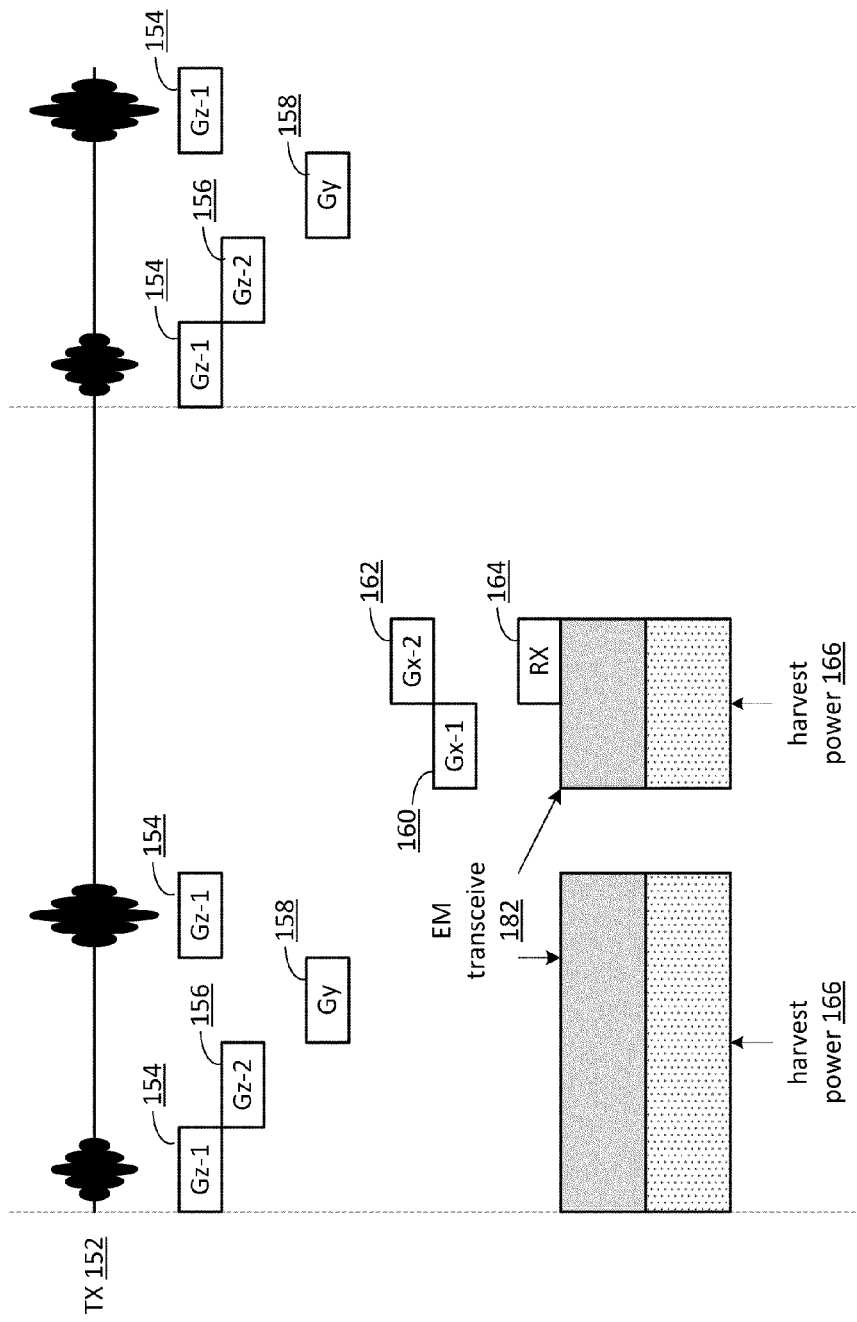
FIG. 18 is a diagram of another example of a communication protocol within a system in accordance with the present invention.

FIG. 18 is a diagram of another example of a communication protocol within the system of FIG. 17. In this diagram, the MRI transmitter 20 transmits RF signals 152, which have a frequency in the range of 3-45 MHz, at various intervals with varying signal strengths. The power harvesting module 46 of the bio-medical units 10 may use these signals to generate power for the bio-medical unit 10.

In addition to the MRI transmitter 20 transmitting its signal, a constant magnetic field and various gradient magnetic fields are created 154-164 (one or more in the x dimension Gx, one or more in the y dimension Gy, and one or more in the z direction Gz). The power harvesting module 46 of the bio-medical unit 10 may further use the constant magnetic field and/or the varying magnetic fields 154-164 to create power for the bio-medical unit 10.

During the transmission periods of the cycle, the bio-medical unit 10 may communicate via the modulated EM signals 182. In this regard, the bio-medical unit 10 generates power and communicates in accordance with the conventional transmission-magnetic field pattern of an MRI machine.

Figure 19:
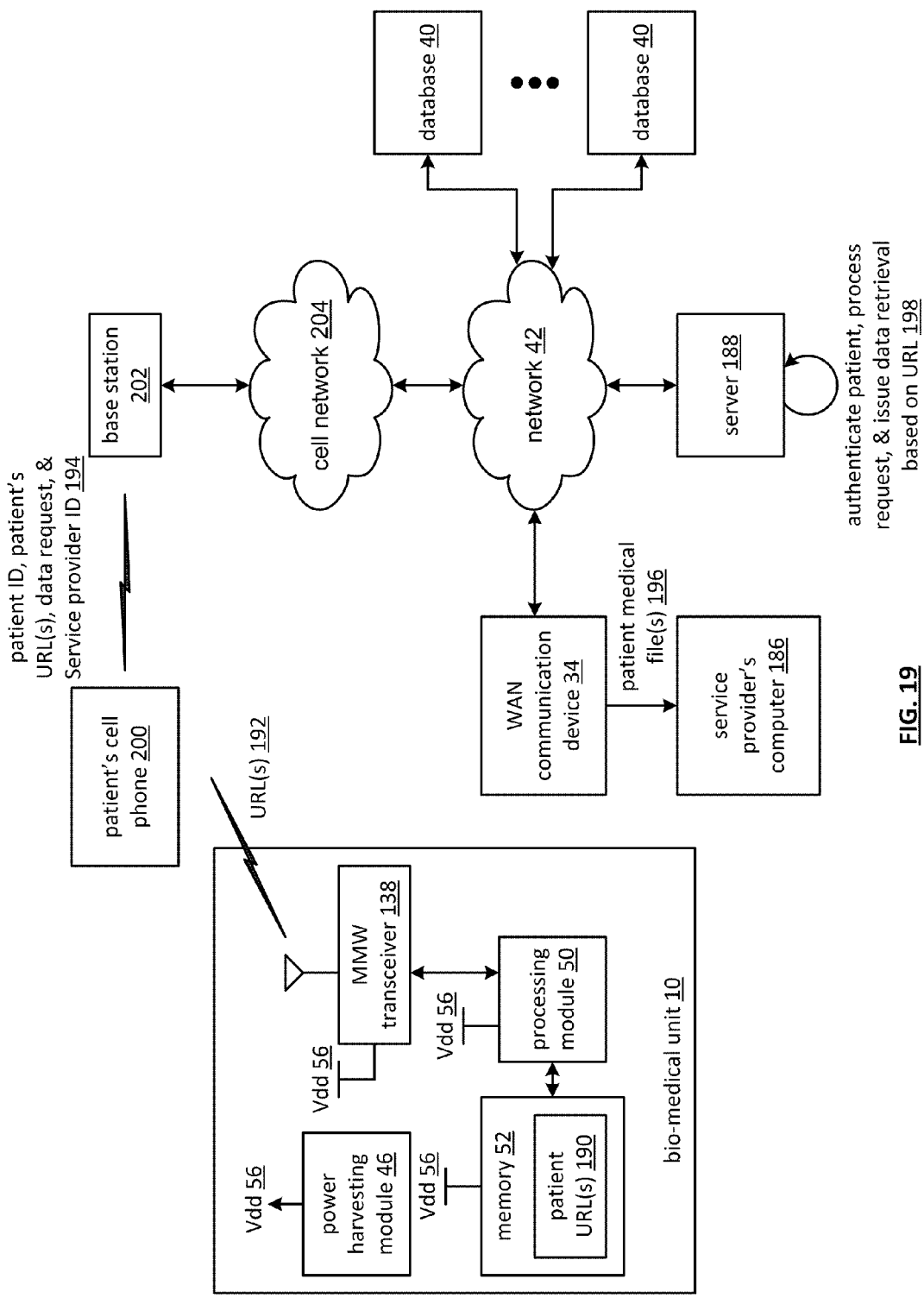
FIG. 19 is a diagram of another embodiment of a system in accordance with the present invention.

FIG. 19 is a diagram of another embodiment of a system that includes one or more bio-medical units 10, the patient's cell phone 200, a WAN communication device 34, a service provider's computer 186, a network 42, one or more databases 40, and a server 188. The bio-medical unit 10 includes a power harvesting module 46, a processing module 50, memory 52, and a MMW transceiver 138. The memory 52 is storing URL data for the patient 190. Note that the bio-medical unit 10 may be implanted in the patient, on the patient's body, or on the patient's person (e.g., in a medical tag, a key chain, etc.).

The URL data 190 includes one or more URLs 192 that identify locations of the patient's medical records. For example, one URL may be for the patient's prescription records, another may be for hospitalizations, another for general office visits, etc. In this regard, the bio-medical unit 10 is an index to easily access the patient's medical history.

For a service provider to access the patient's medical records, or a portion thereof, the patient's cell phone retrieves 200 the URL(s) 192 from the bio-medical unit 10. The cell phone 200 generates a request to access the patient's information, where the request includes the URL(s) 192, the service provider's ID, the patient's ID, and a data request. The request is provided, via the WAN device 34 and the network 42, to the server 188.

The server 188 processes 198 the request. If the service provider is authenticated and the request is valid, the server issues a data retrieval message to the one or more databases 40 identified by the URL(s) 192. The addressed database(s) 40 retrieves the data and provides it via the network 42 and the WAN device 34 to the service provider's computer 186.

Figure 20:
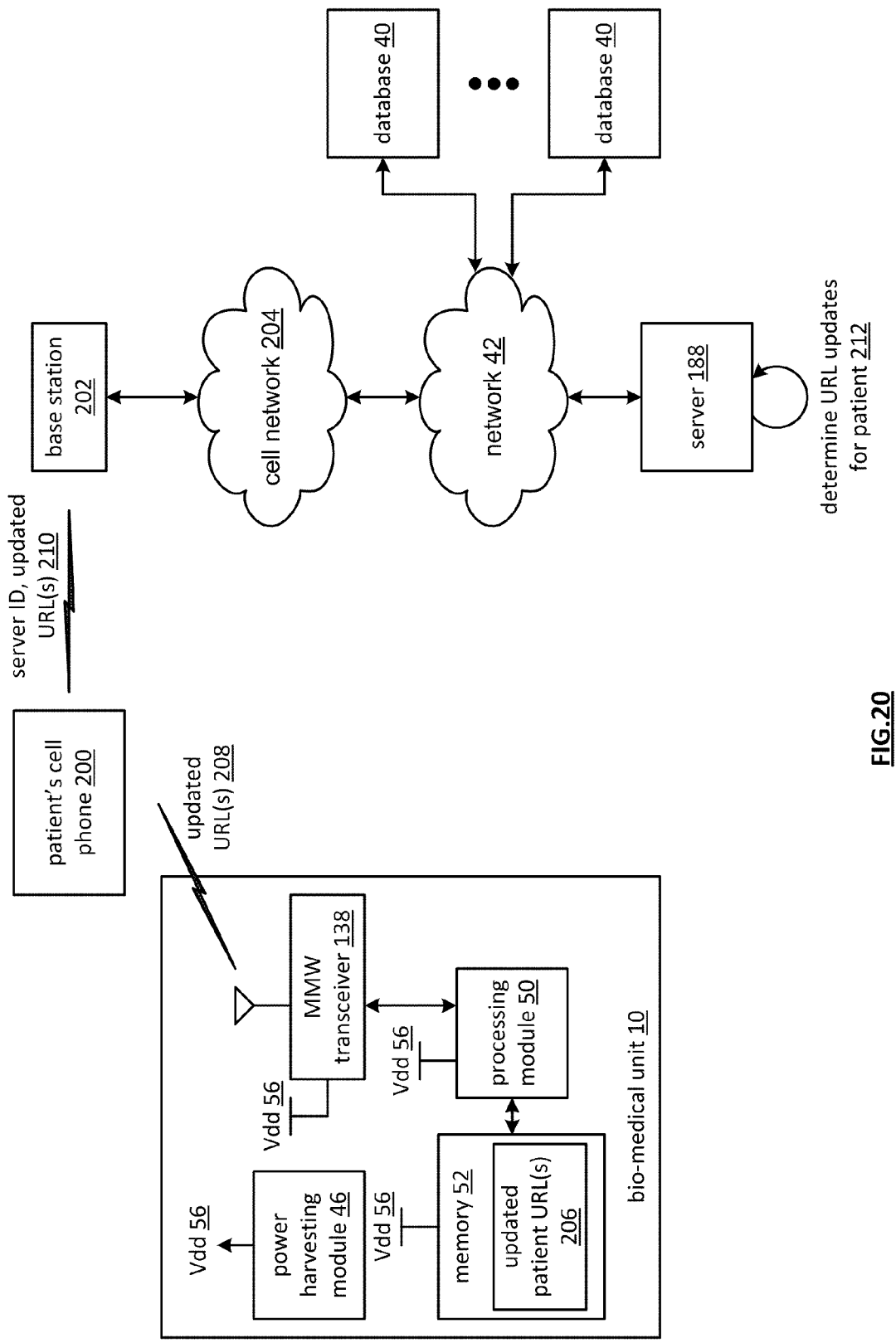
FIG. 20 is a diagram of another embodiment of a system in accordance with the present invention.

FIG. 20 is a diagram of another embodiment of a system that includes one or more bio-medical units 10, the patient's cell phone 200, a WAN communication device 34, a service provider's computer 186, a network 42, one or more databases 40, and a server 188. The bio-medical unit 10 includes a power harvesting module 46, a processing module 50, memory 52, and a MMW transceiver 138. The memory 52 is storing URL data for the patient. Note that the bio-medical unit 10 may be implanted in the patient, on the patient's body, or on the patient's person (e.g., in a medical tag, a key chain, etc.).

The URL data includes one or more URLs that identify locations of the patient's medical records. For example, one URL may be for the patient's prescription records, another may be for hospitalizations, another for general office visits, etc. In this regard, the bio-medical unit is an index to easily access the patient's medical history.

To update the URL(s) in the bio-medical unit 10, the server 188 determines when an update is needed 212. When an update is needed, the server 188 generates an update message that includes the identity of the patient's cell phone 200, the updated URL data 208, and the identity of the bio-medical unit 10. The server 188 provides the update message to the patient's cell phone 200 via the network 42 and a base station 202. The patient's cell phone 200 processes the update message and, when validated, provides the updated URL data 208 to the bio-medical unit 10 for storage in memory 52 as stored updated patient URL(s) 206.

Figure 21:
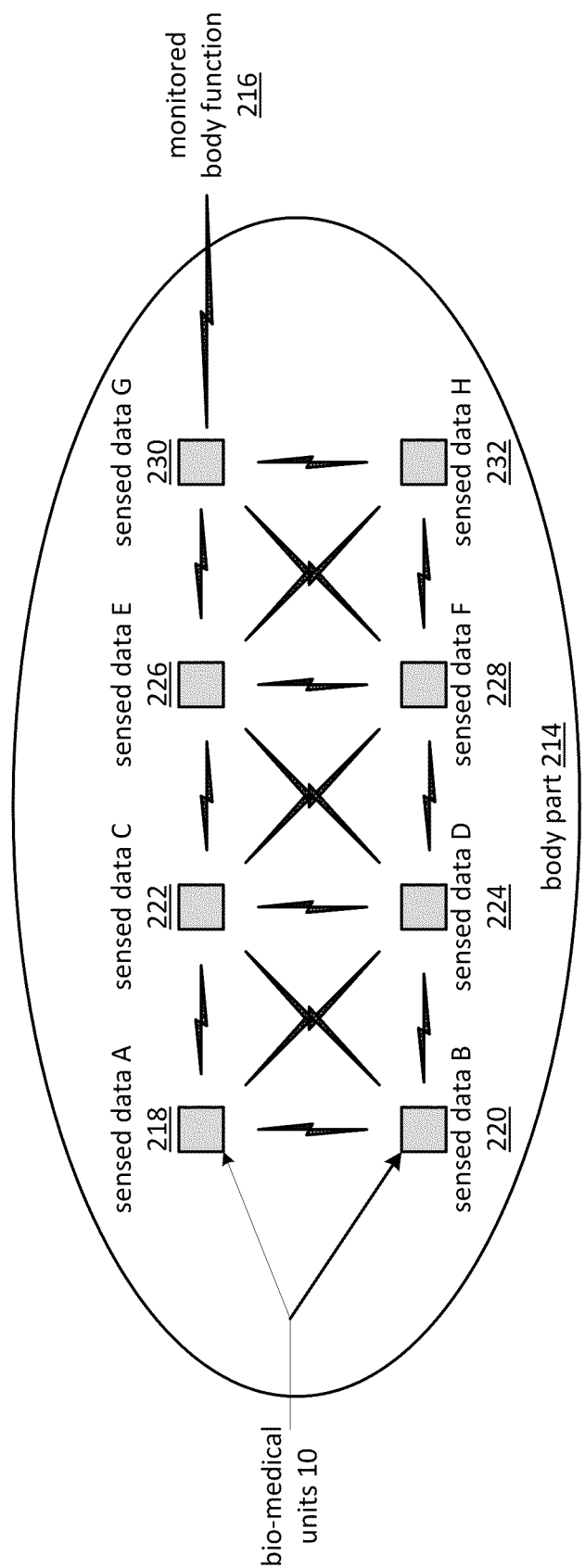
FIG. 21 is a diagram of an embodiment of a network of bio-medical units in accordance with the present invention.

FIG. 21 is a schematic block diagram of an embodiment of networked bio-medical units 10 that communicate with each other, perform sensing functions to produce sensed data 218-232, process the sensed data to produce processed data, and transmit the processed data 216. The bio-medical units 10 may be positioned in a body part to sense data across the body part and to transmit data to an external communication device. The transmitted data may be further processed or aggregated from sensed data.

The bio-medical units 10 may monitor various types of biological functions over a short term or a long term to produce the sensed data 218-232. Note that the sensed data 218-232 may include blood flow rate, blood pressure, temperature, air flow, blood oxygen level, density, white cell count, red cell count, position information, etc.

The bio-medical unit 10 establishes communications with one or more other bio-medical units 10 to facilitate the communication of sensed data 218-232 and processed data 216. The communication may include EM signals, MMW signals, optical signals, sound signals, and/or RF signals.

The bio-medical unit 10 may determine position information based on the sensed data 218-232 and include the position information in the communication. The bio-medical unit 10 may also determine a mode of operation based on one or more of a command, a list, a predetermination, sensed data, and/or processed data. For example, a bio-medical unit 10 at the center of the body part may be in a mode to sense temperature and a bio-medical unit 10 at the outside edge of the body part may sense blood flow.

The bio-medical unit 10 may receive processed data 218-232 from another bio-medical unit and re-send the same processed data 218-232 to yet another bio-medical unit 10. The bio-medical unit 10 may produce processed data based on sensed data 218-232 from the bio-medical unit 10 and/or received processed data from another bio-medical unit 10.

Figure 22:
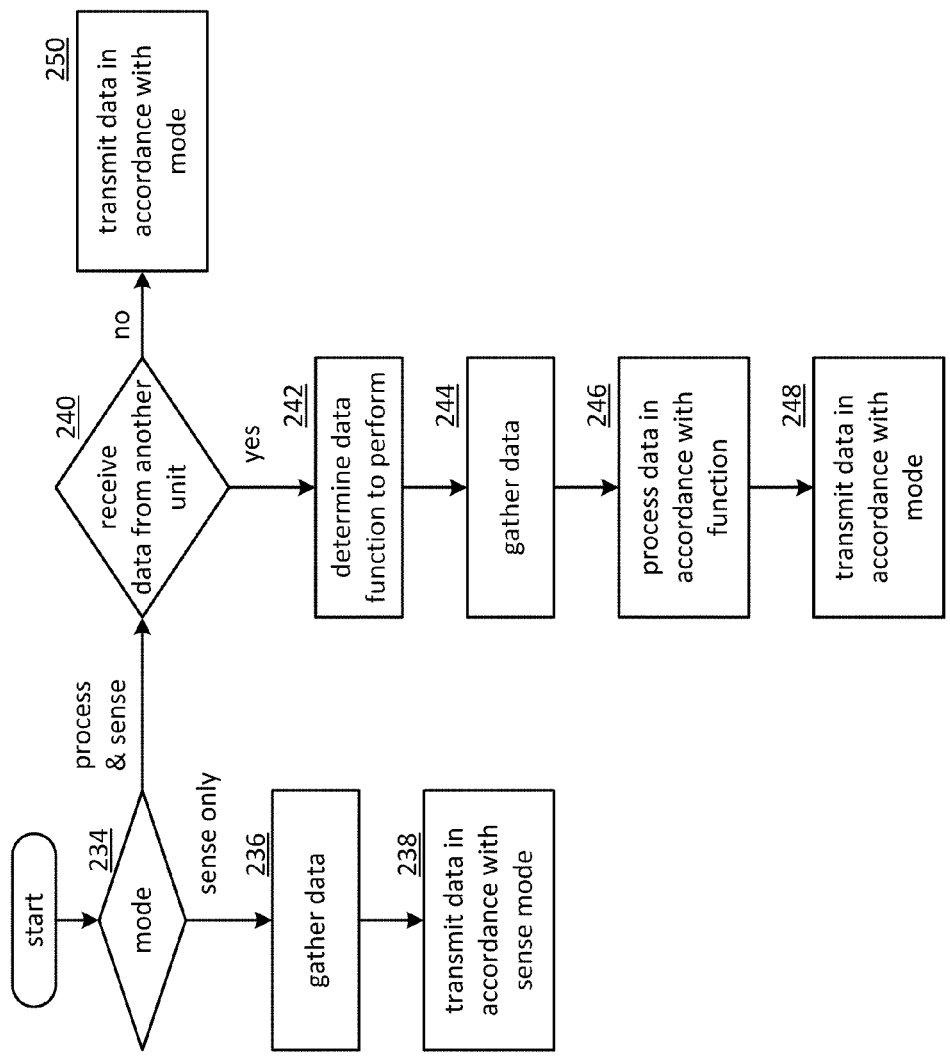
FIG. 22 is a logic diagram of an embodiment of a method for bio-medical unit communications in accordance with the present invention.

FIG. 22 is a flowchart illustrating the processing of networked bio-medical unit data where the bio-medical unit determines the sense mode based on one or more of a predetermination, a stored mode indicator in memory, a command, and/or a dynamic sensed data condition. The method begins at step 234 where the bio-medical unit 10 determines the mode. The method branches to step 240 when the bio-medical unit 10 determines that the mode is process and sense. The method continues to step 236 when the bio-medical unit 10 determines that the mode is sense only.

At step 236, the bio-medical unit 10 gathers data from one or more of the functional modules 54 to produce sensed data. The bio-medical unit 10 may transmit the sensed data 238 to another bio-medical unit 10 and/or an external communication device in accordance with the sense mode. For example, the bio-medical unit 10 may transmit the sensed data at a specific time, to a specific bio-medical unit 10, to a specific external communication device, after a certain time period, when the data is sensed, and/or when the sensed data compares favorably to a threshold (e.g., a temperature trip point).

The method continues at step 240 where the bio-medical unit 10 determines whether it has received data from another unit 10. If not, the method continues to step 250, where the bio-medical unit 10 transmits its sensed data to another bio-medical unit 10 and/or an external communication device in accordance with the sense mode.

When the bio-medical unit 10 has received data from another unit, the method continues at step 242, where the bio-medical unit 10 determines a data function to perform based on one or more of the content of the received data, the sensed data, a command, and/or a predetermination. The data function may one or more of initialization, comparing, compiling, and/or performing a data analysis algorithm.

The method continues at step 244, where the bio-medical unit 10 gathers data from the functional modules 54, and/or the received data from one or more other bio-medical units 10. The method continues at step 246, where the bio-medical unit 10 processes the data in accordance with a function to produce processed data. In addition to the example provided above, the function may also include the functional assignment of the bio-medical unit 10 as determined by a predetermination, a command, sensed data, and/or processed data (e.g., measure blood pressure from the plurality of bio-medical units and summarize the high, low, and average).

The method continues at step 248, where the bio-medical unit 10 transmits the processed data to another bio-medical unit 10 and/or to an external communication device in accordance with the sense mode. For example, the bio-medical unit 10 may transmit the sensed data at a specific time, to a specific bio-medical unit 10, to a specific external communication device, after a certain time period, when the data is sensed, and/or when the sensed data compares favorably to a threshold (e.g., a temperature trip point). Note that the communication protocol may be the same or different between bio-medical units 10 and/or between the bio-medical unit 10 and the external communication device.

Figure 23:
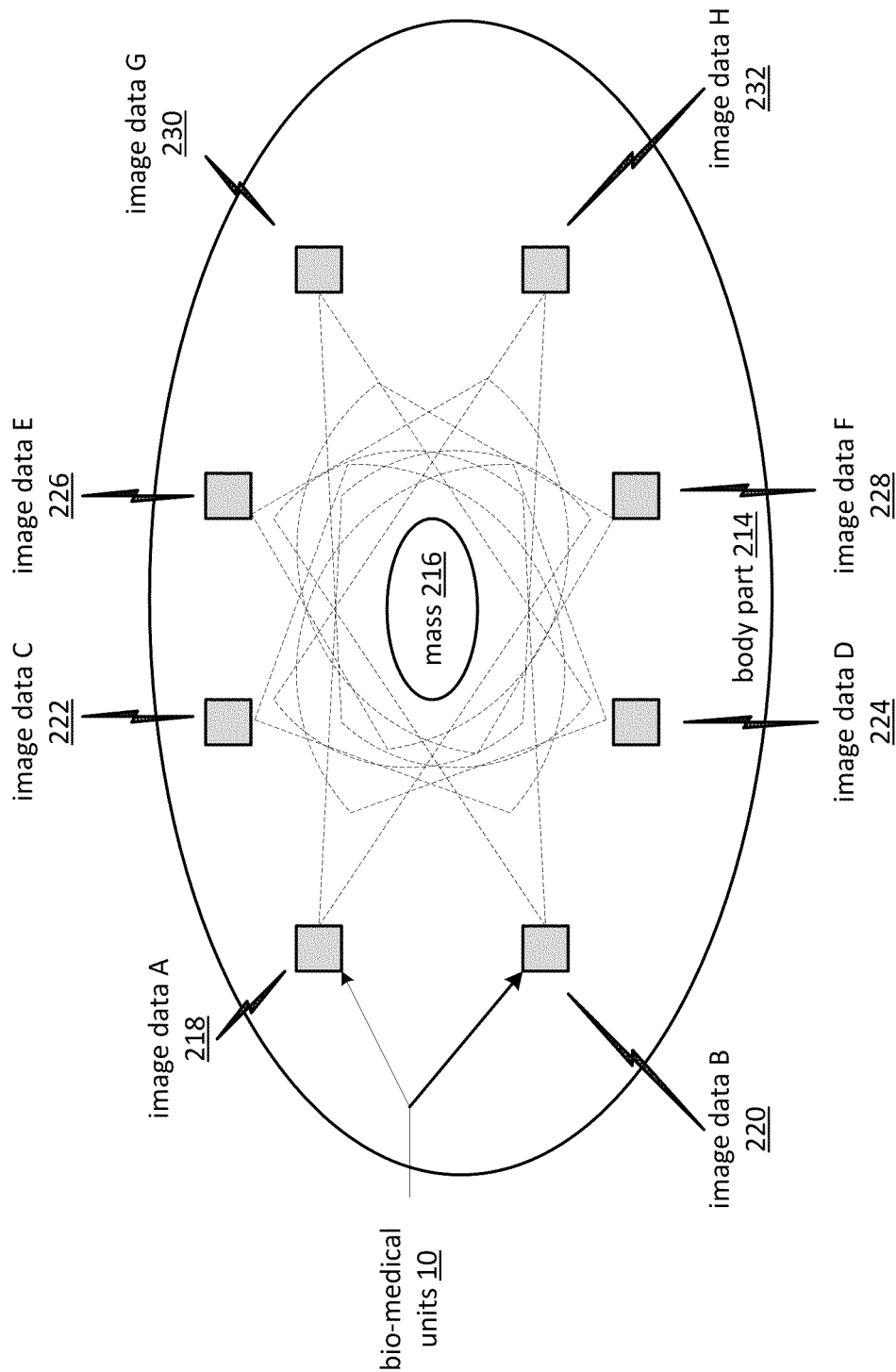
FIG. 23 is a diagram of an embodiment of a network of bio-medical units collecting image data in accordance with the present invention.

FIG. 23 is a schematic block diagram of an embodiment of a plurality of imaging bio-medical units 10 in a body part 214 where image data A-H 218-232 is provided by the plurality of imaging bio-medical units 10 that may pertain to a mass 216 within the body part 214.

The bio-medical units 10 may determine an operational mode based on a pre-determination (e.g., pre-programmed) and/or system level coordination commands received from an external communication device. The operational mode may specify how to gather image data (e.g., MMW radar sweep, ultrasound, light) and where to gather it (e.g., pointing at a specific location within the body).

In an example, the bio-medical units 10 perform the MMW radar sweep of a mass 216 in a body part in a coordinated fashion such that each bio-medical unit 10 performs the MMW radar sweep sequentially. In another example, one bio-medical unit 10 transmits a radar sweep while the other bio-medical units 10 generate image data based on received reflections.

Figure 24:
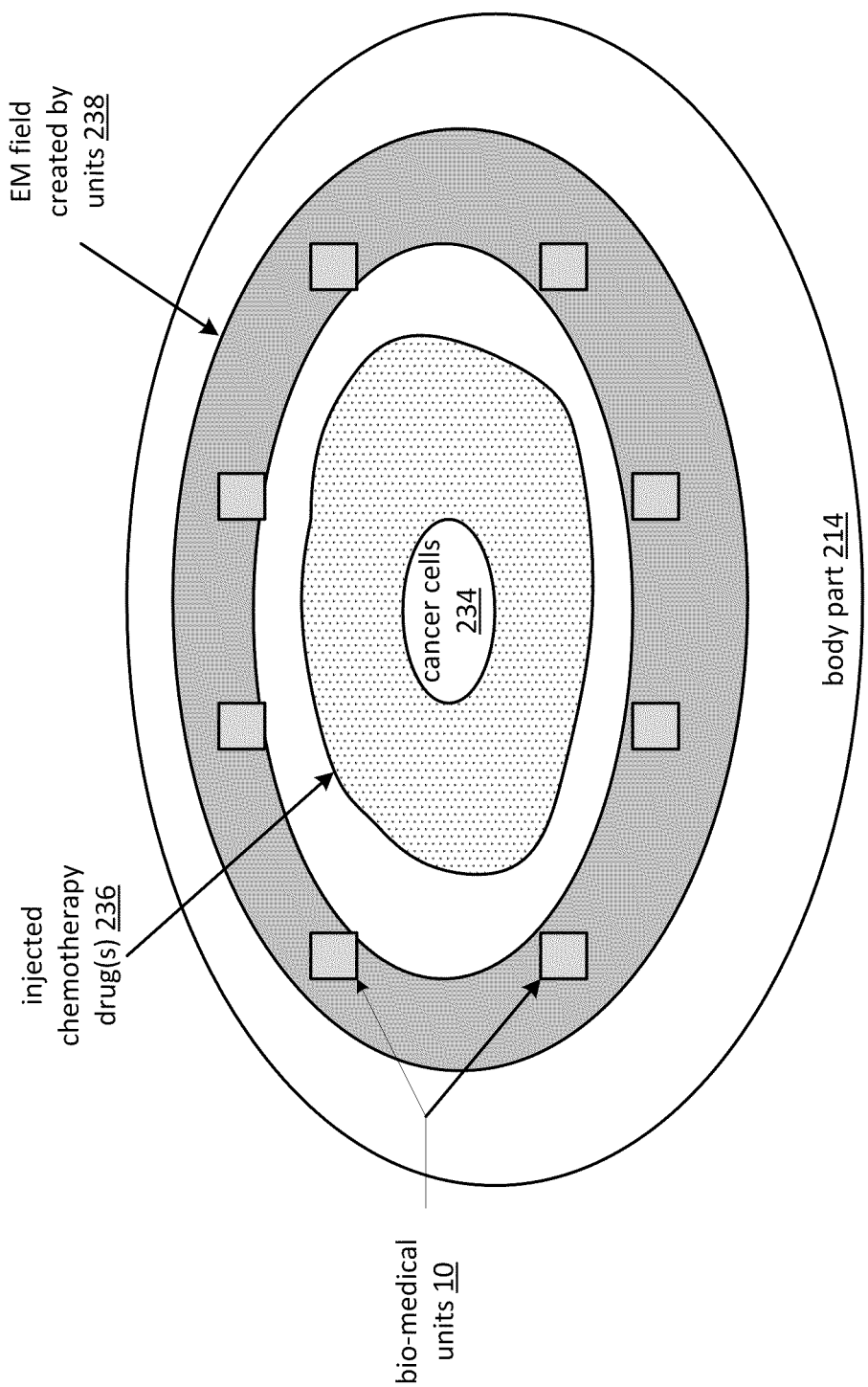
FIG. 24 is a diagram of an embodiment of a network of bio-medical units facilitating cancer treatment in accordance with the present invention.

FIG. 24 is a schematic block diagram of an embodiment of an in vivo cancer treatment system that includes a plurality of bio-medical units 10, a communication control device, and a wireless power source device (shown in other figures). At least one of the bio-medical units includes a power harvesting module, a communication module, and a field generation module. The power harvesting module is operable to convert a wireless power source into a supply voltage. The communication module is operable to communication data. Various embodiments of the power harvesting module and the communication module are discussed in one or more FIGS. 1-41.

The field generation module, which may be one or more of the functional modules discussed in one or more of FIGS. 1-41, is operable to generate a type of electromagnetic field to facilitate cancer treatment. The field generation module includes a fixed and/or variable oscillation module (e.g., phase locked loop, voltage controlled oscillator, digital frequency synthesizer, etc.) to produce an oscillation, an amplifier circuit to amplify the oscillation, and one or more antennas and/or one or more coils to generate an electric field and/or a magnetic field. For example, the field generation module may generate an electric field to contain a cancer treatment drug (e.g., a chemotherapy drug) in a localized area that at least partially encircling the cancer cells when the cancer treatment drug is ionized. As another example, the field generation module may generate a magnetic field to contain the cancer treatment drug in the localized area that at least partially encircling the cancer cells when the cancer treatment drug is polarized.

As yet another example, the field generation module may generate an electric field to charge a second substance that contains a cancer treatment drug in a localized area that at least partially encircling the cancer cells when the cancer treatment drug is ionized. As a further example, the field generation module may generate a magnetic field to magnetize the second substance that contains the cancer treatment drug in the localized area that at least partially encircling the cancer cells when the cancer treatment drug is polarized.

In another embodiment, or in further of the preceding embodiment, the field generation module includes a radio frequency (RF) transmitter to transmit RF signals at the cancer cells to facilitate RF radiation of the cancer cells. In yet another embodiment, or in furtherance of one or more of the preceding embodiments, the field generation module includes a millimeter wave (MMW) transmitter to transmit MMW signals at the cancer cells to facilitate MMW radiation of the cancer cells. Note that the RF and MMW frequency bands include frequencies from approximately 30 MHz to 300 GHz.

The communication control device, which may be external to the body, communicates with the plurality of bio-medical units to facilitate treatment of cancer cells within the body. For instance, the communication control device may transmit a first control signal to a first set of the bio-medical units. The first control signal contains instructions for a first pattern of treatment to be performed by the first set of bio-medical units. For example, enabling the units in a round-robin manner, instruct the units to transmit at a given power level, instruct the units to be positioned at given locations, etc. In addition to, or in the alternative, the communication control device may transmit a second control signal to a second set of bio-medical units. The second control signal contains instructions for a second pattern of treatment to be performed by the second set units.

In an embodiment, the communication control device includes an RF transceiver, a MMW transceiver, and/or a magnetic resonance transceiver. The RF transceiver may be operable to transceive RF data signals with at least one of the bio-medical units. The MMW transceiver may be operable to transceive MMW data signals with at least one of the bio-medical units. The magnetic resonance transceiver may be operable to transceive magnetic resonance data signals with at least one of the plurality of bio-medical units. Examples of transceivers are discussed with reference to one of more of the FIGS. 1-41.

The wireless power source device, which may be external to the body, generates the wireless power source that is wirelessly transmitted to the bio-medical units. The wireless power source device may include an RF generating module, a MMW signal generating module, and/or a magnetic resonance signal generating module. The RF generating module may be operable to generate an RF power signal as the wireless power source. The MMW signal generating module may be operable to generate a MMW power signal as the wireless power source. The magnetic resonance signal generating module may be operable to generate a magnetic resonance power signal as the wireless power source. Examples of the signal generating modules are discussed with reference to one of more of the FIGS. 1-41.

In another embodiment, or in furtherance of the preceding embodiment, the bio-medical unit further includes one or more dispensing modules. For instance, the unit may include a first dispensing module and/or a second dispensing module. The first dispensing module may be used to store a cancer treatment drug and to dispense at least a portion of the cancer treatment drug in accordance with a control signal from the communication control device. The second dispensing module may be used to store a second substance that contains the cancer treatment drug in a localized area in the body that at least partially encircling the cancer cells. The second dispensing module may be operable to dispense at least a portion of the second substance in accordance with a control signal from the communication control device.

In another embodiment, or in furtherance of one or more of the preceding embodiments, the bio-medical unit further includes a propulsion module. The propulsion module may be operable to move the bio-medical unit in accordance with control signals from the communication control device. For example, the communication control device may provide signals that cause a plurality of the bio-medical units to encircle cancer cells prior to assisting in treatment. As another example, the communication control device may provides signals that cause the units to adjust their positions to adjust the electric and/or magnetic field being created to contain the cancer treatment drug(s).

In another embodiment, or in furtherance of one or more of the preceding embodiments, the bio-medical unit further includes an imaging module. The imaging module may be operable to generate image data regarding the treatment. For example, the imaging module may be used to provide image feedback regarding the position of the units, the containment of the cancer treatment drug, etc.

To insure that a bio-medical unit maintains a minimal level of power to perform its function(s) the in vivo cancer treatment system may have the bio-medical unit monitor its power level and transmit it to the communication control device. The communication control device interprets the power level data. If the bio-medical unit requires charging, the communication control device transmits a charge enable signal to the wireless power source device and temporarily suspending the treatment. The wireless power source device generates the wireless power source in response to the charge enable signal.

In an example of operation, the bio-medical units 10 are positioned to encircle cancer cells in two or three-dimensional space. The positioning may be done by injection into the desired positions; by injecting the units into an area of the body that is proximal to the cancer cells and then moved, via control signals and propulsion, to the desired location; etc. Note that if the units' position is adjusted via control signals and propulsion, the wireless power source device provides the wireless power source signal to the units such that they have power to process the control signals and to enable the propulsion module.

With the units in position and powered, they may be activated to generate an electromagnetic field (e.g., an electric field and/or a magnetic field) via one or more control signals from the communication control device. With the units generating the electromagnetic field, a ionized and/or magnetized cancer treatment drug (e.g., a chemotherapy drug) is injected near the cancer cells. The electromagnetic field contains the chemotherapy drug in the immediate area of the cancer cells with minimal exposure to healthy cells. In this manner, a lower quantity of cancer treatment drugs may be topically applied to effectively treat cancer, which minimizes damage to healthy cells and reduces the body's adverse reactions to the cancer treatment drugs.

In another example of operation, some of the bio-medical units include canisters that store the cancer treatment drug(s). These units are positioned with the units that generate the electromagnetic field. Once the field is enable, the units are instructed by the communication control device to release a controlled portion of the cancer treatment drug(s). In this manner, once the units are injected into the body, cancer treatment may be done at a more convenient time and/or place for the patient.

In another example of operation, the bio-medical units are activated to generate the electromagnetic field to charge (e.g., positive or negative) and/or polarize a substance (e.g., saline). The charged and/or polarized substance contains the cancer treatment drug in the desired location surrounding the cancer cells.

Figure 25:
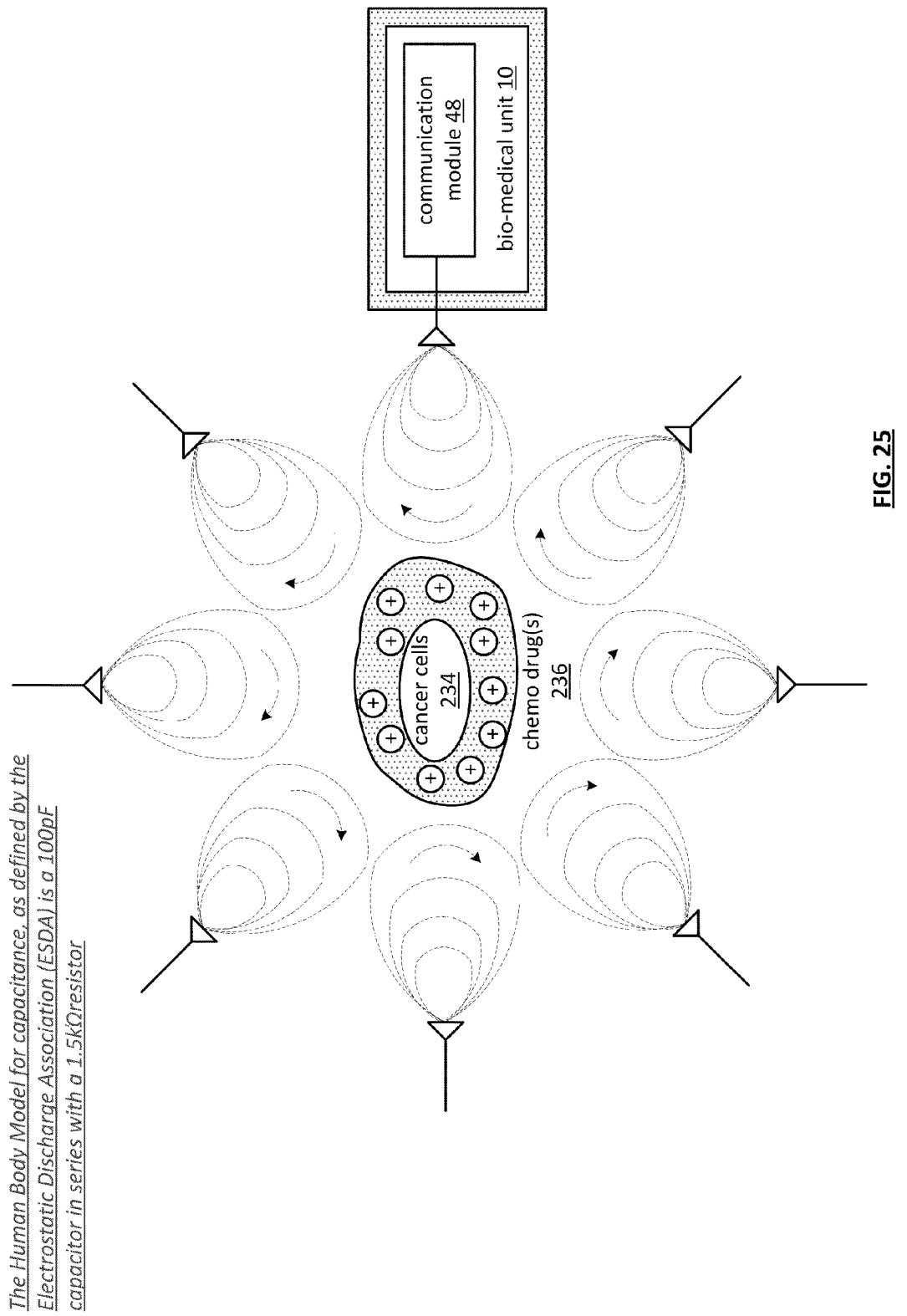
FIG. 25 is a diagram of another embodiment of a network of bio-medical units facilitating cancer treatment in accordance with the present invention.

FIG. 25 is a schematic block diagram of another embodiment an in vivo cancer treatment system that includes a plurality of bio-medical units 10, a communication control device, and a wireless power source device (shown in other figures). At least one of the bio-medical units includes a power harvesting module, a communication module, and a field generation module.

Figure 26:
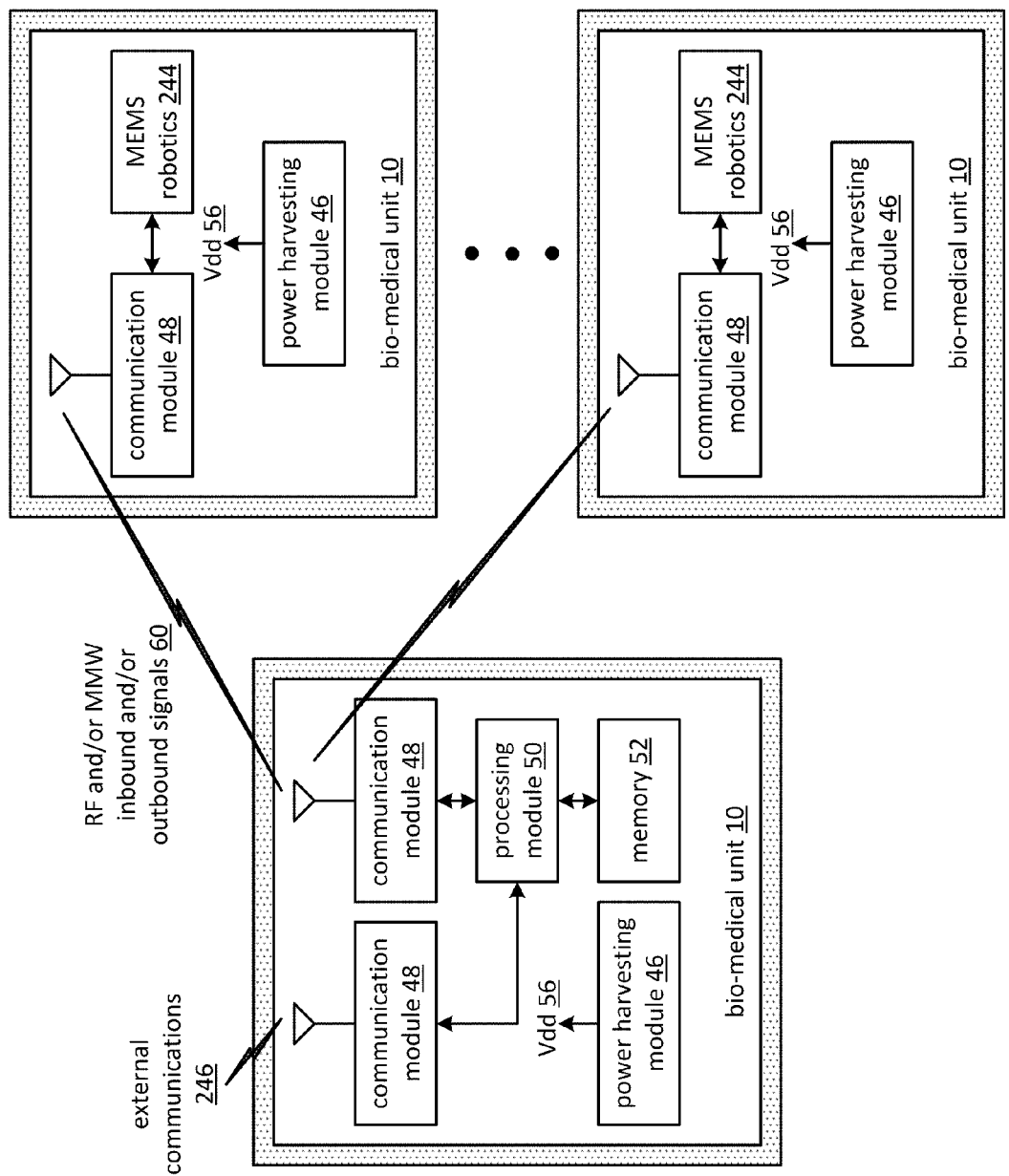
FIG. 26 is a diagram of an embodiment of a network of bio-medical units that include MEMS robotics in accordance with the present invention.

FIG. 26 is a schematic block diagram of an embodiment of a parent bio-medical unit (on the left) communicating with an external unit to coordinates the functions of one or more children bio-medical units 10 (on the right). The parent unit includes a communication module 48 for external communications, a communication module 48 for communication with the children units, the processing module 50, the memory 52, and the power harvesting module 46. Note that the parent unit may be implemented one or more chips and may in the body or one the body.

Each of the child units includes a communication module 48 for communication with the parent unit and/or other children units, a MEMS robotics 244, and the power harvesting module 46. The MEMS robotics 244 may include one or more of a MEMS technology saw, drill, spreader, needle, injection system, and actuator. The communication module 48 may support RF and/or MMW inbound and/or outbound signals 60 to the parent unit such that the parent unit may command the child units in accordance with external communications commands.

In an example of operation, the patent bio-medical unit receives a communication from the external source, where the communication indicates a particular function the child units are to perform. The parent unit processes the communication and relays relative portions to the child units in accordance with a control mode. Each of the child units receives their respective commands and performs the corresponding functions to achieve the desired function.

Figure 27:
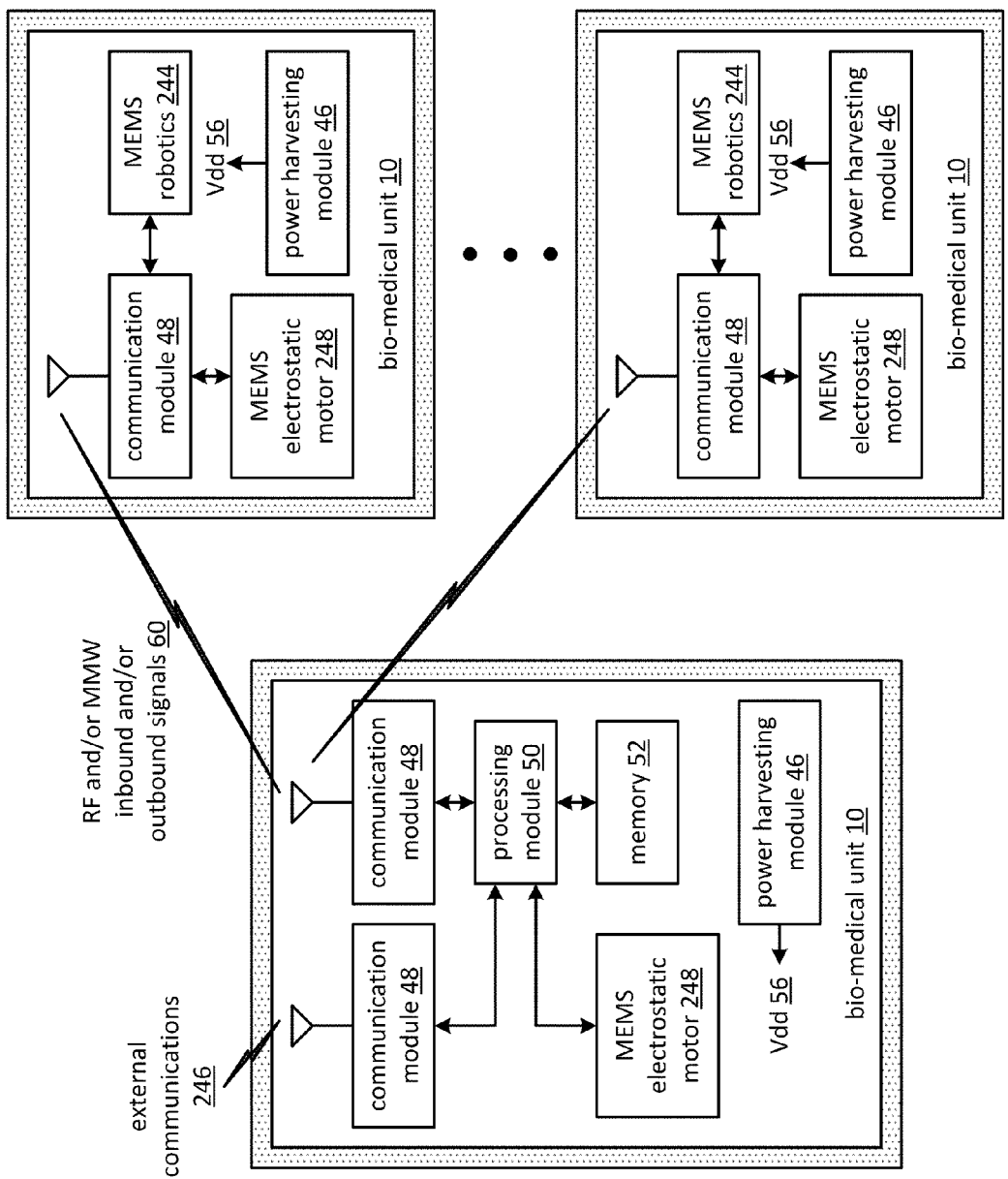
FIG. 27 is a diagram of another embodiment of a network of bio-medical units that include MEMS robotics in accordance with the present invention.

FIG. 27 is a schematic block diagram of another embodiment of a plurality of task coordinated bio-medical units 10 including a parent bio-medical unit 10 (on the left) and one or more children bio-medical units 10 (on the right). The parent unit may be implemented one or more chips and may in the body or one the body. The parent unit may harvest power in conjunction with the power booster 84.

The parent unit includes the communication module 48 for external communications, the communication module 48 for communication with the children units, the processing module 50, the memory 52, a MEMS electrostatic motor 248, and the power harvesting module 46. The child unit includes the communication module 48 for communication with the parent unit and/or other children units, a MEMS electrostatic motor 248, the MEMS robotics 244, and the power harvesting module 46. Note that the child unit has fewer components as compared to the parent unit and may be smaller facilitating more applications where smaller bio-medical units 10 enhances their effectiveness.

The MEMS robotics 244 may include one or more of a MEMS technology saw, drill, spreader, needle, injection system, and actuator. The MEMS electrostatic motor 248 may provide mechanical power for the MEMS robotics 244 and/or may provide movement propulsion for the child unit such that the child unit may be positioned to optimize effectiveness. The child units may operate in unison to affect a common task. For example, the plurality of child units may operate in unison to saw through a tissue area.

The child unit communication module 48 may support RF and/or MMW inbound and/or outbound signals 60 to the parent unit such that the parent unit may command the children units in accordance with external communications commands.

The child unit may determine a control mode and operate in accordance with the control mode. The child unit determines the control mode based on one or more of a command from a parent bio-medical unit, external communications, a preprogrammed list, and/or in response to sensor data. Note that the control mode may include autonomous, parent (bio-medical unit), server, and/or peer as previously discussed.

Figure 28:
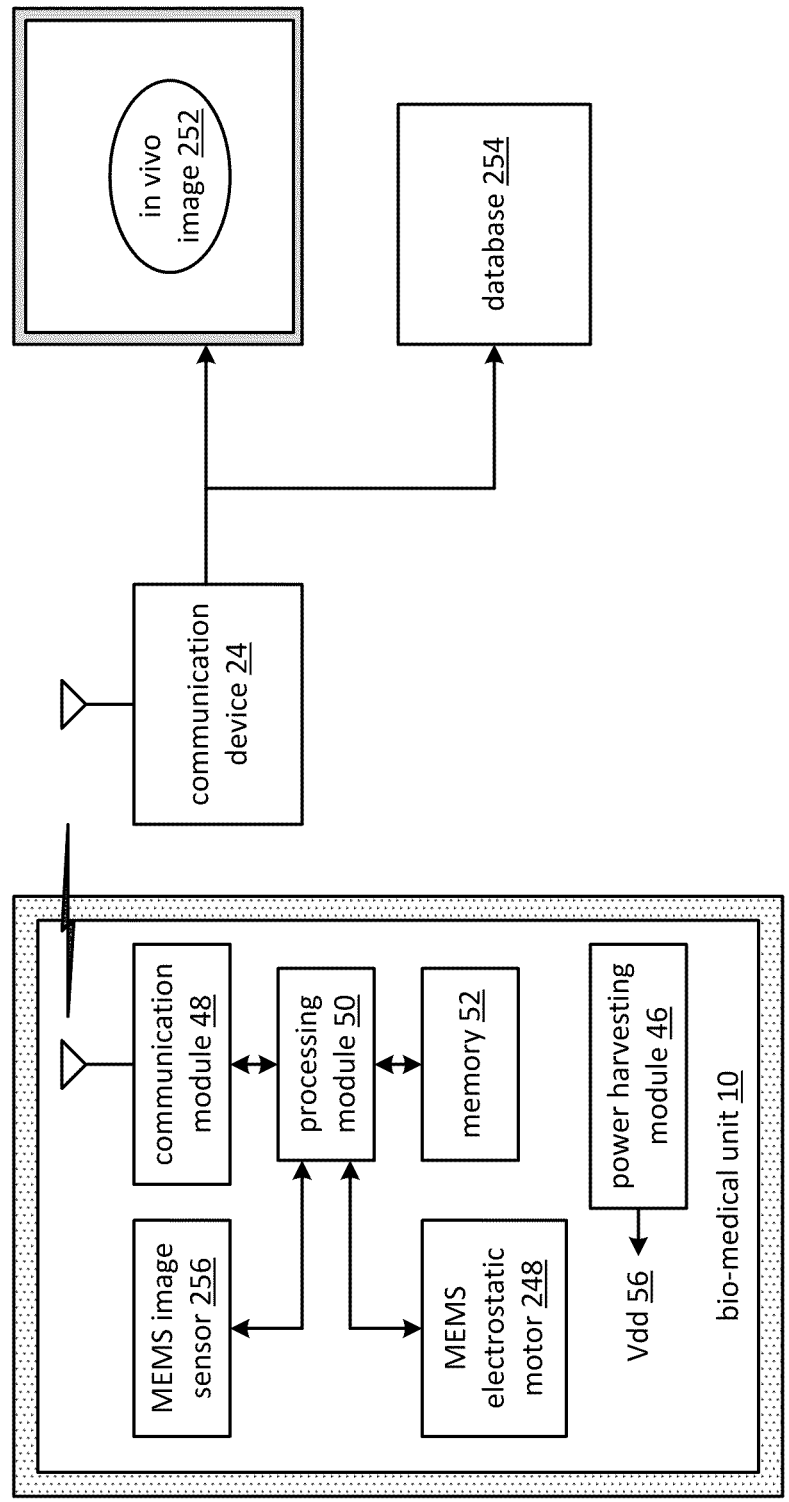
FIG. 28 is a diagram of an embodiment of a bio-medical unit collecting image data in accordance with the present invention.

FIG. 28 is a schematic block diagram of an embodiment of a bio-medical unit 10 based imaging system that includes the bio-medical unit 10, the communication device 24, a database 254, and an in vivo image unit 252. The bio-medical unit 10 may perform scans and provide the in vivo image unit 252 with processed image data for diagnostic visualization.

The bio-medical unit 10 includes a MEMS image sensor 256, the communication module 48 for external communications with the communication device, the processing module 50, the memory 52, the MEMS electrostatic motor 248, and the power harvesting module 46. In an embodiment the bio-medical unit 10 and communication device 24 communicate directly. In another embodiment, the bio-medical unit 10 and communication device 24 communicate through one or more intermediate networks (e.g., wireline, wireless, cellular, local area wireless, Bluetooth, etc.). The MEMS image sensor 256 may include one or more sensors scan types for optical signals, MMW signals, RF signals, EM signals, and/or sound signals.

The in vivo unit 252 may send a command to the bio-medical unit 10 via the communication device 24 to request scan data. The request may include the scan type. The in vivo unit 252 may receive the processed image data from the bio-medical unit 10, compare it to data in the database 254, process the data further, and provide image visualization.

Figure 29:
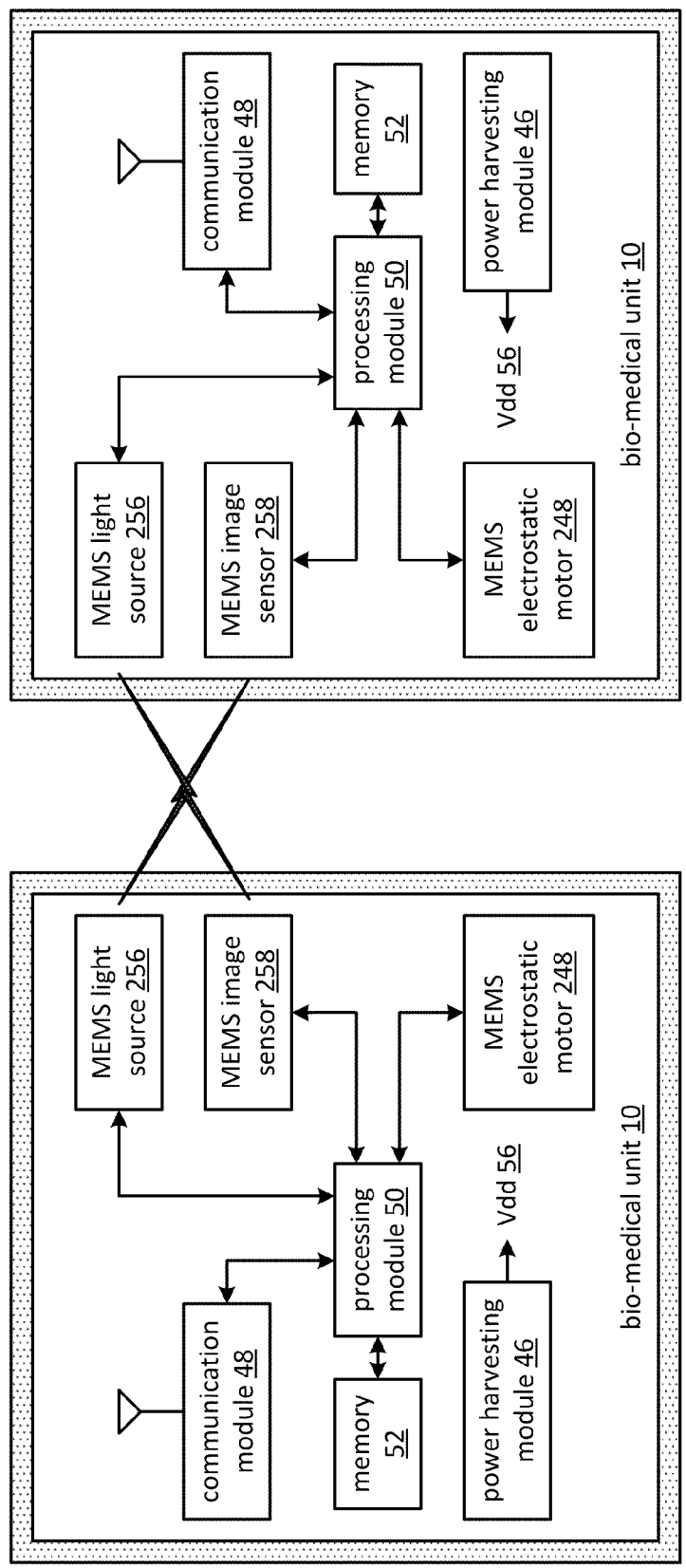
FIG. 29 is a diagram of another embodiment of a network of bio-medical units communicating via light signaling in accordance with the present invention.

FIG. 29 is a schematic block diagram of an embodiment of a communication and diagnostic bio-medical unit 10 pair where the pair utilize an optical communication medium between them to analyze material between them (e.g., tissue, blood flow, air flow, etc,) and to carry messages (e.g., status, commands, records, test results, scan data, processed scan data, etc.).

The bio-medical unit 10 includes a MEMS light source 256, a MEMS image sensor 258, the communication module 48 (e.g., for external communications with the communication device 24), the processing module 50, the memory 52, the MEMS electrostatic motor 248 (e.g., for propulsion and/or tasks), and the power harvesting module 46. The bio-medical unit 10 may also include the MEMS light source 256 to facilitate the performance of light source tasks. The MEMS image sensor 258 may be a camera, a light receiving diode, or infrared receiver. The MEMS light source 256 may emit visible light, infrared light, ultraviolet light, and may be capable of varying or sweeping the frequency across a wide band.

The processing module 50 may utilize the MEMS image sensor 258 and the MEMS light source 256 to communicate with the other bio-medical unit 10 using pulse code modulation, pulse position modulation, or any other modulation scheme suitable for light communications. The processing module 50 may multiplex messages utilizing frequency division, wavelength division, and/or time division multiplexing.

The bio-medical optical communications may facilitate communication with one or more other bio-medical units 10. In an embodiment, a star architecture is utilized where one bio-medical unit 10 at the center of the star communicates to a plurality of bio-medical units 10 around the center where each of the plurality of bio-medical units 10 only communicate with the bio-medical unit 10 at the center of the star. In an embodiment, a mesh architecture is utilized where each bio-medical unit 10 communicates as many of the plurality of other bio-medical units 10 as possible and where each of the plurality of bio-medical units 10 may relay messages from one unit to another unit through the mesh.

The processing module 50 may utilize the MEMS image sensor 258 and the MEMS light source 256 of one bio-medical unit 10 to reflect light signals off of matter in the body to determine the composition and position of the matter. In another embodiment, the processing module 50 may utilize the MEMS light source 256 of one bio-medical unit 10 and the MEMS image sensor 258 of a second bio-medical unit 10 to pass light signals through matter in the body to determine the composition and position of the matter. The processing module 50 may pulse the light on and off, sweep the light frequency, vary the amplitude and may use other perturbations to determine the matter composition and location.

Figure 30:
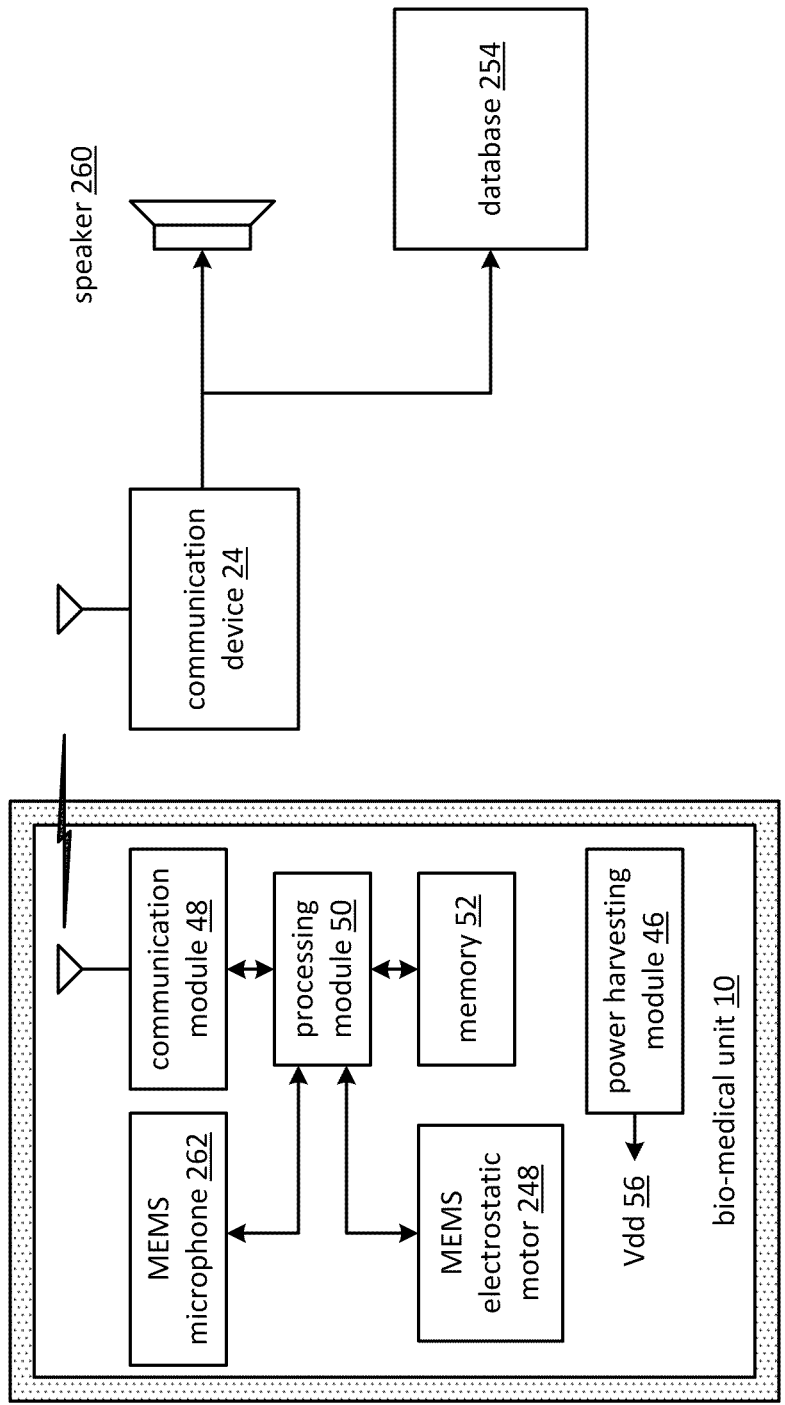
FIG. 30 is a diagram of an embodiment of a bio-medical unit collecting audio and/or ultrasound data in accordance with the present invention.

FIG. 30 is a schematic block diagram of an embodiment of a bio-medical unit 10 based sounding system that includes the bio-medical unit 10, the communication device 24, the database 254, and a speaker 260. The bio-medical unit 10 may perform scans and provide the speaker 260 with processed sounding data for diagnostic purposes via the communication device 24.

The bio-medical unit 10 includes a MEMS microphone 262, the communication module 48 for external communications with the communication device 24, the processing module 50, the memory 52, the MEMS electrostatic motor 248, and the power harvesting module 46. In an embodiment the bio-medical unit 10 and communication device 24 communicate directly. In another embodiment, the bio-medical unit 10 and communication device 24 communicate through one or more intermediate networks (e.g., wireline, wireless, cellular, local area wireless, Bluetooth, etc.) The MEMS microphone 262 may include one or more sensors to detect audible sound signals, sub-sonic sound signals, and/or ultrasonic sound signals.

The processing module 50 may produce the processed sounding data based in part on the received sound signals and in part on data in the database 254. The processing module 50 may retrieve data via the communication module 48 and communication device 24 link from the database 254 to assist in the processing of the signals (e.g., pattern matching, filter recommendations, sound field types). The processing module 50 may process the signals to detect objects, masses, air flow, liquid flow, tissue, distances, etc. The processing module 50 may provide the processed sounding data to the speaker 260 for audible interpretation. In another embodiment, the bio-medical unit 10 assists an ultrasound imaging system by relaying ultrasonic sounds from the MEMS microphone 262 to the ultrasound imaging system instead of to the speaker 260.

Figure 31:
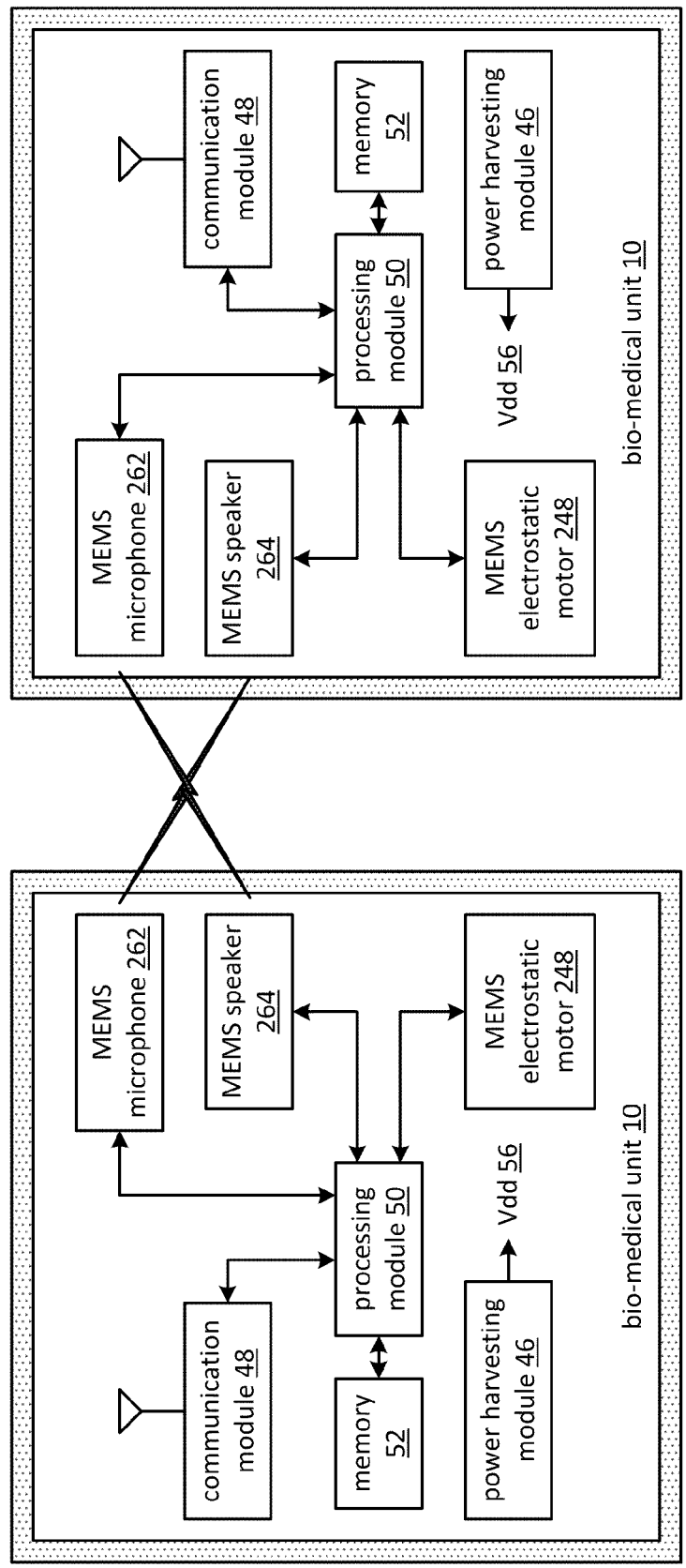
FIG. 31 is a diagram of another embodiment of a network of bio-medical units communicating via audio and/or ultrasound signaling in accordance with the present invention.

FIG. 31 is a schematic block diagram of another embodiment of a bio-medical unit 10 communication and diagnostic pair where the pair utilize an audible communication medium between them to analyze material between them (e.g., tissue, blood flow, air flow, etc,) and to carry messages (e.g., status, commands, records, test results, scan data, processed scan data, etc.). The bio-medical unit 10 includes the MEMS microphone 262, a MEMS speaker 264, the communication module 48 (e.g., for external communications with the communication device), the processing module 50, the memory 52, the MEMS electrostatic motor 248 (e.g., for propulsion and/or tasks), and the power harvesting module 46. The bio-medical unit 10 may also include the MEMS speaker 264 to facilitate performance of sound source tasks.

The MEMS microphone 262 and MEMS speaker 264 may utilize audible sound signals, sub-sonic sound signals, and/or ultrasonic sound signals and may be capable of varying or sweeping sound frequencies across a wide band. The processing module 50 may utilize the MEMS microphone 262 and MEMS speaker 264 to communicate with the other bio-medical unit 10 using pulse code modulation, pulse position modulation, amplitude modulation, frequency modulation, or any other modulation scheme suitable for sound communications. The processing module 50 may multiplex messages utilizing frequency division and/or time division multiplexing.

The bio-medical sound based communications may facilitate communication with one or more other bio-medical units 10. In an embodiment, a star architecture is utilized where one bio-medical unit 10 at the center of the star communicates to a plurality of bio-medical units 10 around the center where each of the plurality of bio-medical units 10 only communicate with the bio-medical unit 10 at the center of the star. In an embodiment, a mesh architecture is utilized where each bio-medical unit 10 communicates as many of the plurality of other bio-medical units 10 as possible and where each of the plurality of bio-medical units 10 may relay messages from one unit to another unit through the mesh.

The processing module 50 may utilize the MEMS microphone 262 and MEMS speaker 264 of one bio-medical unit 10 to reflect sound signals off of matter in the body to determine the composition and position of the matter. In another embodiment, the processing module 50 may utilize the MEMS microphone 262 of one bio-medical unit 10 and the MEMS speaker 264 of a second bio-medical unit 10 to pass sound signals through matter in the body to determine the composition and position of the matter. The processing module 50 may pulse the sound on and off, sweep the sound frequency, vary the amplitude and may use other perturbations to determine the matter composition and location.

Figure 32:
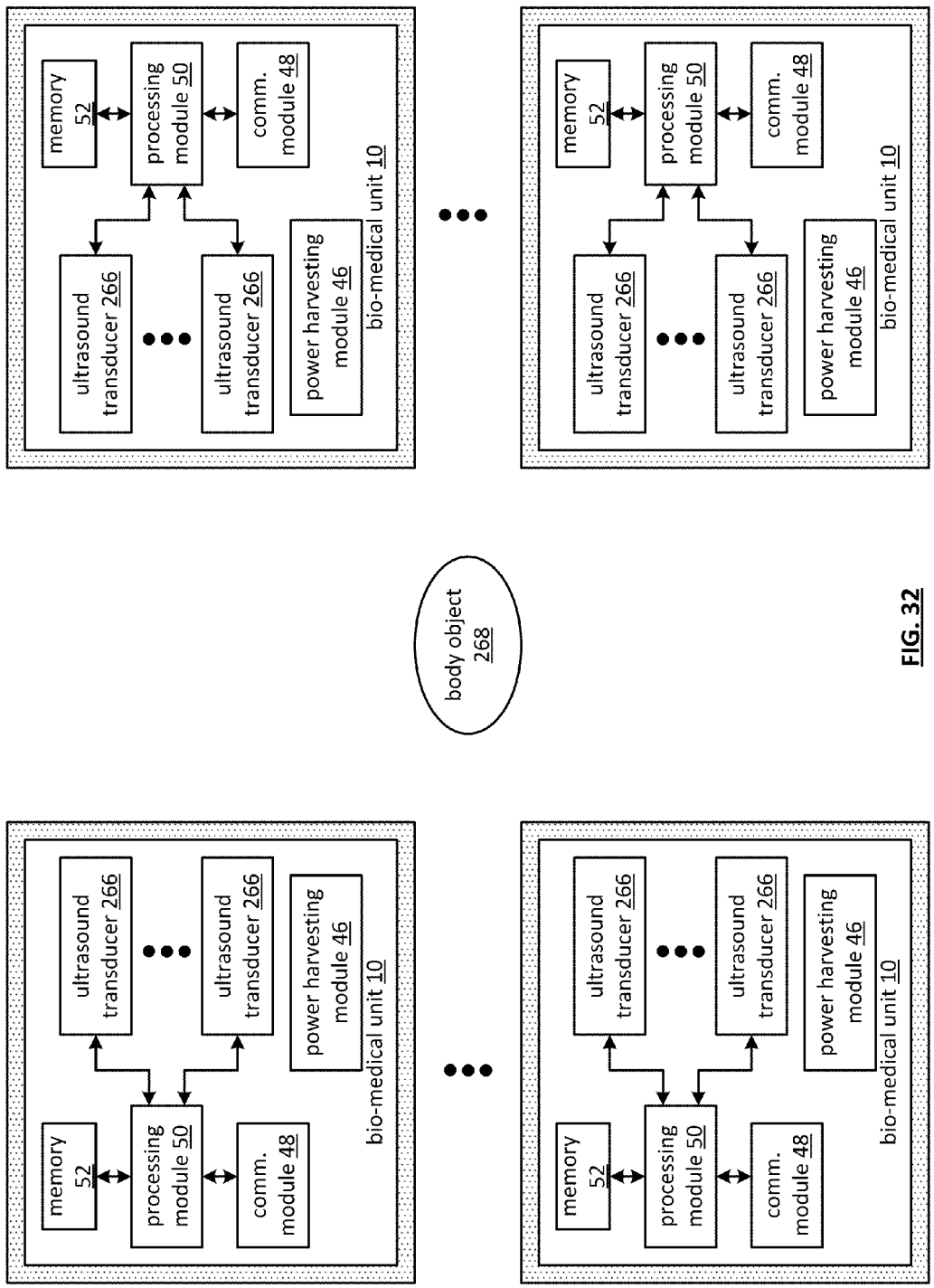
FIG. 32 is a diagram of an embodiment of a network of bio-medical units collecting ultrasound data in accordance with the present invention.

FIG. 32 is a schematic block diagram of an embodiment of a sound based imaging system including a plurality of bio-medical units 10 utilizing short range ultrasound signals in the 2-18 MHz range to facilitate imaging a body object 268. The bio-medical unit 10 includes at least one ultrasound transducer 266, the communication module 48 (e.g., for external communications with the communication device and for communications with other bio-medical units), the processing module 50, the memory 52, and the power harvesting module 46. The ultrasound transducer 266 may be implemented utilizing MEMS technology.

The processing module 50 controls the ultrasonic transducer 266 to produce ultrasonic signals and receive resulting reflections from the body object 268. The processing module 50 may coordinate with the processing module 50 of at least one other bio-medical unit 10 to produce ultrasonic signal beams (e.g., constructive simultaneous phased transmissions directed in one direction) and receive resulting reflections from the body object. The processing module 50 may perform the coordination and/or the plurality of processing modules 50 may perform the coordination. In embodiment, the plurality of processing modules 50 receives coordination information via the communication module 48 from at least one other bio-medical unit 10. In another embodiment, the plurality of processing modules 50 receives coordination information via the communication module 48 from an external communication device.

The processing module produces processed ultrasonic signals based on the received ultrasonic reflections from the body object 268. For example, the processed ultrasonic signals may represent a sonogram of the body part. The processing module 50 may send the processed ultrasonic signals to the external communication device and/or to one or more of the plurality of bio-medical units 10.

Figure 33:
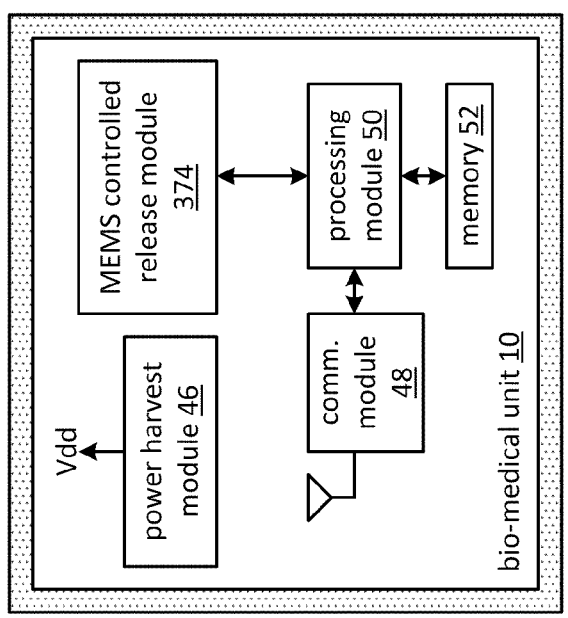
FIG. 33 is a diagram of an embodiment of a bio-medical unit including a controlled release module in accordance with the present invention.

FIG. 33 is a schematic block diagram of an embodiment of a controlled release bio-medical unit 10 that administers potentially complex medications. The bio-medical unit 10 includes a MEMS controlled release module 374, the communication module 50 (e.g., for external communications with the communication device and for communications with other bio-medical units), the processing module 50, the memory 52, and the power harvesting module 46.

The bio-medical unit 10 may communicate with other bio-medical units 10 and/or with a communication device 24 to communicate status information and/or commands. For example, the bio-medical unit 10 may coordinate with at least one other bio-medical unit 10 to provide the administration of medications. The processing module 50 may determine when and how to administer the medication based on a command, a predetermination, and/or an adaptive algorithm (e.g., that detects local pain).

The MEMS controlled release module 374 may contain materials that comprise medications and a unit ID to identify the materials. The processing module 50 may control the MEMS controlled release module 374 to mix particular materials to produce a desired medication in accordance with the unit ID, and the determination of the when and how to administer the medication.

Figure 34:
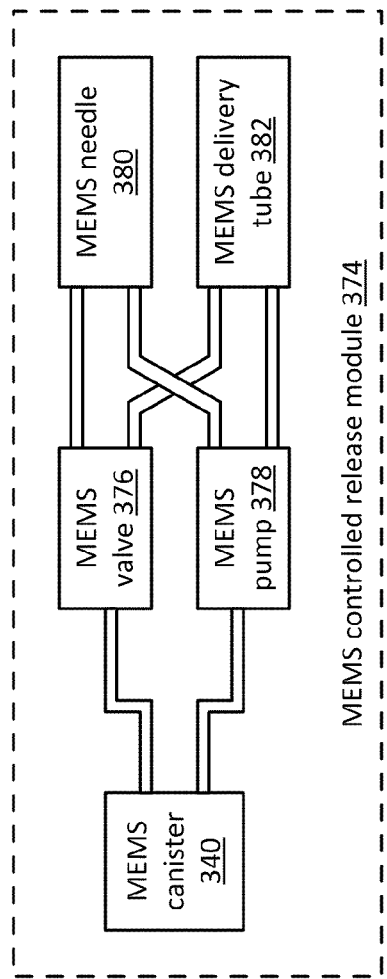
FIG. 34 is a diagram of an embodiment of a controlled release module in accordance with the present invention.

FIG. 34 is a schematic block diagram of an embodiment of a MEMS controlled release module 374 that controls the formation and delivery of medications created with materials previously stored in the MEMS controlled release module 374. The MEMS controlled release module 374 may include a MEMS canister 340, a MEMS valve 376, a MEMS pump 378, a MEMS needle 380, MEMS delivery tube 382, and pathways between the elements. The MEMS canister 340 holds one or more materials. The MEMS valve 376 may control the flow of a material. The MEMS pump 378 may actively move a material. The MEMS needle 380 may facilitate injection of the medication. The MEMS delivery tube 382 may facilitate delivery of the medication.

The MEMS controlled release module 374 may receive requests and/or commands from the processing module 50 including request for unit ID, commands to mix 10% material A and 90% material B, a command to inject the needle, and/or a command to administer the mixture through a MEMS needle 380 and/or MEMS delivery tube 382.

Figure 35:
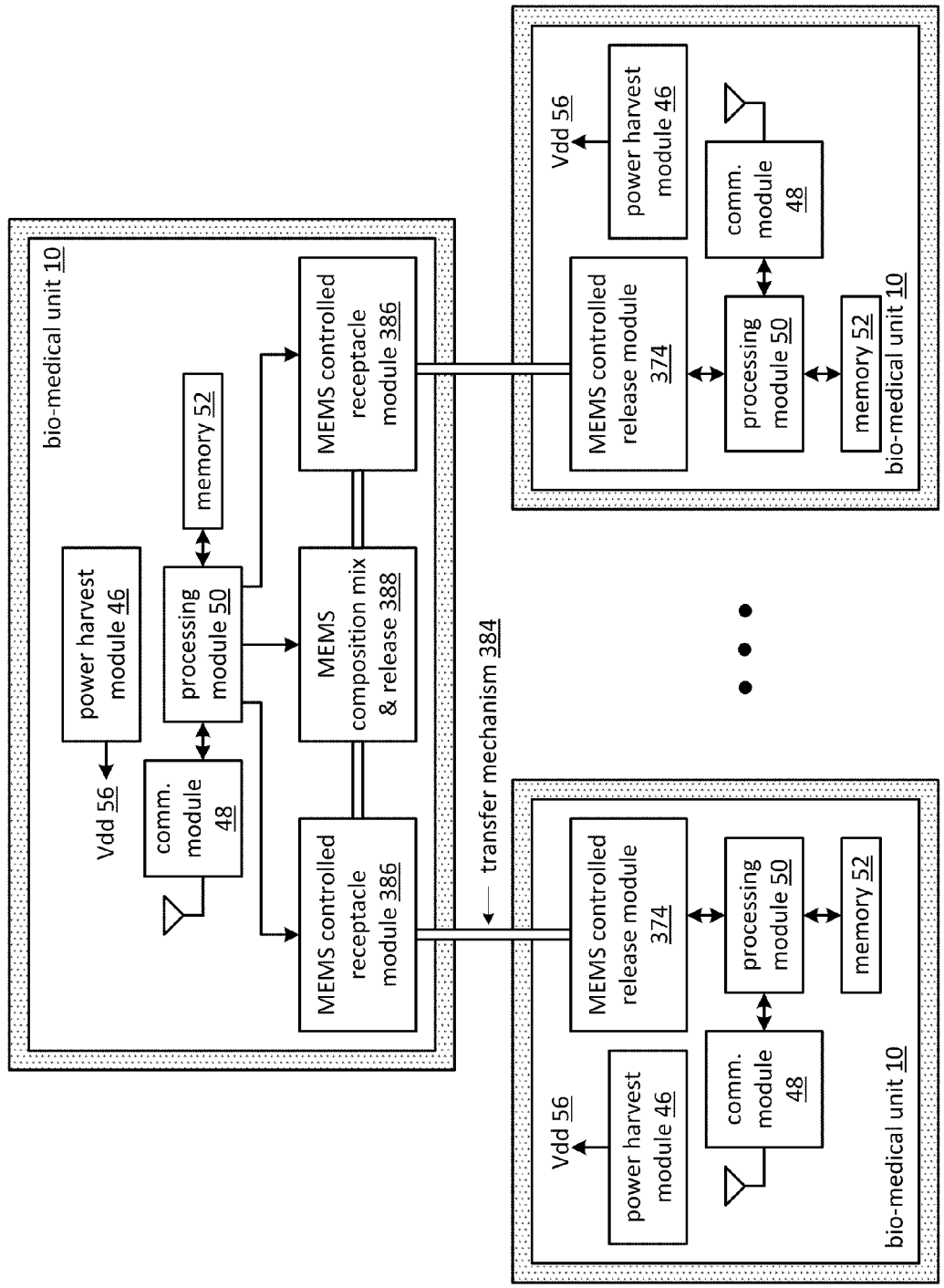
FIG. 35 is a diagram of an embodiment of a system of bio-medical units for controlled release of a medication in accordance with the present invention.

FIG. 35 is a schematic block diagram of an embodiment of a controlled release bio-medical unit 10 system that administers potentially complex medications. A plurality of bio-medical units 10 transfers (e.g., from at least one unit to another), mixes, and administers the medications.

A first type of bio-medical unit 10 includes a MEMS controlled release module 374, the communication module 48 (e.g., for external communications with the communication device and for communications with other bio-medical units), the processing module 50, the memory 52, and the power harvesting module 46. The first type of bio-medical unit 10 substantially provides the medication ingredients to a second type of bio-medical unit 10.

The second type of bio-medical unit 10 includes at least one MEMS controlled receptacle module 386, a MEMS composition mix and release 388, the communication module 48 (e.g., for external communications with the communication device and for communications with other bio-medical units), the processing module 50, the memory 52, and the power harvesting module 46. The second type of bio-medical unit 10 substantially mixes the final medication and administers the medication.

The first and second types of bio-medical unit 10 may communicate with other bio-medical units 10 and/or with a communication device 24 to communicate status information and/or commands. For example, the second type bio-medical unit 10 may coordinate with at least one first type of bio-medical unit 10 to provide the administration of medications.

The processing module 50 of the second type of bio-medical unit 10 may determine when and how to administer the medication based on a command, a predetermination, and/or an adaptive algorithm (e.g., that detects local pain). The processing module 50 of the second type of bio-medical unit 10 may determine which of the plurality of the first type of bio-medical units 10 contain the required materials based on a unit ID status update, a command, and/or a predetermination.

The processing module 50 of the second type of bio-medical unit 10 may send a command to the plurality of the first type of bio-medical units 10 to dock with the second type of bio-medical unit 10 and transfer the required materials to the MEMS controlled receptacle module 386 of the second type of bio-medical unit 10. The processing module 50 of the second type of bio-medical unit 10 may control the MEMS composition mix and release 388 to mix the required materials from the plurality of first type of bio-medical units 10. The processing module 50 of the second type of bio-medical unit 10 may control the MEMS composition mix and release 388 to release the mixture in accordance with the determination of the when and how to administer the medication.

Figure 36:
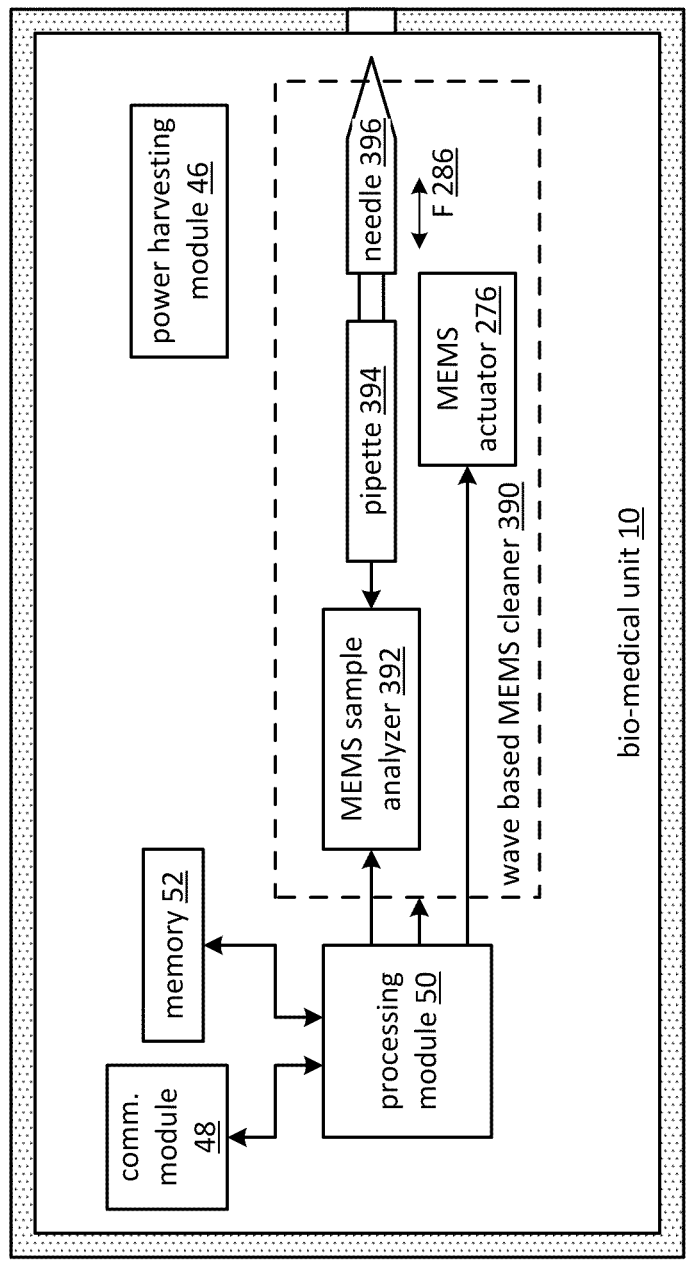
FIG. 36 is a diagram of an embodiment of a bio-medical unit including sampling modules in accordance with the present invention.

FIG. 36 is a schematic block diagram of an embodiment of a self-cleaning sampling bio-medical unit 10 where a wave based MEMS cleaner 390 facilitates cleaning of a sampling sub-system. The bio-medical unit 10 includes the wave based MEMS cleaner 390 for a MEMS sample analyzer 392, a pipette 394, a needle 396, and a MEMS actuator 276. The bio-medical unit 10 also includes the communication module 48 (e.g., for external communications with the communication device and for communications with other bio-medical units), the processing module 50, the memory 52, and the power harvesting module 46.

The processing module 50 may determine when to perform a sampling and cleaning of the sampling sub-system based on a command, a predetermination, and/or an adaptive algorithm (e.g., based on a sample history). The processing module 50 may precede each sampling with a cleaning, follow each sampling with a cleaning, or some combination of both.

The processing module 50 may command the wave based MEMS cleaner 390 to clean the components of the sampling sub-system. The wave based MEMS cleaner 390 may perform the cleaning with one or methods including heating, vibrating, RF energy, laser light, and/or sound waves. In another embodiment, the bio-medical unit 10 includes a MEMS canister 340 with a cleaning agent that is released during the cleaning sequence and expelled through the needle 396.

The processing module 50 may command the MEMS actuator 276 to apply force 286 to move the needle 396 into the sampling position where the needle 396 is exposed to the outside of the bio-medical unit 10 (e.g., extends into the body). The pipette 394 moves the sample from the needle 396 to the MEMS sample analyzer 392.

The MEMS sample analyzer 392 provides the processing module 50 with sample information, which may include blood analysis, pH analysis, temperature, oxygen level, other gas levels, toxin analysis, medication analysis, and/or chemical analysis. The processing module 50 may process the sample information to produce processed sample information. The processing module 50 may send the processed sample information to another bio-medical unit 10 or to a communication unit 24 for further processing.

Figure 37:
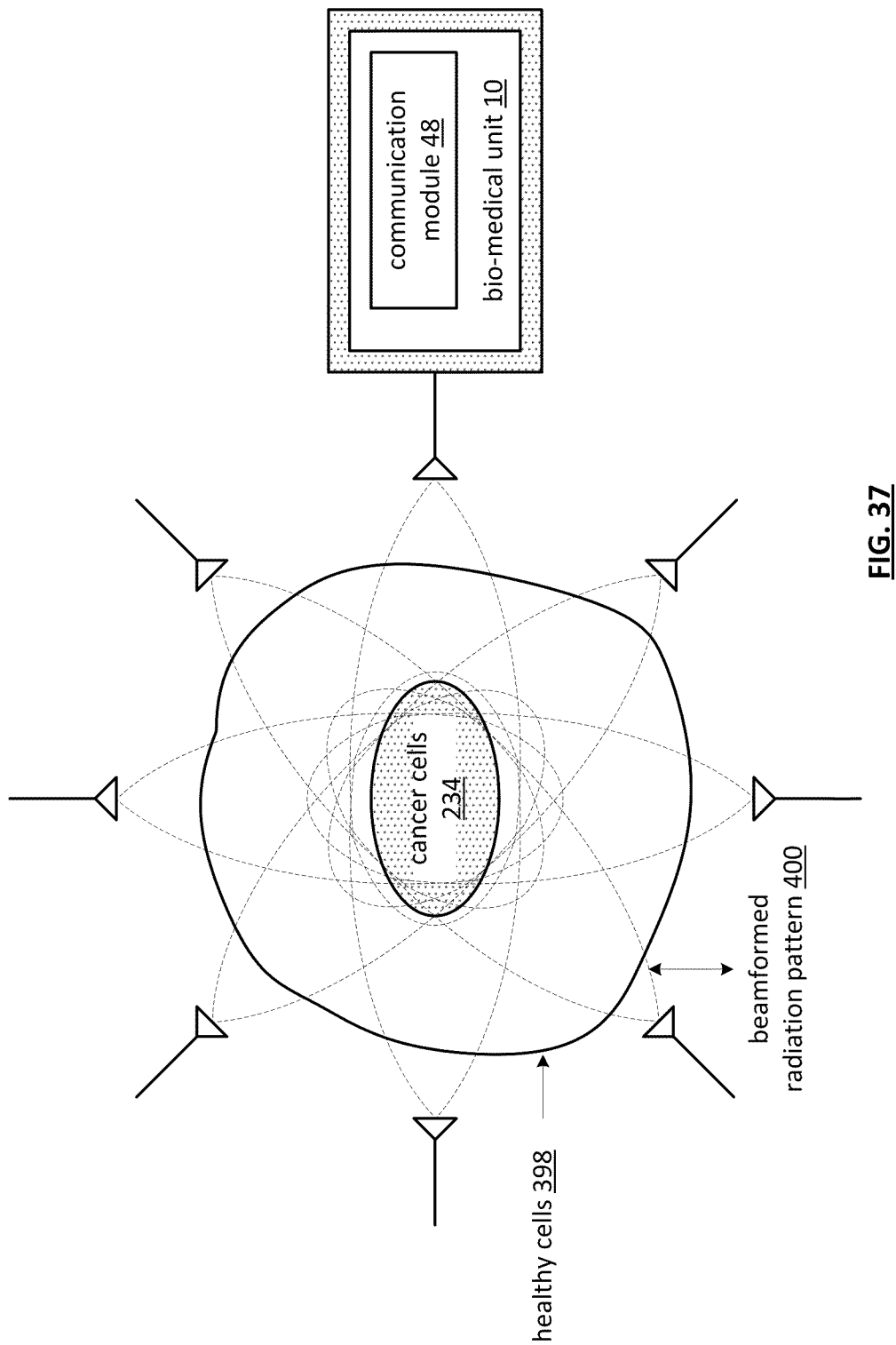
FIG. 37 is a diagram of another embodiment of a network of bio-medical units facilitating cancer treatment in accordance with the present invention.

FIG. 37 is a schematic block diagram of an embodiment of a plurality of energy therapy generating bio-medical units 10 to delivery therapy around a cancer cell mass 234. The bio-medical unit 10 communication module 48 may utilize power control and antenna beam forming in conjunction with one or more other bio-medical unit 10 communication modules 48 such that the resulting composite energy field substantially pinpoints the cancer cells 234. The communication module 48 may radiate energy as RF, MMW, and/or laser light.

The bio-medical unit 10 communication module 48 may communicate with the other bio-medical unit 10 communication modules 48 to coordinate the creation of a beamformed radiation pattern 400 and/or the plurality of communication modules 48 of the plurality of bio-medical units 10 may receive a command from an external communication device 24 containing coordination information. The bio-medical unit 10 may vary the energy generation based on one or more of sensed data (e.g., where the cancer cells are located), a command, and/or available power such that the energy delivered to cancer cells 234 is substantially higher than the energy delivered to healthy cells 398.

Figure 38:
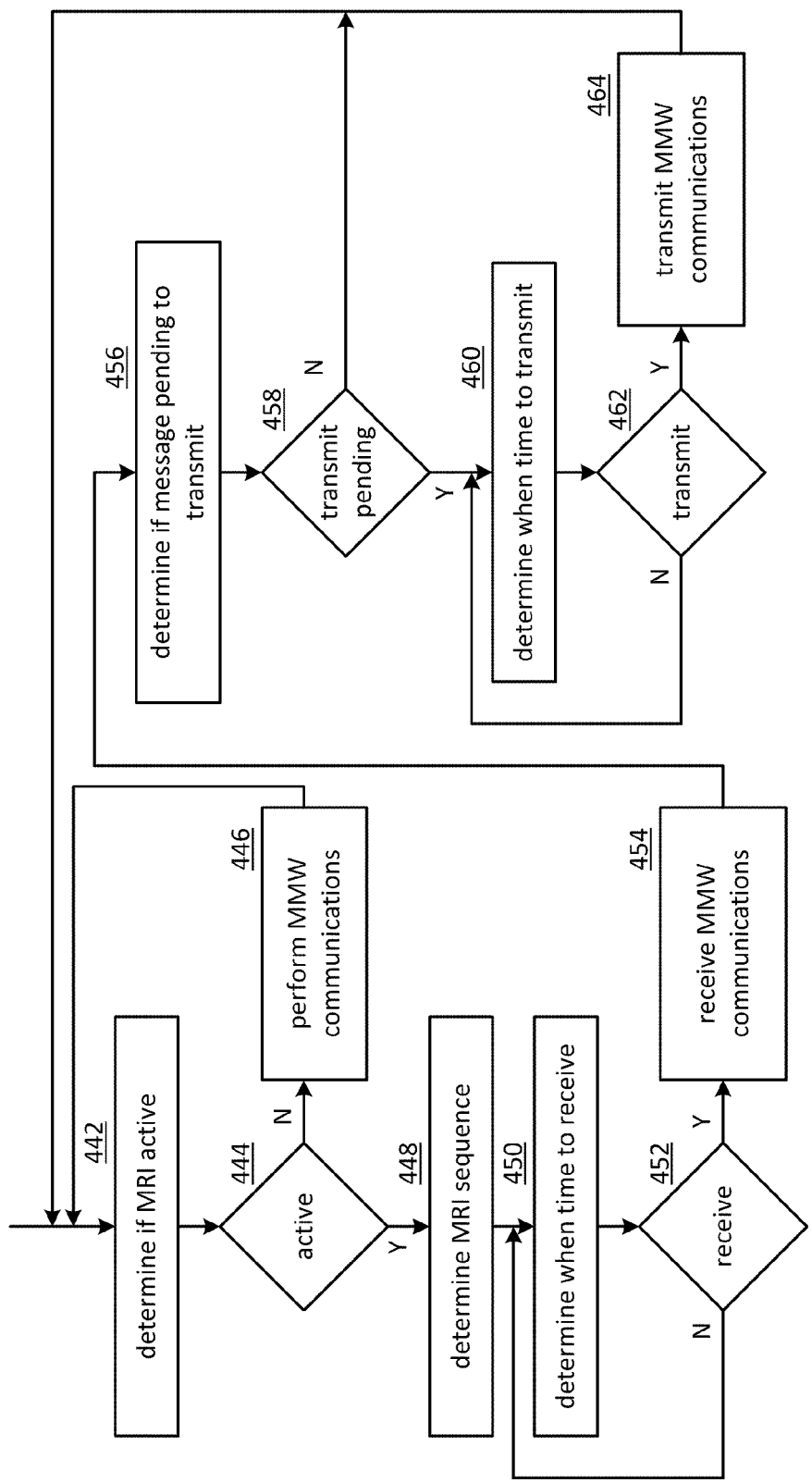
FIG. 38 is a logic diagram of an embodiment of a method for MMW communications within a MRI sequence in accordance with the invention.

FIG. 38 is a flowchart illustrating MMW communications within a MRI sequence where the processing module 50 determines MMW communications in accordance with an MRI sequence. The method begins with step 442 where the processing module 50 determines if the MRI is active based on receiving MRI EM signals. At step 444, the method branches to step 448 when the processing module 50 determines that the MRI is active. At step 444, the method continues to step 446 when the processing module 50 determines that the MRI is not active.

At step 446, the processing module 50 performs MMW communications. In an embodiment, the MRI sequence may not start until the processing module 50 performs MMW communications. The method branches to step 442. At step 448, the processing module 50 determines the MRI sequence based on received MRI EM signals (e.g., gradient pulses and/or MRI RF pulses).

At step 450, the processing module 50 determines when it is time to perform receive MMW communication in accordance with the MRI sequence. In an embodiment, the MMW transceiver 138 may receive MMW inbound signals 148 between any of the MRI sequence steps. In another embodiment, the MMW transceiver 138 may receive MMW inbound signals 148 between specific predetermined steps of the MRI sequence.

At step 452, the method branches back to step 450 when the processing module 50 determines that it is not time to perform receive MMW communication. The method continues when the processing module 50 determines that it is time to perform receive MMW communication. At step 454, the processing module 50 directs the MMW transceiver 138 to receive MMW inbound signals 148. The processing module 50 may decode messages from the MMW inbound signals 148 such that the messages include one or more of a status request, a records request, a sensor data request, a processed data request, a position request, a command, and/or a request for MRI echo signal data.

At step 456, the processing module 50 determines if there is at least one message pending to transmit (e.g., in a transmit queue). The method branches back to step 442 when the processing module 50 determines that there is not at least one message pending to transmit. The method continues to step 460 when the processing module 50 determines that there is at least one message pending to transmit.

At step 460, the processing module 50 determines when it is time to perform transmit MMW communication in accordance with the MRI sequence. In an embodiment, the MMW transceiver 138 may transmit MMW outbound signals 150 between any of the MRI sequence steps. In another embodiment, the MMW transceiver 138 may transmit MMW outbound signals 150 between specific predetermined steps of the MRI sequence.

At step 462, the processing module 50 branches back to step 460 when the processing module 50 determines it is not time to perform transmit MMW communication. The method continues to step 464 when the processing module 50 determines it is time to perform transmit MMW communication. At step 464, the processing module 50 directs the MMW transceiver 138 to prepare the MMW outbound signals 150 based on the at least one message pending to transmit. The processing module 50 may encode messages into the MMW outbound signals 150 such that the messages include one or more of a status request response, a records request response, a sensor data request response, a processed data request response, a position request response, a command response, and/or a request for MRI echo signal data response. The method branches back to step 442.

Figure 39:
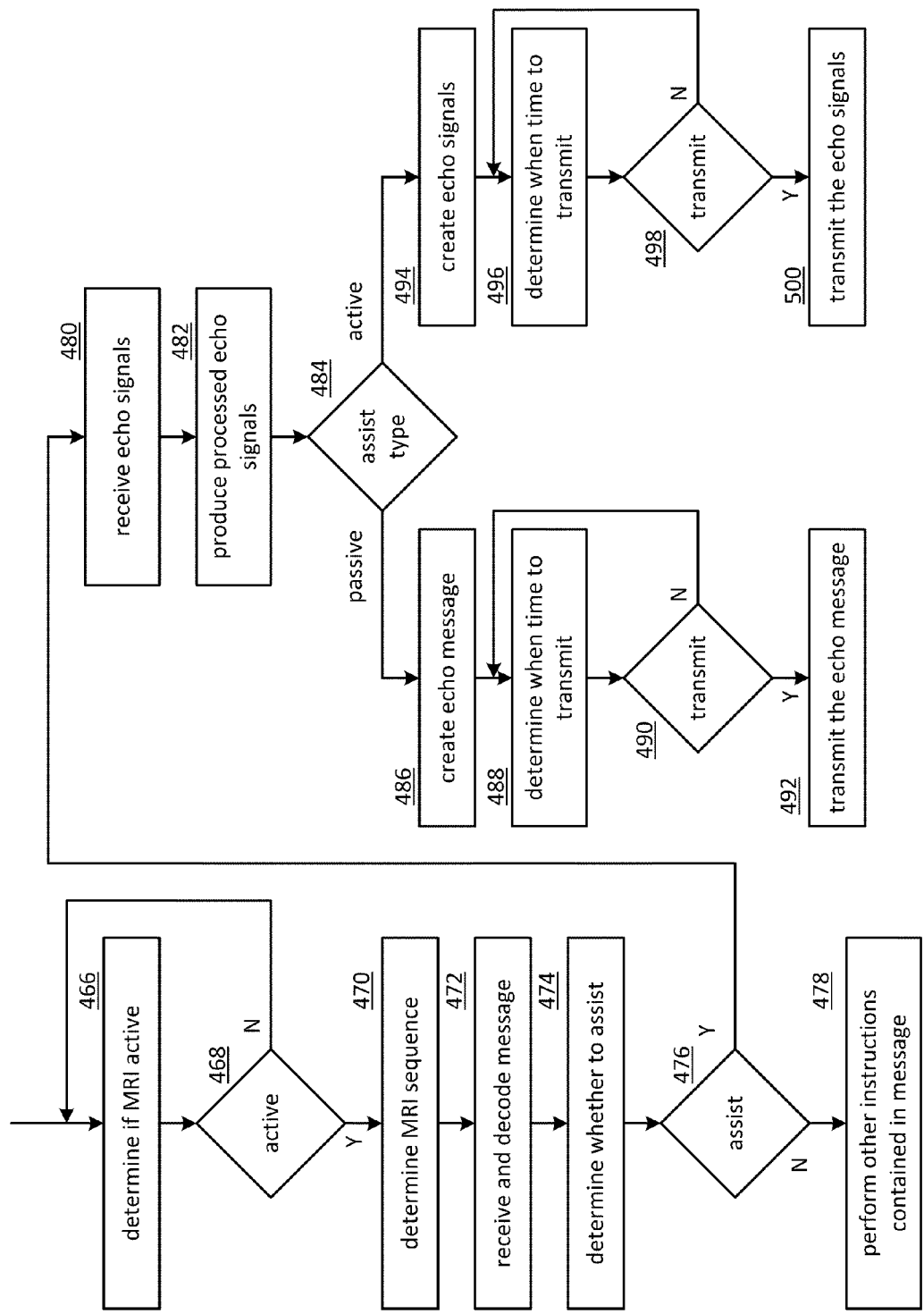
FIG. 39 is a logic diagram of an embodiment of a method for processing of MRI signals in accordance with the present invention.

FIG. 39 is a flowchart illustrating the processing of MRI signals where the processing module 50 of the bio-medical unit 10 may assist the MRI in the reception and processing of MRI EM signals 146. The method begins at step 466 where the processing module 50 determines if the MRI is active based on receiving MRI EM signals 146. The method branches back to step 466 when the processing module 50 determines that the MRI is not active. In an embodiment, the MRI sequence may not start until the processing module 50 communicates to the MRI that it is available to assist. The method continues to step 470 when the processing module 50 determines that the MRI is active.

At step 470, the processing module 50 determines the MRI sequence based on received MRI EM signals 146 (e.g., gradient pulses and/or MRI RF pulses). At step 472, the processing module receives EM signals 146 and/or MMW communication 532 in accordance with the MRI sequence and decodes a message for the processing module 50. In an embodiment, the MMW transceiver 138 may receive MMW inbound signals 148 between any of the MRI sequence steps. In another embodiment, the MMW transceiver 138 may receive MMW inbound signals 148 between specific predetermined steps of the MRI sequence. In yet another embodiment, the processing module 50 may receive EM signals 146 at any point of the MRI sequence such that the EM signals 146 contain a message for the processing module 50. The processing module 50 may decode messages from the EM signals 146 and/or MMW inbound signals 148 such that the messages include one or more of a request to assist in the MRI sequence, a status request, a records request, a sensor data request, a processed data request, a position request, a command, and/or a request for MRI echo signal data.

At step 474, the processing module 50 determines whether to assist in the MRI sequence based in part on the decoded message. The determination may be based on a comparison of the assist request to the capabilities of the bio-medical unit 10. At step 476, the method branches to step 480 when the processing module 50 determines to assist in the MRI sequence. The method continues with step 478 when the processing module 50 determines to not assist in the MRI sequence. At step 478, the processing module 50 performs other instructions contained in the message. The method ends.

At step 480, the processing module 50 begins the assist steps by receiving echo signals 530 during the MRI sequence. Note the echo signals 530 may comprise EM RF signals across a wide frequency band as reflected off of tissue during the MRI sequence. At step 482, the processing module 50 processes the received echo signals 530 to produce processed echo signals. Note that this may be a portion of the overall processing required to lead to the desired MRI imaging.

At step 484, the processing module 50 determines the assist type based on the decoded message from the MRI unit. The assist type may be at least passive or active where the passive type collects echo signal 530 information and sends it to the MRI unit via MMW outbound signals 150 and the active type collects echo signal information and re-generates a form of the echo signals 530 and sends the re-generated echo signals to the MRI unit via outbound modulated EM signals (e.g., the MRI unit interprets the re-generated echo signals as echo signals to improve the overall system gain and sensitivity).

The method branches to step 494 when the processing module 50 determines the assist type to be active. The method continues to step 486 when the processing module 50 determines the assist type to be passive. At step 486, the processing module 50 creates an echo message based on the processed echo signals where the echo message contains information about the echo signals 530.

At step 488, the processing module 50 determines when it is time to transmit the echo message encoded as MMW outbound signals 150 via MMW communication in accordance with the MRI sequence. In an embodiment, the MMW transceiver 138 may transmit MMW outbound signals 150 between any of the MRI sequence steps. In another embodiment, the MMW transceiver 138 may transmit MMW outbound signals 150 between specific predetermined steps of the MRI sequence.

At step 490, the method branches back to step 488 when the processing module 50 determines that it is not time to transmit the echo message. At step 490, the method continues to step 492 when the processing module 50 determines that it is time to transmit the echo message. At step 492, the processing module 50 transmits the echo message encoded as MMW outbound signals 150. The method ends.

At step 494, the processing module 50 creates echo signals based on the processed echo signals. At step 496, the processing module 50 determines when it is time to transmit the echo signals as outbound modulated EM signals 180 in accordance with the MRI sequence. In an embodiment, the EM transceiver 174 may transmit the outbound modulated EM signals 180 between any of the MRI sequence steps. In another embodiment, the EM transceiver 174 may transmit the outbound modulated EM signals 180 between specific predetermined steps of the MRI sequence. In yet another embodiment, the EM transceiver 174 may transmit the outbound modulated EM signals 180 during the time period when the MRI receiver is receiving echo signals 530.

At step 498, the method branches back to step 496 when the processing module 50 determines that it is not time to transmit the echo signals. At step 498, the method continues to step 500 when the processing module 50 determines that it is time to transmit the echo signals. At step 500, the processing module 50 transmits the echo signals encoded as outbound modulated EM signals 180. Note that the transmitted echo signals emulate the received echo signals 530 with improvements to overcome low MRI power levels and/or low MRI receiver sensitivity.

Figure 40:
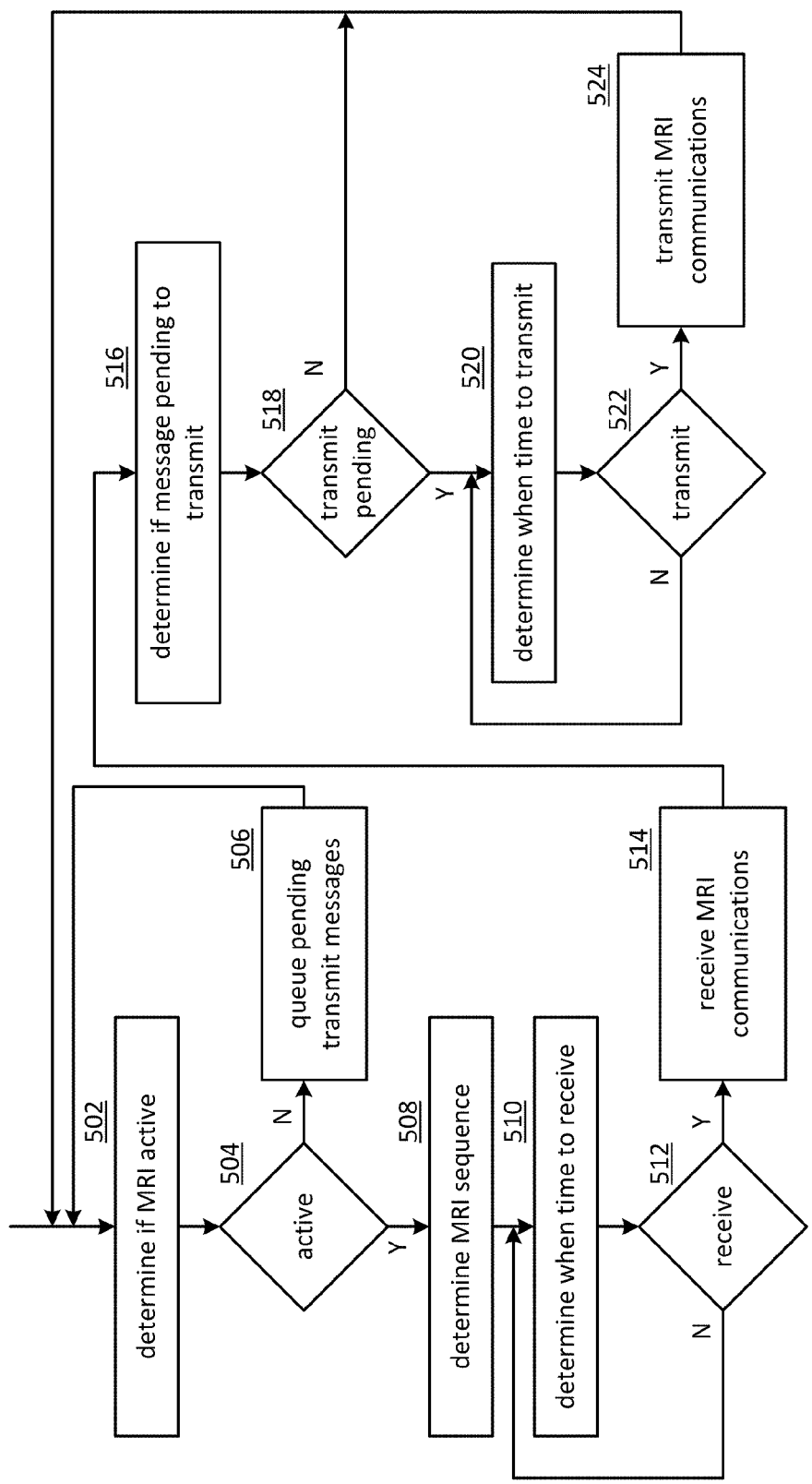
FIG. 40 is a logic diagram of an embodiment of a method for communication utilizing MRI signals in accordance with the present invention.

FIG. 40 is a flowchart illustrating communication utilizing MRI signals where the processing module 50 determines MMW signaling in accordance with an MRI sequence. The method begins at step 502 where the processing module 50 determines if the MRI is active based on receiving MRI EM signals 146. At step 504, the method branches to step 508 when the processing module 50 determines that the MRI is active. At step 504, the method continues to step 506 when the processing module 50 determines that the MRI is not active. At step 506, the processing module 50 queues pending transmit messages. The method branches to step 502.

At step 508, the processing module 50 determines the MRI sequence based on received MRI EM signals 146 (e.g., gradient pulses and/or MRI RF pulses). At step 510, the processing module 50 determines when it is time to perform receive communication in accordance with the MRI sequence. In an embodiment, the EM transceiver 174 may receive inbound modulated EM signals 146 containing message information from any of the MRI sequence steps.

At step 512, the method branches back to step 510 when the processing module 50 determines that it is not time to perform receive communication. At step 512, the method continues to step 514 when the processing module 50 determines that it is time to perform receive communication.

At step 514, the processing module 50 directs the EM transceiver 174 to receive the inbound modulated EM signals. The processing module 50 may decode messages from the inbound modulated EM signals 146 such that the messages include one or more of a echo signal collection assist request, a status request, a records request, a sensor data request, a processed data request, a position request, a command, and/or a request for MRI echo signal data. Note that the message may be decoded from the inbound modulated EM signals 146 in one or more ways including detection of the ordering of the magnetic gradient pulses, counting the number of gradient pulses, the slice pulse orderings, detecting small differences in the timing of the pulses, and/or demodulation of the MRI RF pulse.

At step 516 the processing module 50 determines if there is at least one message pending to transmit (e.g., in a transmit queue). At step 518, the method branches back to step 502 when the processing module 50 determines that there is not at least one message pending to transmit. At step 518, the method continues to step 520 when the processing module 50 determines that there is at least one message pending to transmit.

At step 520, the processing module 50 determines when it is time to perform transmit communication in accordance with the MRI sequence. In an embodiment, the EM transceiver 174 may transmit outbound modulated EM signals 180 between any of the MRI sequence steps. In another embodiment, the EM transceiver 174 may transmit the outbound modulated EM signals 180 between specific predetermined steps of the MRI sequence. In another embodiment, the EM transceiver 174 may transmit the outbound modulated EM signals 180 in parallel with specific predetermined steps of the MRI sequence, but may utilize a different set of frequencies unique to the EM transceiver 174.

At step 522, the method branches back to step 520 when the processing module 50 determines that it is not time to perform transmit communication. At step 522, the method continues to step 524 when the processing module 50 determines that it is time to perform transmit communication.

At step 524, the processing module 50 directs the EM transceiver 174 to prepare the outbound modulated EM signals 180 based on the at least one message pending to transmit. The processing module 50 may encode messages into the outbound modulated EM signals 180 such that the messages include one or more of a status request response, a records request response, a sensor data request response, a processed data request response, a position request response, a command response, and/or a request for MRI echo signal data response. The method branches back to step 502.

Figure 41:
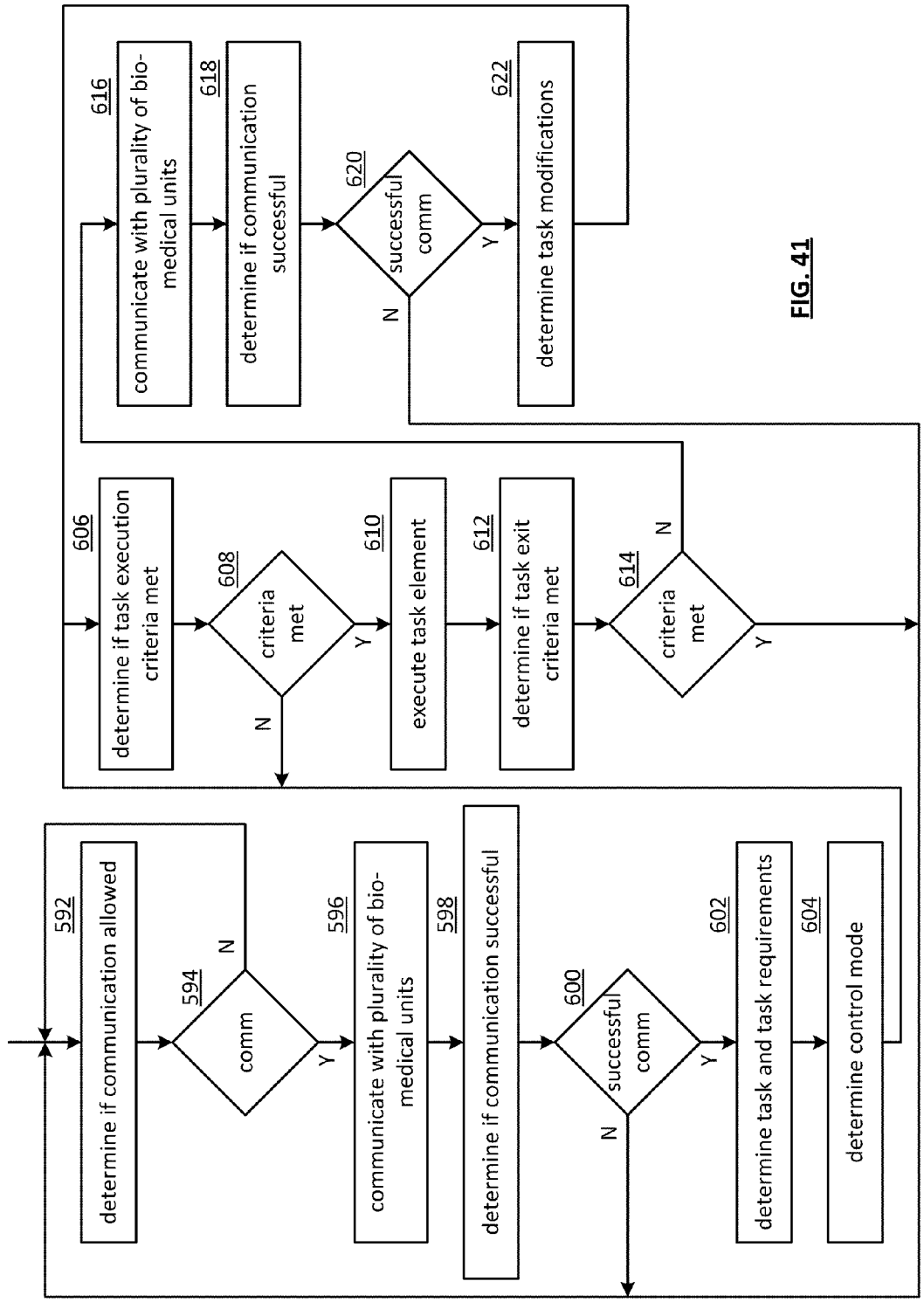
FIG. 41 is a logic diagram of an embodiment of a method for coordination of bio-medical unit task execution in accordance with the present invention.

FIG. 41 is a flowchart illustrating the coordination of biomedical unit task execution where the processing module 50 determines and executes tasks with at least one other biomedical unit 10. The method begins at step 592 where the processing module 50 determines if communication is allowed. The determination may be based on one or more of a timer, a command, available power, a priority indicator, an MRI sequence, and/or interference indicator.

At step 594, the method branches back to step 592 when the processing module 50 determines that communication is not allowed. At step 594, the method continues to step 596 when the processing module 50 determines that communication is allowed. At step 596, the processing module 50 directs the communication module 48 to communicate with a plurality of bio-medical units 10 utilizing RF and/or MMW inbound and/or outbound signals. The processing module 50 may decode messages from the RF and/or MMW inbound and/or outbound signals inbound signals. At step 598, the processing module 50 determines if communications with the plurality of bio-medical units 10 is successful based in part on the decoded messages.

At step 600, the method branches back to step 592 when the processing module determines that communications with the plurality of bio-medical units 10 is not successful. Note that forming a network with the other bio-medical units 10 may be required to enable joint actions. At step 600, the method continues to step 602 when the processing module 50 determines that communications with the plurality of bio-medical units 10 is successful.

At step 602, the processing module 50 determines the task and task requirements. The task determination may be based on one or more of a command from a parent bio-medical unit 10, external communications, a preprogrammed list, and/or in response to sensor data. The task requirements determination may be based on one or more of the task, a command from a parent bio-medical unit 10, external communications, a preprogrammed list, and/or in response to sensor data. Note that the task may include actions including one or more of drilling, moving, sawing, jumping, spreading, sensing, lighting, pinging, testing, and/or administering medication.

At step 604, the processing module 50 determines the control mode based on one or more of a command from a parent bio-medical unit 10, external communications, a preprogrammed list, and/or in response to sensor data. Note that the control mode may include autonomous, parent (bio-medical unit), server, and/or peer.

At step 606, the processing module 50 determines if task execution criteria are met based on sensor data, communication with other bio-medical units 10, a command, a status indicator, a safety indicator, a stop indicator, and/or location information. Note that the task execution criteria may include one or more of safety checks, position information of the bio-medical unit 10, position information of other bio-medical units 10, and/or sensor data thresholds.

At step 608, the method branches back to step 606 when the processing module 50 determines that the task execution criteria are not met. At step 608, the method continues to step 610 when the processing module 50 determines that the task execution criteria are met. At step 610, the processing module 50 executes a task element. A task element may include a portion or step of the overall task. For example, move one centimeter of a task to move three centimeters.

At step 612, the processing module 50 determines if task exit criteria are met based on a task element checklist status, sensor data, communication with other bio-medical units 10, a command, a status indicator, a safety indicator, a stop indicator, and/or location information. Note that the task exit criteria define successful completion of the task.

At step 614, the method branches back to step 592 when the processing module 50 determines that the task exit criteria are met. In other words, the plurality of bio-medical units 10 is done with the current task and is ready for the next task. At step 614, the method continues to step 616 when the processing module 50 determines that the task exit criteria are not met.

At step 616, the processing module 50 directs the communication module 48 to communicate with the plurality of bio-medical units 10 utilizing RF and/or MMW inbound and/or outbound. The processing module 50 may decode messages from the RF and/or MMW inbound and/or outbound signals inbound signals. Note that the messages may include information in regards to task modifications (e.g., course corrections). At step 618, the processing module 50 determines if communications with the plurality of bio-medical units 10 is successful based in part on the decoded messages.

At step 620, the method branches back to step 592 when the processing module determines that communications with the plurality of bio-medical units is not successful (e.g., to potentially restart). Note that maintaining the network with the other bio-medical unit may be required to enable joint actions. At step 620, the method continues to step 622 when the processing module determines that communications with the plurality of bio-medical units is successful.

At step 622, the processing module 50 determines task modifications. The task modifications may be based on one or more of a command from a parent bio-medical unit 10, and/or external communications. The task modifications determination may be based on one or more of the task, a command from a parent bio-medical unit 10, external communications, a preprogrammed list, and/or in response to sensor data. The method branches back to step 606 to attempt to complete the current task.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "coupled to" and/or "coupling" and/or includes direct coupling between items and/or indirect coupling between items via an intervening item (e.g., an item includes, but is not limited to, a component, an element, a circuit, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" indicates that an item includes one or more of power connections, input(s), output(s), etc., to perform one or more its corresponding functions and may further include inferred coupling to one or more other items. As may still further be used herein, the term "associated with", includes direct and/or indirect coupling of separate items and/or one item being embedded within another item. As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

The present invention has also been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention.

The present invention has been described above with the aid of functional building blocks illustrating the performance of certain significant functions. The boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

What is claimed is:

1. A bio-medical unit operable in vivo, the bio-medical unit comprises:
    a power harvesting module operable to convert a wireless power source into a supply voltage;
    a communication module operable to communicate data regarding treatment of cancer cells within a body, wherein the communication module is powered by the supply voltage; and
    a field generation module operable in vivo with adjustable power levels that determines a power level to contain a polarized or ionized cancer treatment drug within an in vivo localized area and that generates a type of electromagnetic field with the power level to attract the polarized or ionized cancer treatment drug within the in vivo localized area.

2. The bio-medical unit of claim 1, wherein the communication module comprises at least one of:
    a radio frequency (RF) transceiver to transceive RF data signals with a communication control device;
    a millimeter wave (MMW) transceiver to transceive MMW data signals with a communication control device; and
    a magnetic resonance transceiver to transceive magnetic resonance data signals with a communication control device.

3. The bio-medical unit of claim 1, wherein the field generation module further functions to perform:
    when the cancer treatment drug is ionized, determine a power level of an electric field to contain the ionized cancer treatment drug approximately within the in vivo localized area that is at least partially encircling the cancer cells and generate the electric field with the power level to contain the ionized cancer treatment drug approximately within the in vivo localized area that is at least partially encircling the cancer cells; or
    when the cancer treatment drug is polarized, determine a power level of a magnetic field to contain the polarized cancer treatment drug approximately within the in vivo localized area that is at least partially encircling the cancer cells and generate the magnetic field with the power level to contain the polarized cancer treatment drug approximately within the in vivo localized area that is at least partially encircling the cancer cells.

4. The bio-medical unit of claim 1, wherein the field generation module further functions to perform at least one of:
    generate an electric field to charge a second substance that contains the cancer treatment drug in the localized area, wherein the localized area is at least partially encircling the cancer cells and wherein the cancer treatment drug is ionized; and
    generate a magnetic field to magnetize a second substance that contains the cancer treatment drug in the localized area, wherein the localized area is at least partially encircling the cancer cells and wherein the cancer treatment drug is polarized.

5. The bio-medical unit of claim 1 further comprises at least one of:
    a first dispensing module operable in vivo to:
        store the polarized or ionized cancer treatment drug in vivo; and
        dispense at least a portion of the polarized or ionized cancer treatment drug in an in vivo localized area at least partially encircling the cancer cells in accordance with a control signal of the data; or
    a second dispensing module operable in vivo to:
        store a second substance that contains the polarized or ionized cancer treatment drug; and
        dispense at least a portion of the second substance in the in vivo localized area at least partially encircling the cancer cells in accordance with a control signal of the data.

6. The bio-medical unit of claim 1 further comprises:
    a propulsion module operable to move the bio-medical unit in accordance with control signals of the data.

7. The bio-medical unit of claim 1 further comprises:
    an imaging module to generate image data regarding the treatment.

8. The bio-medical unit of claim 1, wherein the field generation module includes at least one of:
    a radio frequency (RF) transmitter to transmit RF signals at the cancer cells to facilitate RF radiation of the cancer cells; and
    a millimeter wave (MMW) transmitter to transmit MMW signals at the cancer cells to facilitate MMW radiation of the cancer cells.

9. The bio-medical unit of claim 1, wherein the communication module further functions to:
    receive a first control signal that contains instructions for a first pattern of treatment to be performed; or
    receive a second control signal that contains instructions for a second pattern of treatment to be performed.

10. A bio-medical unit, comprising:
    a communication module operable to receive a communication, wherein the communication includes instructions to transmit at a given power level; and
    a field generation module operable in vivo in response to the communication to generate in an in vivo localized area an electromagnetic field at the given power level to attract at least one of: a polarized cancer treatment drug or an ionized cancer treatment drug within the in vivo localized area.

11. The bio-medical unit of claim 10, wherein the cancer treatment drug is ionized and the field generation module functions to generate an electric field in the in vivo localized area to attract the ionized cancer treatment drug within the in vivo localized area.

12. The bio-medical unit of claim 10, wherein the cancer treatment drug is polarized and the field generation module functions to generate a magnetic field in the in vivo localized area to attract the polarized cancer treatment drug within the in vivo localized area.

13. The bio-medical unit of claim 10, wherein the field generation module further functions to perform at least one of:
    generate an electric field to charge a second substance that contains the cancer treatment drug in the in vivo localized area, wherein the localized area is at least partially encircling the cancer cells and wherein the cancer treatment drug is ionized; and
    generate a magnetic field to magnetize a second substance that contains the cancer treatment drug in the in vivo localized area, wherein the localized area is at least partially encircling the cancer cells and wherein the cancer treatment drug is polarized.

14. The bio-medical unit of claim 10, further comprising:
a power harvesting module operable to convert a wireless power source into a supply voltage; and
wherein the communication module is powered by the supply voltage.

15. The bio-medical unit of claim 10 further comprises at least one of:
a first dispensing module operable to store the polarized or ionized cancer treatment drug in vivo and dispense at least a portion of the cancer treatment drug in vivo; or
a second dispensing module operable to store a second substance that contains the polarized or ionized cancer treatment drug in vivo and dispense at least a portion of the second substance in vivo.

16. The bio-medical unit of claim 10 further comprises:
a propulsion module operable to move the bio-medical unit in accordance with control signals received by the communication module.

17. A method for treatment of cancer, comprising:
determining a power level for an electromagnetic field for attracting a polarized or ionized cancer treatment drug within an in vivo localized area; and
generating by a biomedical unit the electromagnetic field that interacts with the polarized or ionized cancer treatment drug within the in vivo localized area with the power level to attract the polarized or ionized cancer treatment drug.

18. The method of claim 17, further comprising:
attracting the polarized or ionized cancer treatment drug within the in vivo localized area by the electromagnetic field.

19. The method of claim 17, further comprising:
dispensing at least a portion of an ionized cancer treatment drug by the biomedical unit in vivo, wherein the electromagnetic field is an electric field; and
dispensing at least a portion of a polarized cancer treatment drug by the biomedical unit in vivo, wherein the electromagnetic field is a magnetic field.

20. The method of claim 19, further comprising:
receiving instructions by the biomedical unit to position at a given location; and
moving to the given location by the biomedical unit using a propulsion module.

\* \* \* \* \*